(12) United States Patent
Gustafsson et al.

(10) Patent No.: US 8,412,461 B2
(45) Date of Patent: Apr. 2, 2013

(54) SYSTEMS AND METHODS FOR ANTIBODY ENGINEERING

(75) Inventors: Claes Gustafsson, Belmont, CA (US);
Sridhar Govindarajan, Redwood City, CA (US); Jeremy Stephen Minshull, Los Altos, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 192 days.

(21) Appl. No.: 12/726,843

(22) Filed: Mar. 18, 2010

(65) Prior Publication Data

US 2011/0166844 A1 Jul. 7, 2011

Related U.S. Application Data

(63) Continuation of application No. 10/566,954, filed as application No. PCT/US2004/024751 on Jul. 30, 2004, now abandoned.

(60) Provisional application No. 60/491,815, filed on Aug. 1, 2003, provisional application No. 60/536,357, filed on Jan. 14, 2004, provisional application No. 60/536,862, filed on Jan. 15, 2004.

(51) Int. Cl.
*G06F 7/60* (2006.01)
(52) U.S. Cl. ............... 702/19; 703/11; 702/23; 702/27
(58) Field of Classification Search .................. None
See application file for complete search history.

(56) References Cited

U.S. PATENT DOCUMENTS

| | | | |
|---|---|---|---|
| 5,843,708 | A | 12/1998 | Hardman et al. |
| 7,117,096 | B2 | 10/2006 | Luo et al. |
| 2002/0048772 | A1 | 4/2002 | Dahiyat et al. |
| 2002/0119492 | A1 | 8/2002 | Chirmo et al. |
| 2002/0177170 | A1 | 11/2002 | Luo et al. |
| 2004/0072245 | A1 | 4/2004 | Gustafsson et al. |
| 2004/0161796 | A1 | 8/2004 | Gustafsson et al. |
| 2006/0136184 | A1 | 6/2006 | Gustafsson et al. |
| 2006/0205003 | A1 | 9/2006 | Gustafsson et al. |
| 2007/0239364 | A1 | 10/2007 | Fox |
| 2008/0050357 | A1 | 2/2008 | Gustafsson et al. |
| 2011/0059860 | A1 | 3/2011 | Gustafsson et al. |

FOREIGN PATENT DOCUMENTS

| | | |
|---|---|---|
| WO | WO 03/075129 A2 | 9/2003 |
| WO | WO 2005/012877 A2 | 2/2005 |
| WO | WO 2005/013090 A2 | 2/2005 |
| WO | WO 2005/013090 A3 | 2/2005 |

OTHER PUBLICATIONS

Adenot et al., 1999, "Peptides quantitative structure-function relationships: An automated mutation strategy to design peptides and pseudopeptides from substitution matrices," Journal of Molecular Graphics and Modeling 17, pp. 292-309.

Agrafiotis et al., 2002, "On the use of neural network ensembles in QSAR and QSPR," J Chem Inf Comput Sci, vol. 42, pp. 903-911.
Damborský, 1998, "Quantitative structure-function and structure-stability relationships of purposely modified proteins," Protein Engineering 11, pp. 21-30.
Del Sol Mesa et al., 2003, "Automatic Methods for Predicting Functionally Important Residues," J. Mol. Biol. 326, pp. 1289-1302.
Fariselli et al., 2002, "Prediction of protein-protein interaction sites in heterocomplexes with neural networks," Eur. J. Biochem 269, pp. 1356-1361.
Fox et al., 2003, "Optimizing the search algorithm for protein engineering by directed evolution," Protein Engineering vol. 16, pp. 589-597.
Free et al., 1964, "A mathematical contribution to structure-activity studies," Journal of Medicinal Chemistry, American Chemical Society, vol. 7, No. 4, pp. 395-399.
Govindarajan et al., 2003, "Systematic Variation of Amino Acid Substitutions for Stringent Assessment of Pairwise Covariation," J. Mol. Biol. 328, pp. 1061-1069.
Gustafsson et al., 2001, "Exploration of sequence space for protein engineering," Journal of Molecular Recognition vol. 14, pp. 308-314.
Gustafsson et al., 2003, "Putting engineering back into protein engineering: bioinformatic approaches to catalyst design," Current Opinion in Biotechnology 14: 366-370.
Iiayes et al., 2002, "Combining computational and experimental screening for rapid optimization of protein properties," PNAS vol. 99, pp. 15926-15931.
Hellberg et al., 1986, "Peptide Quantitative Structure-Activity Relationships, a Multivariate Approach," J. Med. Chem 30, pp. 1126-1135.
Irini et al., 2002, "Additive method for the Prediction of Protein-Peptide Binding Affinity. Application to the MHC Class I Molecule HLA-A*0201," Journal of Proteome Research, vol. 1, No. 3, pp. 263-272.
Jonsson et. al., 1993, "Quantitative sequence-activity models (QSAM)-tools for sequence design," Nucleic Acids Research 21, pp. 733-739.

(Continued)

*Primary Examiner* — Michael Borin
(74) *Attorney, Agent, or Firm* — Morgan, Lewis & Bockius LLP

(57) ABSTRACT

Methods, computer systems, and computer program products for antibody engineering. A variant set for an antibody of interest is constructed by identifying, using a plurality of rules, a plurality of positions in the antibody of interest and, for each respective position in the plurality of positions, substitutions for the respective position. The plurality of positions and the substitutions for each respective position in the plurality of position collectively define an antibody sequence space. A variant set comprising a plurality of variants of the antibody is selected. A property of all or a portion of the variants in the variant set is measured. A sequence-activity relationship is modeled between (i) one or more substitutions at one or more positions of the antibody of interest represented by the variant set and (ii) the property measured for all or the portion of the variants in the variant set. The variant set is redefined to comprise variants that include substitutions in the plurality of positions that are selected based on a function of the sequence-activity relationship.

75 Claims, 37 Drawing Sheets

OTHER PUBLICATIONS

Kosiii et al., "Mutation Matrices and Physical-Chemical Properties: Correlations and Implications," 1997, Proteins: Structure, Function and Genetics, vol. 27, pp. 336-344.

Lu et al., 2001, "Predicting the reactivity of proteins from their sequence alone. Kazal family of protein inhibitors of serine proteinases," PNAS 98, pp. 1410-1415.

Ness et al., 2001, "Molecular Breeding: The Natural Approach to Protein Design," Advances in Protein Chemistry 55, pp. 261-292.

Norinder et al., 1997, "A Quantitative Structure-Activity Relationship Study of Some Substance P-related Peptides. A Multivariate Approach using PLS and Variable Selection," Journal of Peptide Research vol. 49, No. 2, pp. 155-162.

Pierce et al., 2002, "Protein Design is NP-hard," Protein Engineering 15, pp. 779-782.

Sandberg et al., 1993, "Engineering multiple properties of a protein by combinatorial mutagenesis," Proc. Natl. Acad. Sci. 90, pp. 8367-8371.

Schneider et al., 1998, "Peptide design by artificial neural networks and computer-based evolutionary," Biochemistry, vol. 95, Issue 21, pp. 12179-12184.

Siiaw et al., 2002, "Predicting Amino Acid Residues Responsible for Enzyme Specificity Solely from Protein Sequences," Biotechnology and Bioengineering 79, pp. 295-300.

Svetnik et al., 2003, "Random Forest: A Classification and Regression Tool for Compound Classification and QSAR Modeling," J Chem Inf Comput Sci, vol. 43, No. 6, pp. 1947-1958.

Wrede et al. 1998, "Peptide Design Aided by Neural Networks; Biological Activity of Artificial Signal Peptidase I Cleavage Sites," Biochemistry 37, pp. 3588-3593.

EPO, Supplementary European Search Report dated Jan. 12, 2007 for European application No. 04779720.4.

EPO, Partial European Search Report dated Oct. 13, 2008 for European application No. 08003668.4.

EPO, Communication relating to Partial European Search Report dated Mar. 4, 2009 for EP 08003668.4.

EPO, Communication pursuant to Article 94(3) EPC dated Aug. 18, 2009 for EP 08003668.4.

ISA, PCT International Search Report dated Feb. 21, 2006 for application No. PCT/US2004/024751.

ISA, PCT International Search Report and Written Opinion dated Feb. 24, 2006 for International Application No. PCT/US04/24752.

```
┌─────────────────────────────────────────────────┐
│ Selection of antibody with some initial binding (step 1) │
└─────────────────────────────────────────────────┘
                        │
                        ▼
┌─────────────────────────────────────────────────┐
│ Initial design                                   │
│ a) Identify positions where substitution is acceptable and │
│ choose substitution s to explore. (step 2)       │
│ b) Design an initial small set of variants using experimental │
│ design methods. (step 3)                         │
└─────────────────────────────────────────────────┘
```

Optionally add new substitutions from step 02 for inclusion in the new variant set Modify initial selection parameters based on performance (Step 09)

Synthesize and test antibody variant set for target binding and viral neutralizing activity. (step 4)

Propose a new variant set based on the model. (step 7)

Iterate

End-point reached

Derive sequence –activity relationships (step 5)

Combine results from different sequence-function models. (step 6)

Select the best variant(s) (step 8). Use sequences and activities of these variants to modify algorithms used for substitution selection (step 9) and sequence-function modeling. (step 10)

Modify methods for combining different sequence-function models based on performance (Step 10)

Figure 2

E coli leader peptide
```
-20          -10       -1
MKKLLFAIPL  VVPFYSHSTM    (SEQ ID NO.: 1)
```

Proteinase K
```
1           11          21          31          41
APAVEQRSEA  APLIEARGEM  VANKYIVKFK  EGSALSALDA  AMEKISGKPD 51          61          71          81          91
HVYKNVFSGF  AATLDENMVR  VLRAHPDVEY  IEQDAVVTIN  AAQTNAPWGL 101         111         121         131         141
ARISSTSPGT  STYYYDESAG  QGSCVYVIDT  GIEASHPEFE  GRAQMVKTYY 151         161         171         181         191
YSSRDGNGHG  THCAGTVGSR  TYGVAKKTQL  FGVKVLDDNG  SGQYSTIIAG 201         211         221         231         241
MDFVASDKNN  RNCPKGVVAS  LSLGGGYSSS  VNSAAARLQS  SGVMVAVAAG 251         261         271         281         291
NNNADARNYS  PASEPSVCTV  GASDRYDRRS  SFSNYGSVLD  IFGPGTSILS 301         311         321         331         341
TWIGGSTRSI  SGTSMATPHV  AGLAAYLMTL  GKTTAASACR  YIADTANKGD 351         361         371
LSNIPFGTVN  LLAYNNYQAV  DHHHHHH   (SEQ ID NO.: 2)
```

Figure 6

```
-60        -50        -40        -30        -20        -10        -1
atgaaaaaac tgctgttcgc gattccgctg gtggtgccgt tctatagcca tagcaccatg 1          11         21         31         41         51
GCACCGGCCG TTGAACAGCG TTCTGAAGCA GCTCCTCTGA TTGAGGCACG TGGTGAAATG 61         71         81         91         101        111
GTAGCAAACA AGTACATCGT GAAGTTCAAG GAGGGTTCTG CTCTGTCTGC TCTGGATGCT 121        131        141        151        161        171
GCTATGGAAA AGATCTCTGG CAAGCCTGAT CACGTCTATA AGAACGTGTT CAGCGGTTTC 181        191        201        211        221        231
GCAGCAACTC TGGACGAGAA CATGGTCCGT GTACTGCGTG CTCATCCAGA CGTTGAATAC 241        251        261        271        281        291
ATCGAACAGG ACGCTGTGGT TACTATCAAC GCGGCACAGA CTAACGCACC TTGGGGTCTG 301        311        321        331        341        351
GCACGTATTT CTTCTACTTC CCCGGGTACG TCTACTTACT ACTACGACGA GTCTGCCGGT 361        371        381        391        401        411
CAAGGTTCTT GCGTTTACGT GATCGATACG GGCATCGAGG CTTCTCATCC TGAGTTTGAA 421        431        441        451        461        471
GGCCGTGCAC AAATGGTGAA GACCTACTAC TACTCTTCCC GTGACGGTAA TGGTCACGGT 481        491        501        511        521        531
ACTCATTGCG CAGGTACTGT TGGTAGCCGT ACCTACGGTG TTGCTAAGAA AACGCAACTG 541        551        561        571        581        591
TTCGGCGTTA AAGTGCTGGA CGACAACGGT TCTGGTCAGT ACTCCACCAT TATCGCGGGT 601        611        621        631        641        651
ATGGATTTCG TAGCGAGCGA TAAAAACAAC CGCAACTGCC CGAAAGGTGT TGTGGCTTCT 661        671        681        691        701        711
CTGTCTCTGG GTGGTGGTTA CTCCTCTTCT GTTAACAGCG CAGCTGCACG TCTGCAATCT 721        731        741        751        761        771
TCCGGTGTCA TGGTCGCAGT AGCAGCTGGT AACAATAACG CTGATGCACG CAACTACTCT 781        791        801        811        821        831
CCTGCTAGCG AGCCTTCTGT TGCACCGTG GGTGCATCTG ATCGTTATGA TCGTCGTAGC 841        851        861        871        881        891
TCCTTCAGCA ACTATGGTTC CGTCCTGGAT ATCTTCGGCC CTGGTACTTC TATCCTGTCT
```

Figure 7A

```
901        911        921        931        941        951
ACCTGGATTG GCGGTAGCAC TCGTTCCATT TCCGGTACGA GCATGGCTAC TCCACATGTT 961        971        981        991        1001       1011
GCTGGTCTGG CAGCATACCT GATGACCCTG GGTAAGACCA CTGCTGCATC CGCTTGTCGT 1021       1031       1041       1051       1061       1071
TACATCGCGG ATACTGCGAA CAAAGGCGAT CTGTCTAACA TCCCGTTCGG CACCGTTAAT 1081       1091       1101       1111       1121       1131
CTGCTGGCAT ACAACAACTA TCAGGCTgtc gaccatcatc atcatcatca tag
```

(SEQ ID NO.: 3)

Figure 7B gi|19171215|emb|CAD20578.1|/89
gi|19171217|emb|CAD20579.1|/1-
gi|19171219|emb|CAD20580.1|/1-
gi|19171221|emb|CAD20581.1|/1-
gi|16215662|emb|CAC95042.1|/90
gi|16506136|dbj|BAB70705.1|/78
gi|16506134|dbj|BAB70704.1|/78
gi|16506140|dbj|BAB70707.1|/78
gi|16215677|emb|CAC95049.1|/90
gi|117631|sp|P29138|CUDP_METAN
gi|6624958|emb|CAB63911.1|/90-
gi|16215669|emb|CAC95045.1|/90
gi|460032|gb|AAA91584.1|/84-36
gi|6634475|emb|CAB64346.1|/87-
gi|16215664|emb|CAC95043.1|/87
gi|2351388|gb|AAC49831.1|/86-3
gi|8671180|emb|CAB95012.1|/85-
gi|16215666|emb|CAC95044.1|/85
gi|16215671|emb|CAC95046.1|/85
gi|4092486|gb|AAC99421.1|/64-2
gi|18542429|gb|AAL75579.1|AF46
SUTIKA/91-367
gi|131077|sp|P06873|PRTK_TRIAL
gi|230675|pdb|2PRK|/1-277
gi|494434|pdb|1PEK|E/1-277
gi|224977|prf||1205229A/1-275
gi|14278658|pdb|1IC6|A/1-277
gi|131084|sp|P23653|PRTR_TRIAL
gi|4761119|gb|AAD29255.1|AF104
gi|14626933|gb|AAK70804.1|/81-
gi|639712|gb|AAC48979.1|/83-34
gi|742825|prf||2011184A/34-362
gi|628051|pir||JC2142/84-362
gi|15808791|gb|AAL08502.1|AF41
gi|15808805|gb|AAL08509.1|AF41
gi|28918475|gb|EAA28148.1|/90-
gi|10181226|gb|AAC27316.2|/92-
gi|131088|sp|P20015|PRTT_TRIAL
gi|9971109|emb|CAC07219.1|/86-
gi|7543916|emb|CAB87194.1|/89-
gi|5813790|gb|AAD52013.1|AF082
gi|23894244|emb|CAD23614.1|/11
gi|22652141|gb|AAN03634.1|AF40
gi|24528136|emb|CAD24010.1|/10
gi|24528132|emb|CAD24008.1|/10
A35742./126-403
gi|114081|sp|P08594|AQL1_THEAQ
AAA82980./129-408
gi|15640187|ref|NP_229814.1|/1
AAA22247./107-381

Figure 8

| Residue | PC1 contrib. | PC2 contrib. | PC1+2 contrib. |
|---|---|---|---|
| 15D | -0.0881 | -0.0803 | -0.1684 |
| 18D | -0.0881 | -0.0803 | -0.1684 |
| 19Q | -0.0881 | -0.0803 | -0.1684 |
| 22L | -0.0881 | -0.0803 | -0.1684 |
| 23P | -0.0881 | -0.0803 | -0.1684 |
| 65Y | -0.0881 | -0.0803 | -0.1684 |
| 66D | -0.0881 | -0.0803 | -0.1684 |
| 110R | -0.0881 | -0.0803 | -0.1684 |
| 137P | -0.0881 | -0.0803 | -0.1684 |
| 164D | -0.0881 | -0.0803 | -0.1684 |
| 189C | -0.0881 | -0.0803 | -0.1684 |
| 198R | -0.0881 | -0.0803 | -0.1684 |
| 8P | -0.0772 | -0.0777 | -0.1549 |
| 34T | -0.0772 | -0.0777 | -0.1549 |
| 67A | -0.0772 | -0.0777 | -0.1549 |
| 75Q | -0.0772 | -0.0777 | -0.1549 |
| 161T | -0.0772 | -0.0777 | -0.1549 |
| 199V | -0.0772 | -0.0777 | -0.1549 |
| 167V | -0.0899 | -0.0589 | -0.1488 |
| 21D | -0.0733 | -0.0657 | -0.1390 |
| 169N | -0.0613 | -0.0746 | -0.1359 |
| 134H | -0.0675 | -0.0664 | -0.1339 |

Figure 12

| Variation | Score | Primary contribution to score |
|---|---|---|
| N95C | 5 | Structural stability at higher temperature: from published literature |
| P97S | 3 | P to S for flexibility and structural perturbabtion |
| S107D | 5 | from active homologs |
| S123A | 7 | Thermostable consensus |
| E138A | 5 | From experiments in literature |
| M145F | 5 | From experiments to improve thermostability |
| Y151A | 8 | From experiments to improve thermostability |
| V167I | 10 | Allow user specified conservative changes (controlled perturbation) |
| L180I | 10 | Allow user specified conservative changes (controlled perturbation) |
| Y194S | 10 | Varaiation observed in highly active clone from our initial exp. |
| A199S | 8 | Allow user specified conservative changes (controlled perturbation) |
| K208H | 7 | PCA modelling of homologs collected from GenBank. |
| A236V | 7 | PCA modelling of homologs collected from GenBank. |
| R237N | 5 | From experiments to improve thermostability (in literature) |
| P265S | 3 | P to S for flexibility and structural perturbabtion |
| V267I | 10 | Allow user specified conservative changes (controlled perturbation) |
| S273T | 15 | Multiple sources identify this change. (thermostability and other) |
| G293A | 8 | For thermostability considerations (observed in thermitases) |
| L299C | 5 | For disulphide bridges with N95C ( from literature) |
| I310K | 5 | from structural studies |
| K332R | 8 | for thermostability considerations (observed in thermitases) |
| S337N | 8 | for thermostability considerations (observed in thermitases) |
| P355S | 3 | P to S for flexibility and structural perturbabtion |

Figure 13 variant-1: 123, 151, 293, 310, 332, 355
variant-2: 95, 145, 167, 199, 237, 273
variant-3: 97, 138, 180, 194, 236, 267
variant-4: 107, 132, 208, 265, 299, 337
variant-5: 123, 145, 151, 167, 273, 337
variant-6: 97, 107, 180, 236, 237, 310
variant-7: 123, 138, 199, 208, 265, 355
variant-8: 95, 194, 267, 293, 299, 332
variant-9: 95, 132, 138, 145, 167, 208
variant-10: 236, 237, 273, 293, 332, 355
variant-11: 97, 123, 265, 299, 310, 337
variant-12: 107, 151, 180, 194, 199, 267
variant-13: 95, 107, 123, 180, 194, 337
variant-14: 138, 151, 167, 199, 208, 299
variant-15: 97, 145, 237, 273, 293, 310
variant-16: 132, 236, 265, 267, 332, 355
variant-17: 97, 151, 199, 236, 299, 355
variant-18: 95, 107, 167, 180, 293, 310
variant-19: 145, 237, 265, 267, 332, 337
variant-20: 123, 132, 138, 194, 208, 273
variant-21: 123, 208, 236, 267, 293, 299
variant-22: 107, 132, 138, 145, 337, 355
variant-23: 97, 180, 194, 199, 265, 310
variant-24: 95, 151, 167, 237, 273, 332

Figure 14

| Variant # | Changes | Reasons |
|---|---|---|
| variant-25 | 95 | Confirm detrimental effect on enzyme |
| variant-26 | 97 | Confirm detrimental effect on enzyme |
| variant-27 | 138 | Confirm detrimental effect on enzyme |
| variant-28 | 208 | Confirm detrimental effect on enzyme |
| variant-29 | 236 | Confirm detrimental effect on enzyme |
| variant-30 | 237 | Confirm detrimental effect on enzyme |
| variant-31 | 265 | Confirm detrimental effect on enzyme |
| variant-32 | 299 | Confirm detrimental effect on enzyme |
| variant-33 | 107, 123, 145 | New combinations of positive changes |
| variant-34 | 151, 167, 180 | New combinations of positive changes |
| variant-35 | 194, 199, 267 | New combinations of positive changes |
| variant-36 | 273, 293, 310 | New combinations of positive changes |
| variant-37 | 332, 337, 355 | New combinations of positive changes |
| variant-38 | 107, 151, 194, 273, 332 | New combinations of positive changes |
| variant-39 | 123, 167, 199, 293, 337 | New combinations of positive changes |
| variant-40 | 145, 180, 267, 310, 355 | New combinations of positive changes |
| variant-41 | 107, 167, 267, 273, 337 | New combinations of positive changes |
| variant-42 | 123, 180, 194, 293, 355 | New combinations of positive changes |
| variant-43 | 145, 151, 199, 310, 332 | New combinations of positive changes |
| variant-44 | 145, 167, 194 | New combinations of positive changes |
| variant-45 | 180, 199, 273 | New combinations of positive changes |
| variant-46 | 267, 293, 332 | New combinations of positive changes |
| variant-47 | 310, 337, 107 | New combinations of positive changes |
| variant-48 | 355, 123, 151 | New combinations of positive changes |

Figure 15

| Sequence changes | | | Variants | | | | | | | | | | | | | | | | |
|---|---|---|---|---|---|---|---|---|---|---|---|---|---|---|---|---|---|---|---|
| Position | WT | Mut | 10 | 12 | 13 | 14 | 15 | 19 | 20 | 21 | 22 | 23 | 24 | 25 | 26 | 27 | 29 | 30 | 31 |
| 25 | Y | H | | | | | | | | | | | H | | | | | | |
| 34 | A | S | | | | | | | | | | | | | S | | | | |
| 48 | K | E | | | | | | | | | | | | | | | | | |
| 50 | D | N | | | | | | | N | | | | | | | | | | |
| 55 | N | S | | | | | | | | | | | | | S | | | | | |
| 63 | T | S | | | | | | | | | | | | | | | | | |
| 88 | T | I | | | | | | | | | | | | | | | | | |
| 95 | N | C | | | | | | | | | | | | | | | | | |
| 97 | P | S | | | | | | | | | | | | | | | | | |
| 107 | S | D | | | | D | | | | | | | | | | | | D | D |
| 123 | S | A | | A | | | | | | | | | | | | | | | |
| 132 | I | V | | | V | | | | | | | | | | | | | | |
| 138 | E | A | | | | | | | | | | | | | | | | | |
| 145 | M | F | | | F | | | | | | | | | | | | | | |
| 151 | Y | A | | A | A | A | | | | | | A | A | A | | | | A | A |
| 167 | V | I | | | I | | | | | | | I | I | I | | | | | |
| 180 | L | I | | | | I | | | | | | I | I | I | | | | | |
| 194 | Y | S | S | | | S | | | | | | | | | S | | | S | S |
| 199 | A | S | | | | S | | | | | | | | | S | | | | |
| 208 | K | H | | | | | H | | | | | | | | | | | | |
| 209 | N | K | | | | | | | | | | | | | | | | | |
| 233 | S | N | | | | | | | | | | | | | | | | | |
| 236 | A | V | | | | | | | | | | | | | | | | | |
| 237 | R | N | | | | | | N | | N | N | | | | | | | | |
| 265 | P | S | | | | | | | | | | S | | | | | | | |
| 267 | V | I | | | | I | | | | | | | | | | I | | | |
| 273 | S | T | | | T | | T | | | | | | | | | T | | T | T |
| 293 | G | A | | A | | | A | | | | | | | | | A | | | |
| 299 | L | C | | | | | | | | | | | | | | | | | |
| 310 | I | K | | K | | | | | | | | | | | | K | | | |
| 332 | K | R | | R | | | R | | | | | | | | | | R | R | R |
| 337 | S | N | | | N | | | | | | | | | | | | N | | |
| 355 | P | S | | S | | | S | | | | | | | | | | S | | |
| 362 | L | M | | | | | | | M | | | | | | | | | | |
| 363 | A | V | | | | | | | | | | | V | | | | | | |
| 369 | A | V | | | | | | | | | | | | | | | | | |

Figure 16A

| Sequence changes | | | Variants | | | | | | | | | | | | | | | |
|---|---|---|---|---|---|---|---|---|---|---|---|---|---|---|---|---|---|---|
| Position | WT | Mut | 32 | 33 | 35 | 36 | 37 | 38 | 39 | 40 | 41 | 42 | 43 | 45 | 46 | 47 | 48 | 49 | 50 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | | | | | | | | | | | | | | | I | | |
| 95 | N | C | | | | | | | | | | | | | | | | | |
| 97 | P | S | | | | | | | | | | | | | | | | | |
| 107 | S | D | | | D | | | | | | | D | | | | | | | |
| 123 | S | A | A | A | | A | A | | | | | | | A | | | | | |
| 132 | I | V | | | | | | | | | | | | | | | | | |
| 138 | E | A | | | | | | | | | | | | | | | | | |
| 145 | M | F | | | | | F | | | | | | | | | | | | |
| 151 | Y | A | | | | | | | | | | | | A | | A | A | A | A |
| 167 | V | I | I | I | I | | | I | | | | | | | | I | I | I | I |
| 180 | L | I | | | | I | I | | I | | | | | | | I | I | I | I |
| 194 | Y | S | | | | S | S | S | | | | | | | | | | | |
| 199 | A | S | S | S | | | | | S | | | | | | | | | | |
| 208 | K | H | | | | | | | | | | | | | | | | | |
| 209 | N | K | | | | | | | | | | | | | | | | | |
| 233 | S | N | | | | | | | | | | | | | | | | | |
| 236 | A | V | | | | | | | | | | | | | | | | | |
| 237 | R | N | | | | | | | | | | | | | | N | N | | | |
| 265 | P | S | | | | | | | | | | | | | | | | | |
| 267 | V | I | | | I | | | | | I | I | | | | | | | | |
| 273 | S | T | | | T | | | T | | | | | | | | | | | |
| 293 | G | A | A | A | | A | A | | | A | A | | | | | | | | |
| 299 | L | C | | | | | | | | | | | | | | | | | |
| 310 | I | K | | | | | | | | | | | K | | | | | | |
| 332 | K | R | | | | | | | | R | R | | | | | | | | |
| 337 | S | N | N | N | N | | | | | | | N | | | | | | | |
| 355 | P | S | | | | S | S | | | | | | S | | | | | | |
| 362 | L | M | | | | | | | | | | | | | | | | | |
| 363 | A | V | | | | | V | | | | | | | | | | | | |
| 369 | A | V | | | | | | | | | | | | | V | | | | |

Figure 16B

| Sequence changes | | | Variants | | | | | | | | | | | |
|---|---|---|---|---|---|---|---|---|---|---|---|---|---|---|
| Position | WT | Mut | N2 | N3 | N4 | N6 | N7 | N8 | N9 | N10 | N11 | N13 | N14 | N15 |
| 25 | Y | H | | | | | | | | | | | | |
| 34 | A | S | | | | | | | | | | | | |
| 48 | K | E | | | | | | | | | | | | |
| 50 | D | N | | | | | | | | | | | | |
| 55 | N | S | | | | | | | | | | | | |
| 63 | T | S | | | | | | | | | | | | |
| 88 | T | I | | | | | | | | | | | | |
| 95 | N | C | C | | | | | C | C | | | | C | |
| 97 | P | S | | S | | S | | | | | S | | | S |
| 107 | S | D | | | D | D | | | | | | D | | |
| 123 | S | A | | | | A | | | | | A | A | | |
| 132 | I | V | | | V | | | | V | | | | | |
| 138 | E | A | | A | | | A | | A | | | | A | |
| 145 | M | F | F | | | | | | F | | | | | F |
| 151 | Y | A | | | | | | | | | | | A | |
| 167 | V | I | I | | | | | | I | | | | I | |
| 180 | L | I | | | I | | I | | | | | I | | |
| 194 | Y | S | | S | | | | S | | | | S | | |
| 199 | A | S | S | | | | S | | | | | | S | |
| 208 | K | H | | | H | | H | | H | | | | H | |
| 209 | N | K | | | | | | | | | | | | |
| 233 | S | N | | | | | | | | | | | | |
| 236 | A | V | | V | | V | | | | V | | | | |
| 237 | R | N | N | | | | N | | | N | | | | N |
| 265 | P | S | | | S | | S | | | | S | | | |
| 267 | V | I | | I | | | | I | | | | | | |
| 273 | S | T | T | | | | | | T | | | | | T |
| 293 | G | A | | | | | | A | A | | | | | A |
| 299 | L | C | | | C | | | C | | C | | C | | |
| 310 | I | K | | | | K | | | | | K | | | K |
| 332 | K | R | | | | | | R | | R | | | | |
| 337 | S | N | | | N | | | | | | N | N | | |
| 355 | P | S | | | | | S | | | S | | | | |
| 362 | L | M | | | | | | | | | | | | |
| 363 | A | V | | | | | | | | | | | | |
| 369 | A | V | | | | | | | | | | | | |

Figure 16C

| Sequence changes | | | Variants | | | | | | | | | | | | | | | | |
|---|---|---|---|---|---|---|---|---|---|---|---|---|---|---|---|---|---|---|---|
| Position | WT | Mut | N16 | N17 | N18 | N19 | N20 | N21 | N22 | N23 | N24 | N25 | N26 | N27 | N28 | N30 | N33 | N40 | N43 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | | | | | | | | | | | | | | | | | |
| 95 | N | C | | | C | | | | | | C | C | | | | | | | |
| 97 | P | S | | S | | | | | | S | | | S | S | | | | | |
| 107 | S | D | | | D | | | | D | | | | | | | | D | | |
| 123 | S | A | | | | | A | A | | | | | | | | | A | | |
| 132 | I | V | V | | | | V | | V | | | | | | | | | | |
| 138 | E | A | | | | | A | | A | | | | | | A | | | | |
| 145 | M | F | | | F | | | | F | | | | | | | | F | F | F |
| 151 | Y | A | | A | | | | | | | A | | | | | | | | A |
| 167 | V | I | | | I | | | | | | I | | | | | | | | |
| 180 | L | I | | | I | | | | | I | | | | | | | | I | |
| 194 | Y | S | | | | | S | | | S | | | | S | | | | | |
| 199 | A | S | | S | | | | | | S | | | | | | | | | S |
| 208 | K | H | | | | | H | H | | | | | | | | | | | |
| 209 | N | K | | | | | | | | | | | | | | | | | |
| 233 | S | N | | | | | | | | | | | | | | | | | |
| 236 | A | V | V | V | | | | | V | | | | | | | V | | | |
| 237 | R | N | | | | N | | | | | N | | | | | | | | |
| 265 | P | S | S | | | S | | | | S | | | | | | | | | |
| 267 | V | I | I | | | I | | I | | | | | | | | | | I | |
| 273 | S | T | | | | T | | | | | T | | | | | | | | |
| 293 | G | A | | | A | | | | A | | | | | | | | | | |
| 299 | L | C | | C | | | | | C | | | | C | C | | | | | |
| 310 | I | K | | | K | | | | | K | | | | | | | | K | K |
| 332 | K | R | R | | | R | | | | | R | | | | | | | | R |
| 337 | S | N | | | | N | | | N | | | | | | | | | | |
| 355 | P | S | S | S | | | | | S | | | | | | | | | S | |
| 362 | L | M | | | | | | | | | | | | | | | | | |
| 363 | A | V | | | | | | | | | | | | | | | | | |
| 369 | A | V | | | | | | | | | | | | | | | | | |

Figure 16D

| Sequence changes | | | Variants | | | | | | | | | | | | | | | | |
|---|---|---|---|---|---|---|---|---|---|---|---|---|---|---|---|---|---|---|---|
| Position | WT | Mut | 47 | 48 | 49 | 50 | 51 | 52 | 53 | 54 | 55 | 56 | 57 | 58 | 59 | 60 | 61 | 62 | 63 |
| 25 | Y | H | | | | | | | | | | | | | | | | | |
| 34 | A | S | | | | | | | | | | | | | | | | | |
| 48 | K | E | | | | | | | | | | | | | | | | | |
| 50 | D | N | | | | | | | | | | | | | | | | | |
| 55 | N | S | | | | | | | | | | | | | | | | | |
| 63 | T | S | | | | | | | | | | | | | | | | | |
| 88 | T | I | I | | | | | | | | | | | | | | | | |
| 95 | N | C | | | | | | | | | | | | | | | | | |
| 97 | P | S | | | | | | | | | | | | | | | | | |
| 107 | S | D | | | | | | | | | | | | | | | | | |
| 123 | S | A | | | | | | | | | | | | | | | | | |
| 132 | I | V | | | | | | | | | | | | | | | | | |
| 138 | E | A | | | | | | | | | | | | | | | | | |
| 145 | M | F | | | | | | | | | | | | | | | | | |
| 151 | Y | A | A | A | A | A | | | | | | | | | | | | | |
| 167 | V | I | I | I | I | I | | | | | | | I | I | | I | I | I | |
| 180 | L | I | I | I | I | I | | | | | | | | | | | | | |
| 194 | Y | S | | | | | S | S | S | S | | | | | | | | | |
| 199 | A | S | | | | | S | S | S | S | | | | | | | | | |
| 208 | K | H | | | | | | | | | H | H | | | | | | | |
| 209 | N | K | | | | | | | | | K | | | | | | | | |
| 233 | S | N | | | | | | | | | | | N | | | | | | |
| 236 | A | V | | | | | | | | | | | | | | | | | |
| 237 | R | N | | | | | | | | | | | | | N | N | N | N | N |
| 265 | P | S | | | | | | | | | | | | | | | | | |
| 267 | V | I | | | | | I | I | I | I | I | I | I | I | I | I | | | I |
| 273 | S | T | | | | | | | | | | | | | | | | | |
| 293 | G | A | | | | | | | | | A | A | A | A | A | A | A | A | A |
| 299 | L | C | | | | | | | | | | | | | | | | | |
| 310 | I | K | | | | | | | | | | | | | | | | | |
| 332 | K | R | | | | | | | | | R | R | R | R | R | R | R | R | R |
| 337 | S | N | | | | | | | | | | N | N | | | | | | N |
| 355 | P | S | | | | | | | | | | | | | S | S | S | S | S |
| 362 | L | M | | | | | | | | | | | | | | | | | |
| 363 | A | V | | | | | | | | | | | | | | | | | |
| 369 | A | V | | | | | | | | | | | | | | | | | |

Figure 16E

| Sequence changes | | | Variants | | | | | | | | | |
|---|---|---|---|---|---|---|---|---|---|---|---|---|
| Position | WT | Mut | 65 | 66 | 67 | 69 | 70 | 71 | 72 | 73 | 74 |
| 25 | Y | H | | | | | | | | | |
| 34 | A | S | | | | | | | | | |
| 48 | K | E | | | | | | E | | | |
| 50 | D | N | | | | | | | | | |
| 55 | N | S | | | | | | | | | |
| 63 | T | S | | | | | | | S | | |
| 88 | T | I | | | | | | | | | |
| 95 | N | C | | | | | | | | | |
| 97 | P | S | | | | | | | | | |
| 107 | S | D | | | | | | | | | |
| 123 | S | A | | | | | | | | | |
| 132 | I | V | | | | | | | | | |
| 138 | E | A | | | | | | | | | |
| 145 | M | F | | | | | | | | | |
| 151 | Y | A | | | | | | | | | |
| 167 | V | I | I | I | | I | I | I | I | | |
| 180 | L | I | | | | | | | | | |
| 194 | Y | S | | | | | | | | | |
| 199 | A | S | | | | | | | | | |
| 208 | K | H | | | | | | H | H | H | H |
| 209 | N | K | | | | | | | | | |
| 233 | S | N | | | | | | | | | |
| 236 | A | V | | | | | | | | | |
| 237 | R | N | | | | | | N | N | | |
| 265 | P | S | | | | | | | | | |
| 267 | V | I | I | I | I | I | I | I | I | I | I |
| 273 | S | T | | | | T | T | | | | |
| 293 | G | A | A | A | | | | A | A | A | A |
| 299 | L | C | | | | | | | | | |
| 310 | I | K | | | | | | | | | |
| 332 | K | R | R | R | R | R | R | R | R | R | R |
| 337 | S | N | | | N | N | N | N | N | | |
| 355 | P | S | | | S | | | S | S | | |
| 362 | L | M | | | | | | | | | |
| 363 | A | V | | | | | | | | | |
| 369 | A | V | | | | | | | | V | V |

Figure 16F

| Variant | y1 | y2 | y4 | y5 | y6 | y7 |
|---|---|---|---|---|---|---|
| wt | 0.7526 | 0.8774 | 0.7477 | 1.1850 | 0.6604 | 2 |
| wt | 1.2316 | 1.0877 | 1.2523 | 0.8150 | 1.3396 | 2 |
| wt | 1.0822 | 0.9082 | 1.0894 | 1.0850 | 0.9829 | 2 |
| wt | 0.8904 | 1.1423 | 0.9106 | 0.9158 | 1.0171 | 2 |
| 10 | 0.0263 | 1.7208 | 0.1682 | -0.0125 | 0.0453 | 6 |
| 12 | 0.2211 | 0.1878 | 0.4486 | 0.2320 | 0.0415 | 2 |
| 13 | 0.0158 | 1.9119 | 0.2430 | -0.0376 | 0.0302 | 1 |
| 14 | 0.0158 | 2.3899 | 0.3364 | 0.0251 | 0.0377 | 6 |
| 15 | 1.6789 | 0.0135 | 2.3738 | 1.6176 | 0.0226 | |
| 15 | 1.3945 | 0.4917 | 1.6260 | 1.2690 | 0.6857 | |
| 19 | 0.9000 | 0.9476 | 1.0280 | 1.0219 | 0.8528 | 1 |
| 19 | 0.6932 | 1.0442 | 0.6667 | 0.8143 | 0.7238 | 1 |
| 20 | 1.2737 | 0.0593 | 1.5327 | 1.5172 | 0.0755 | 0 |
| 20 | 0.5507 | 0.0484 | 0.5203 | 0.6472 | 0.0267 | 0 |
| 21 | 0.1632 | 0.9251 | 0.0935 | 0.1881 | 0.1509 | 0 |
| 22 | 0.1947 | 0.3294 | 0.1869 | 0.2884 | 0.0642 | 2 |
| 23 | 1.8053 | 0.0878 | 3.0280 | 2.0000 | 0.1585 | 3 |
| 23 | 1.6932 | 0.0900 | 2.0163 | 1.6709 | 0.1524 | 3 |
| 24 | 0.0579 | 0.9777 | 0.0374 | 0.0627 | 0.0566 | 4 |
| 25 | 0.3421 | 1.4891 | 0.6168 | 0.4514 | 0.5094 | 6 |
| 26 | 0.0053 | 10.7547 | 0.2056 | 0.0094 | 0.0566 | 2 |
| 26 | 0.0521 | 0.4391 | 0.0650 | 0.0127 | 0.0229 | 2 |
| 27 | 0.3474 | 1.3905 | 0.3178 | 0.3793 | 0.4830 | 1 |
| 29 | 1.4263 | 0.0079 | 1.6822 | 1.6144 | 0.0113 | 4 |
| 29 | 1.2740 | 0.0150 | 1.7398 | 1.3431 | 0.0190 | 4 |
| 30 | 0.0316 | 0.9560 | 0.0935 | -0.0251 | 0.0302 | 8 |
| 31 | 0.0421 | 1.2547 | 0.1121 | 0.0502 | 0.0528 | 6 |
| 32 | 0.7316 | 1.2792 | 0.6916 | 1.0063 | 0.9358 | 4 |
| 33 | 0.3263 | 1.3530 | 0.5794 | 0.5235 | 0.4415 | 4 |
| 35 | 1.0737 | 0.1546 | 1.7009 | 1.4451 | 0.1660 | 1 |
| 36 | 0.0421 | 0.9858 | 0.2617 | 0.0752 | 0.0415 | 2 |
| 37 | 0.0316 | 0.9560 | 0.0187 | -0.0094 | 0.0302 | 2 |
| 38 | 0.0053 | 9.3208 | -0.0748 | -0.0157 | 0.0491 | 0 |
| 39 | 0.2158 | 1.2416 | 0.2430 | 0.3730 | 0.2679 | 1 |
| 40 | 1.6737 | 1.5444 | 2.5794 | 2.0031 | 2.5849 | 2 |
| 40 | 0.9342 | 1.4557 | 0.9593 | 0.9666 | 1.3600 | 2 |
| 41 | 0.9421 | 1.8906 | 1.1402 | 1.2539 | 1.7811 | 2 |
| 42 | 0.0474 | 1.3543 | 0.0935 | 0.0784 | 0.0642 | 0 |
| 43 | 0.4105 | 0.1287 | 0.5794 | 0.6364 | 0.0528 | 4 |
| 43 | 1.0466 | 0.0109 | 0.9919 | 0.6113 | 0.0114 | 4 |
| 46 | 0.4466 | 1.0919 | 0.3089 | 0.5245 | 0.4876 | 0.5 |
| 47 | 0.6575 | 0.7763 | 0.6016 | 0.8143 | 0.5105 | 7 |
| 48 | 0.9370 | 0.8253 | 0.9919 | 1.1168 | 0.7733 | 4 |
| 51 | 0.0219 | 1.5643 | -0.0488 | 0.0127 | 0.0343 | 1 |
| 55 | 1.0329 | 1.4901 | 1.0569 | 1.2986 | 1.5390 | 5 |

Figure 17A

| Variant | y1 | y2 | y4 | y5 | y6 | y7 |
|---|---|---|---|---|---|---|
| 56 | 1.3178 | 1.3124 | 1.5447 | 1.3198 | 1.7295 | 2 |
| 57 | 1.3123 | 0.9957 | 1.3496 | 1.2986 | 1.3067 | 3 |
| 58 | 0.9699 | 0.4635 | 0.8943 | 1.0237 | 0.4495 | 2 |
| 59 | 0.5260 | 0.0435 | 0.2927 | 0.5753 | 0.0229 | 0.5 |
| 60 | 0.5863 | 0.0325 | 0.3740 | 0.6578 | 0.0190 | 0.5 |
| 61 | 0.8548 | 0.0089 | 0.9268 | 0.9137 | 0.0076 | 0.5 |
| 62 | 0.3041 | 0.0752 | 0.2276 | 0.3574 | 0.0229 | 0.5 |
| 63 | 0.9370 | 0.0447 | 0.9919 | 0.9941 | 0.0419 | 0.5 |
| 65 | 0.3699 | 0.3193 | 0.0976 | 0.3955 | 0.1181 | 2 |
| 66 | 0.9096 | 0.5445 | 0.7480 | 0.9835 | 0.4952 | 2 |
| 67 | 0.2932 | 0.0520 | 0.1626 | 0.3194 | 0.0152 | 2 |
| 69 | 0.2301 | 0.2980 | 0.1951 | 0.1713 | 0.0686 | 2 |
| 70 | 0.5342 | 0.3066 | 0.2927 | 0.6028 | 0.1638 | 3 |
| 71 | 0.2411 | 0.3002 | 0.2114 | 0.2686 | 0.0724 | 0.5 |
| 72 | 0.4466 | 0.0427 | 0.2276 | 0.4611 | 0.0190 | 1 |
| 73 | 0.2219 | 0.7725 | 0.1138 | 0.2390 | 0.1714 | 4 |
| 74 | 0.7233 | 1.1113 | 0.4715 | 0.8164 | 0.8038 | 4 |

| Variation position | Casein hydrolysis (y7) | Thermal tolerance (y6) | AAPL-p-NA pH7.0 (y1) |
|---|---|---|---|
| 107 | D | S | S |
| 123 | A | S | S |
| 151 | A | Y | A |
| 167 | I | V | V |
| 180 | I | L | I |
| 194 | S | Y | Y |
| 199 | S | A | A |
| 208 | K | H | K |
| 267 | V | I | V |
| 273 | T | S | S |
| 293 | G | A | A |
| 332 | R | R | R |

Figure 21

Align RSV-19 heavy chain sequence with human germline ig heavy chain sequences from VBase using ClustalW.

A: *Substitutions set*
RULE 1a:
- Enumerate and classify the substitutions into 2 categories. (i) Substitutions found in the framework region and (ii) substitutions found in the CDR.
- Consider only these susbtitutions (ie RULE 1a is a filter)

B: *Substitutions from human germline sequences*
- Reconstruct phylogenetic tree RULE 1b:
- Calculate evolutionary proximity of the closest homolog in which each substitution occurs (EP)

RULE 2b:
- Calculate site heterogeneity at each substitution position (SH)

RULE 3b:
- Calculate entropy at each substitution position (SE)

RULE 4b:
- Calculate number of times a substitution is seen at a position in the set of homologs (SN)

C: *Substitutions from substitution matrices*
RULE 1c:
- Calculate favorability of each substitution using a PAM100 matrix (SM).

D: *Score*

$Score_{FW} = f(EP) \times f(SH) \times f(SE) \times f(SN) \times f(SM)$ $Score_{CDR} = f'(SE) \times f'(SN) \times f'(SM)$

Figure 23

```
Locus-1-03
Locus-1-08
Locus-1-18
Locus-1-24
Locus-1-45
Locus-1-46
Locus-1-58
Locus-1-69
Locus-1-e
Locus-1-f
Locus-2-26
Locus-2-70
Locus-3-09
Locus-3-11
Locus-3-13
Locus-3-15
Locus-3-20
Locus-3-21
Locus-3-23
Locus-3-30
Locus-3-30.3
Locus-3-30.5
Locus-3-33
Locus-3-43
Locus-3-48
Locus-3-49
Locus-3-53
Locus-3-64
Locus-3-66
Locus-3-72
Locus-3-73
Locus-3-74
Locus-3-d
Locus-4-28
Locus-4-30.1
Locus-4-30.2
Locus-4-30.4
Locus-4-31
Locus-4-34
Locus-4-39
Locus-4-59
Locus-4-61
Locus-4-b
Locus-5-a
```

Figure 24

| Substitutions | PC1 loads |
|---|---|
| 27G | 0.1001 |
| 29I | 0.1094 |
| 50I | 0.1204 |
| 66P | 0.1226 |
| 93A | 0.1229 |
| 5Q | 0.1259 |
| 9P | 0.126 |
| 15S | 0.13 |
| 19S | 0.13 |
| 65N | 0.13 |
| 83F | 0.13 |
| 84S | 0.13 |
| 86K | 0.13 |
| 42P | 0.1317 |
| 70S | 0.1392 |

Figure 28

```
Locus-1-03
Locus-1-08
Locus-1-18
Locus-1-24
Locus-1-45
Locus-1-46
Locus-1-58
Locus-1-69
Locus-1-e
Locus-1-f
Locus-2-26
Locus-2-70
Locus-3-09
Locus-3-11
Locus-3-13
Locus-3-15
Locus-3-20
Locus-3-21
Locus-3-23
Locus-3-30
Locus-3-30.3
Locus-3-30.5
Locus-3-33
Locus-3-43
Locus-3-48
Locus-3-49
Locus-3-53
Locus-3-64
Locus-3-66
Locus-3-72
Locus-3-73
Locus-3-74
Locus-3-d
Locus-4-28
Locus-4-30.1
Locus-4-30.2
Locus-4-30.4
Locus-4-31
Locus-4-34
Locus-4-39
Locus-4-59
Locus-4-61
Locus-4-b
Locus-5-a
```

Figure 29

| Substitutions | PC1 Loads |
|---|---|
| 82Q | -0.1507 |
| 68L | -0.1452 |
| 39I | -0.1421 |
| 70S | -0.1421 |
| 28S | -0.135 |
| 5Q | -0.1344 |
| 15S | -0.1344 |
| 19S | -0.1344 |
| 65N | -0.1344 |
| 83F | -0.1344 |
| 84S | -0.1344 |
| 86K | -0.1344 |
| 66P | -0.1303 |
| 50I | -0.1281 |
| 9P | -0.128 |

Figure 33

SEQUENCE LISTING

```
<160> NUMBER OF SEQ ID NOS: 3

<210> SEQ ID NO 1
<211> LENGTH: 20
<212> TYPE: PRT
<213> ORGANISM: E. Coli
<220> FEATURE:
<223> OTHER INFORMATION: E Coli Leader Peptide
```

```
<400> SEQUENCE: 1

Met Lys Lys Leu Leu Phe Ala Ile Pro Leu Val Val Pro Phe Tyr Ser
 1               5                  10                  15

His Ser Thr Met
            20

<210> SEQ ID NO 2
<211> LENGTH: 377
<212> TYPE: PRT
<213> ORGANISM: Tritirachium album Limber
<220> FEATURE:
<223> OTHER INFORMATION: Tritirachium album Limber proteinase K

<400> SEQUENCE: 2

Ala Pro Ala Val Glu Gln Arg Ser Glu Ala Pro Leu Ile Glu Ala
 1               5                  10                  15

Arg Gly Glu Met Val Ala Asn Lys Tyr Ile Val Lys Phe Lys Glu Gly
                20                  25                  30

Ser Ala Leu Ser Ala Leu Asp Ala Ala Met Glu Lys Ile Ser Gly Lys
            35                  40                  45

Pro Asp His Val Tyr Lys Asn Val Phe Ser Gly Phe Ala Ala Thr Leu
50                  55                  60

Asp Glu Asn Met Val Arg Val Leu Arg Ala His Pro Asp Val Glu Tyr
65                  70                  75                  80

Ile Glu Gln Asp Ala Val Val Thr Ile Asn Ala Ala Gln Thr Asn Ala
                85                  90                  95

Pro Trp Gly Leu Ala Arg Ile Ser Ser Thr Ser Pro Gly Thr Ser Thr
            100                 105                 110

Tyr Tyr Tyr Asp Glu Ser Ala Gly Gln Gly Ser Cys Val Tyr Val Ile
        115                 120                 125

Asp Thr Gly Ile Glu Ala Ser His Pro Glu Phe Glu Gly Arg Ala Gln
130                 135                 140

Met Val Lys Thr Tyr Tyr Tyr Ser Ser Arg Asp Gly Asn Gly His Gly
145                 150                 155                 160

Thr His Cys Ala Gly Thr Val Gly Ser Arg Thr Tyr Gly Val Ala Lys
                165                 170                 175

Lys Thr Gln Leu Phe Gly Val Lys Val Leu Asp Asp Asn Gly Ser Gly
            180                 185                 190

Gln Tyr Ser Thr Ile Ile Ala Gly Met Asp Phe Val Ala Ser Asp Lys
        195                 200                 205

Asn Asn Arg Asn Cys Pro Lys Gly Val Val Ala Ser Leu Ser Leu Gly
210                 215                 220

Gly Gly Tyr Ser Ser Ser Val Asn Ser Ala Ala Ala Arg Leu Gln Ser
225                 230                 235                 240

Ser Gly Val Met Val Ala Val Ala Ala Gly Asn Asn Asn Ala Asp Ala
                245                 250                 255

Arg Asn Tyr Ser Pro Ala Ser Glu Pro Ser Val Cys Thr Val Gly Ala
            260                 265                 270

Ser Asp Arg Tyr Asp Arg Arg Ser Ser Phe Ser Asn Tyr Gly Ser Val
        275                 280                 285

Leu Asp Ile Phe Gly Pro Gly Thr Ser Ile Leu Ser Thr Trp Ile Gly
290                 295                 300

Gly Ser Thr Arg Ser Ile Ser Gly Thr Ser Met Ala Thr Pro His Val
305                 310                 315                 320

Ala Gly Leu Ala Ala Tyr Leu Met Thr Leu Gly Lys Thr Thr Ala Ala
                325                 330                 335
```

```
Ser Ala Cys Arg Tyr Ile Ala Asp Thr Ala Asn Lys Gly Asp Leu Ser
            340                 345                 350

Asn Ile Pro Phe Gly Thr Val Asn Leu Leu Ala Tyr Asn Asn Tyr Gln
        355                 360                 365

Ala Val Asp His His His His His His
    370                 375

<210> SEQ ID NO 3
<211> LENGTH: 1193
<212> TYPE: DNA
<213> ORGANISM: Artificial Sequence
<220> FEATURE:
<223> OTHER INFORMATION: Artificial nucleic acid sequence encoding
      Tritirachium album Limber proteinase K

<400> SEQUENCE: 3
atgaaaaaac tgctgttcgc gattccgctg gtggtgccgt tctatagcca tagcaccatg      60
gcaccggccg ttgaacagcg ttctgaagca gctcctctga ttgaggcacg tggtgaaatg     120
gtagcaaaca agtacatcgt gaagttcaag gagggttctg ctctgtctgc tctggatgct     180
gctatggaaa agatctctgg caagcctgat cacgtctata agaacgtgtt cagcggtttc     240
gcagcaactc tggacgagaa catggtccgt gtactgcgtg ctcatccaga cgttgaatac     300
atcgaacagg acgctgtggt tactatcaac gcggcacaga ctaacgcacc ttggggtctg     360
gcacgtattt cttctacttc cccgggtacg tctacttact actacgacga gtctgccggt     420
caaggttctt gcgtttacgt gatcgatacg ggcatcgagg cttctcatcc tgagtttgaa     480
ggccgtgcac aaatggtgaa gacctactac tactcttccc gtgacggtaa tggtcacggt     540
actcattgcg caggtactgt tggtagccgt acctacggtg ttgctaagaa aacgcaactg     600
ttcggcgtta aagtgctgga cgacaacggt tctggtcagt actccaccat tatcgcgggt     660
atggatttcg tagcgagcga taaaaacaac cgcaactgcc cgaaaggtgt tgtggcttct     720
ctgtctctgg gtggtggtta ctcctcttct gttaacagcg cagctgcacg tctgcaatct     780
tccggtgtca tggtcgcagt agcagctggt aacaataacg ctgatgcacg caactactct     840
cctgctagcg agccttctgt ttgcaccgtg ggtgcatctg atcgttatga tcgtcgtagc     900
tccttcagca actatggttc cgtcctggat atcttcggcc ctggtacttc tatcctgtct     960
acctggattg gcggtagcac tcgttccatt tccggtacga gcatggctac tccacatgtt    1020
gctggtctgg cagcatacct gatgaccctg ggtaagacca ctgctgcatc cgcttgtcgt    1080
tacatcgcgg atactgcgaa caaaggcgat ctgtctaaca tcccgttcgg caccgttaat    1140
ctgctggcat acaacaacta tcaggctgtc gaccatcatc atcatcatca tag           1193
```

SYSTEMS AND METHODS FOR ANTIBODY ENGINEERING

CROSS-REFERENCE TO RELATED APPLICATIONS

This application claims benefit, under 35 U.S.C. §119(e), of U.S. Provisional Patent Application No. 60/491,815 filed on Aug. 1, 2003 which is incorporated herein, by reference, in its entirety. This application also claims benefit, under 35 U.S.C. §119(e), of U.S. Provisional Patent Application No. 60/536,357 filed on Jan. 14, 2004 which is incorporated herein, by reference, in its entirety. This application also claims benefit, under 35 U.S.C. §119(e), of U.S. Provisional Patent Application No. 60/536,862 filed on Jan. 15, 2004 which is incorporated herein, by reference, in its entirety. This Application is a continuation of U.S. patent application Ser. No. 10/566,954, filed Jan. 31, 2006 now abandoned which is a 35 U.S.C. §371 national stage filing of PCT/US04/24751, filed Jul. 30, 2004.

1. FIELD OF THE INVENTION

The field of this invention relates to computer systems and methods for designing sets of antibody variants and tools for relating the functional properties of such antibodies to their sequences. These relationships can then be used to determine the relationship between an antibody's sequence and commercially relevant properties of that antibody. Such sequence-function relationships may be used to design and synthesize commercially useful antibody compositions.

2. BACKGROUND OF THE INVENTION

Because of the immense size of sequence space, there is no effective way to systematically screen all possible permutations of an antibody for a desired property. To test each possible amino acid at each position in an antibody, rapidly leads to such a large number of molecules to be tested such that no available methods of synthesis or testing are feasible. Furthermore, most molecules generated in such a way would lack any measurable level of the desired property. Total sequence space is very large and the functional solutions in this space are sparsely distributed.

Two primary approaches have to date been used to identify antibody molecules with desired properties: mechanistic and empirical. There are significant limitations to both of these approaches. The mechanistic approach is often hampered by insufficient knowledge of the system to be improved, meaning either that considerable resources must be devoted to characterizing the system (for example by obtaining high quality protein crystal structures and relating these to the properties of interest), or that meaningful predictions cannot be made. In contrast, the empirical approach requires no mechanistic understanding, but relies upon direct measurements of an antibody's properties to select those variants that are improved. This strength is also its weakness; large numbers of variants cannot typically be tested under conditions that are identical to those of the final application. High throughput screens are widely used to provide surrogate measurements of the properties of interest, but these are often inadequate: binding of an antibody to an antigen is often an inadequate predictor of clinical or diagnostic function.

Empirical engineering of antibodies relies upon creating and testing sets of variants, then using this information to design and synthesize subsequent sets of variants that are enriched for components that contribute to the desired activity. A key limitation for any empirical antibody engineering is in developing a good assay for antibody function. The assay must measure antibody properties that are relevant to the final application, but must also be capable of testing a sufficient number of variants to identify what may be only a small fraction that are actually improved. The difficulty of creating such an assay is particularly relevant when optimizing antibodies for complex functions that are difficult to measure in high throughput. Examples include reduction of viral titer or the killing of tumor cells.

Large numbers of variants cannot typically be tested under conditions that are identical to those of the final application. High throughput screens are widely used to provide surrogate measurements of the properties of interest, but these are often inadequate. As examples, binding of an antibody to an antigen in a phage display assay can have little bearing on its ultimate usefulness as a therapeutic protein.

Limitations in current methods for searching through antibody sequences for specific commercially relevant functionalities creates a need in the art for methods that can design and synthesize small numbers of variants for functional testing and that can use the resulting sequence and functional information to design and synthesize small numbers of variants improved for a desired commercially useful activity. Limitations in current methods for choosing surrogate screens appropriate for empirical antibody engineering creates a need in the art for methods that can design and create small numbers of variants that can then be tested for specific commercially relevant functionalities.

3. SUMMARY OF THE INVENTION

The systems and methods described here apply novel computational biology and data mining techniques to important molecular design problems. In particular, novel ways to map antibody sequence space are described. Such maps are used to direct perturbations or modifications of the antibody sequences in order to perturb or modify the activity of the antibodies in a controlled fashion.

Methods are disclosed for biological engineering using the design and synthesis of a set of sequences containing designed substitutions that are statistically representative of a sequence space, and that contain a high fraction of antibodies possessing desired properties. In addition to its functionality, each antibody is also designed to maximize the information that the set of antibodies contains regarding the contribution of substitutions to the desired antibody properties and to the contributions resulting from interactions between substitutions. This in essence is a map of the sequence space that can also be used to design perturbations to modify the functionality of the antibody as desired.

The information used to create the substitutions that define the sequence space can be derived from one or more of (i) multiple sequence alignments, (ii) phylogenetic reconstructions of ancestral sequences, (iii) analysis of families or superfamilies of antibodies related by sequence, structure, function or partial function, (iv) analysis of monomer substitution probabilities within classes of antibody, (v) three dimensional structures (e.g., molecular models, X-ray crystallographic structures, nuclear magnetic resonance models, molecular dynamic simulations), (vi) immunogenic constraints, (vii) prior knowledge about the structure and/or function of the sequences upon which design of the antibody set is to be based, or (viii) any similar information pertaining to a related or homologous antibody. In one embodiment of the invention, this process is automated by use of an expert system that acquires domain knowledge and captures it is a knowledge database. This process can provide a score or rank order of substitutions to be incorporated, and a reasoning based on user specified constraints and domain specific data.

Generally speaking, the first step in the design and manufacture of the statistically representative sequence sets of this invention is the definition of the initial sequence space to be searched. This involves defining one or more reference sequences, identifying positions that are likely to tolerate alteration, and identifying substitutions at these positions that are likely to be acceptable or to produce desired changes in the properties of the antibody. All possible combinatorial strings of polymeric biological molecules define the total defined sequence space to be searched. Each substitution at each position is typically enumerated in silico and the acceptability defined computationally. Desirability or acceptability of each possible substitution is calculated according to one or more criteria. Such calculations can be performed by a computational system using the knowledge database, user specified constraints, and/or domain and antibody specific data.

The present invention also provides a more formal systematic method for selecting substitution positions. The use of a formal system involves quantitative scores and/or filters for assessing the favorability of substitution positions and the substitutions possible at those positions. Formalizing the system for substitution selection allows for the development of an automated system for antibody optimization or humanization. The parameters, filters and scores can be adjusted based on data from the scientific literature and data from experiments designed or interpreted by the automated system. By adjusting the scores and filters, substitutions that are predicted to be favorable can be aligned with those found experimentally to be favorable. Continuous refinement of these scores and filters based on experimental or computational data provides a way for the antibody optimization system to learn and improve. This formalization and learning capability are an aspect of the invention.

The second step in the design and manufacture of the statistically representative sequence sets of this invention is to define a subspace of the total sequence space to be searched in each iteration of the synthesis testing and correlating process. Typically the total allowed space matrix contains $10^5$-$10^{50}$ antibodies, many orders of magnitude larger than can be synthesized and measured under commercially relevant conditions. Such commercially relevant conditions are presently limited to numbers in the range of $10^1$-$10^3$. The number of antibody variants that can be synthesized and tested under appropriate conditions is defined by the availability of resources. The number of variant positions and the number of substitutions that can be tested at each of those positions is then calculated, such that each substitution will be present in a statistically representative fraction of the set of antibodies to be synthesized. Additionally, when using search methods like Tabu, Ant optimization or similar techniques, the space can be searched on a sequence by sequence basis by using a memory of the space that has been visited previously and the properties encountered.

Typical experimental design methods can introduce more changes in an antibody than the antibody can tolerate to remain functional. Adaptations of these methods, for example by using covering algorithms to reduce the total number of substitutions in each antibody variant, while maximizing the number of different combinations of pairs of substitutions is another aspect of the invention.

The third step in the design and manufacture of the statistically representative sequence sets (or sequence sets relevant for specific optimzation techniques) of this invention is to create a set of variant antibodies. This can be performed by synthesizing the antibody sequences defined and designed in the first two steps. The systematic design of such variants is one aspect of the present invention. The antibodies can be synthesized individually, or in a multiplexed set that is subsequently deconvoluted by sequencing or some other appropriate method. Alternatively, the antibodies can be created as a library of variants. Many methods have been described in the art for creating such libraries. See, for example, Stemmer (1994) Proc Natl Acad Sci USA 91: 10747-51; Stemmer (1994) Nature 370: 389-91; Crameri et al. (1996) Nat Med 2: 100-2; Crameri et al. (1998) Nature 391: 288-291; Ness et al. (1999) Nat Biotechnol 17: 893-896; Volkov et al. (1999) Nucleic Acids Res 27: e18; Volkov et al. (2000) Methods Enzymol 328: 447-56; Volkov et al. (2000) Methods Enzymol 328: 456-63; Coco et al. (2001) Nat Biotechnol 19: 354-9; Gibbs et al. (2001) Gene 271: 13-20; Ninkovic et al. (2001) Biotechniques 30: 530-4, 536; Coco et al. (2002) Nat Biotechnol 20: 1246-50; Ness et al. (2002) Nat Biotechnol 20: 1251-5; Aguinaldo et al. (2003) Methods Mol Biol 231: 105-10; Coco (2003) Methods Mol Biol 231: 111-27; and Sun et al. (2003) Biotechniques 34: 278-80, 282, 284 passim. Alternatively, specifically designed antibodies can be synthesized individually.

After synthesis, the designed set(s) of antibodies are characterized functionally to measure the properties of interest. This requires the development of an assay or surrogate assay faithful to the property or properties of ultimate interest and to test some members of the set of variants for more than one property, including the property of ultimate interest. Data mining techniques are then employed to characterize the functions of the variants and to derive a relationship between antibody sequences and properties. Optionally, the characterization data can be used to provide information in a subsequent iteration of the method, aiding in the design of a subsequent set of statistically representative variants that can be synthesized and tested to obtain a molecule with even more desirable properties. The data from additional iterations of this process can also be used to refine the data mining algorithms and models produced from the first set of data. The knowledge created about the sequence space can in turn be incorporated into the knowledge database for evaluating the substitutions in the light of this data and recalculating the scores or rank order of the substitutions. These processes are aspects of the present invention.

Additionally, combinations of the methods described herein can be made with other techniques such as directed evolution, DNA shuffling, family shuffling and/or systematic scanning approaches. These can be performed in any order and for any number of iterations to produce the products described herein. All such combinations are within the scope of the invention.

4. BRIEF DESCRIPTION OF THE DRAWINGS

FIG. 2 illustrates a flowchart for an antibody engineering method using integrated information sources to choose initial substitutions, and sequence-activity relationships to assess them in accordance with an embodiment of the present invention.

FIG. 6 illustrates the amino acid sequence of wild type proteinase K, reported by Gunkel et al. (1989) Eur J Biochem 179: 185-194, modified by (i) replacement of the fungal leader peptide with an $E.$ $coli$ leader peptide, amino acids −20 to −1 (SEQ ID No. 1), and (ii) addition of a histidine tag to the C terminus (amino acids 372-377), together with a ValAsp preceding the tag (amino acids 370 and 371) to accommodate cloning sites in the nucleic acid sequence.

FIG. 7 illustrates the nucleotide sequence of proteinase K optimized for expression in $E$ $coli$. The $E$ $coli$ leader peptide (amino acids −20 to −1 in FIG. 6) are encoded by nucleotides −60 to −1 in FIG. 7. The proteinase K sequence, beginning with Ala at amino acid 1 and ending with Ala at amino acid 369, is encoded by nucleotides 1-1107. The histidine tag, the two additional amino acids described in FIG. 6 and the termination codon are encoded by nucleotides 1108-1133.

FIG. 8 shows the accession numbers of 49 proteinase K homologs obtained by BLAST searching of Genbank.

Figure 9:
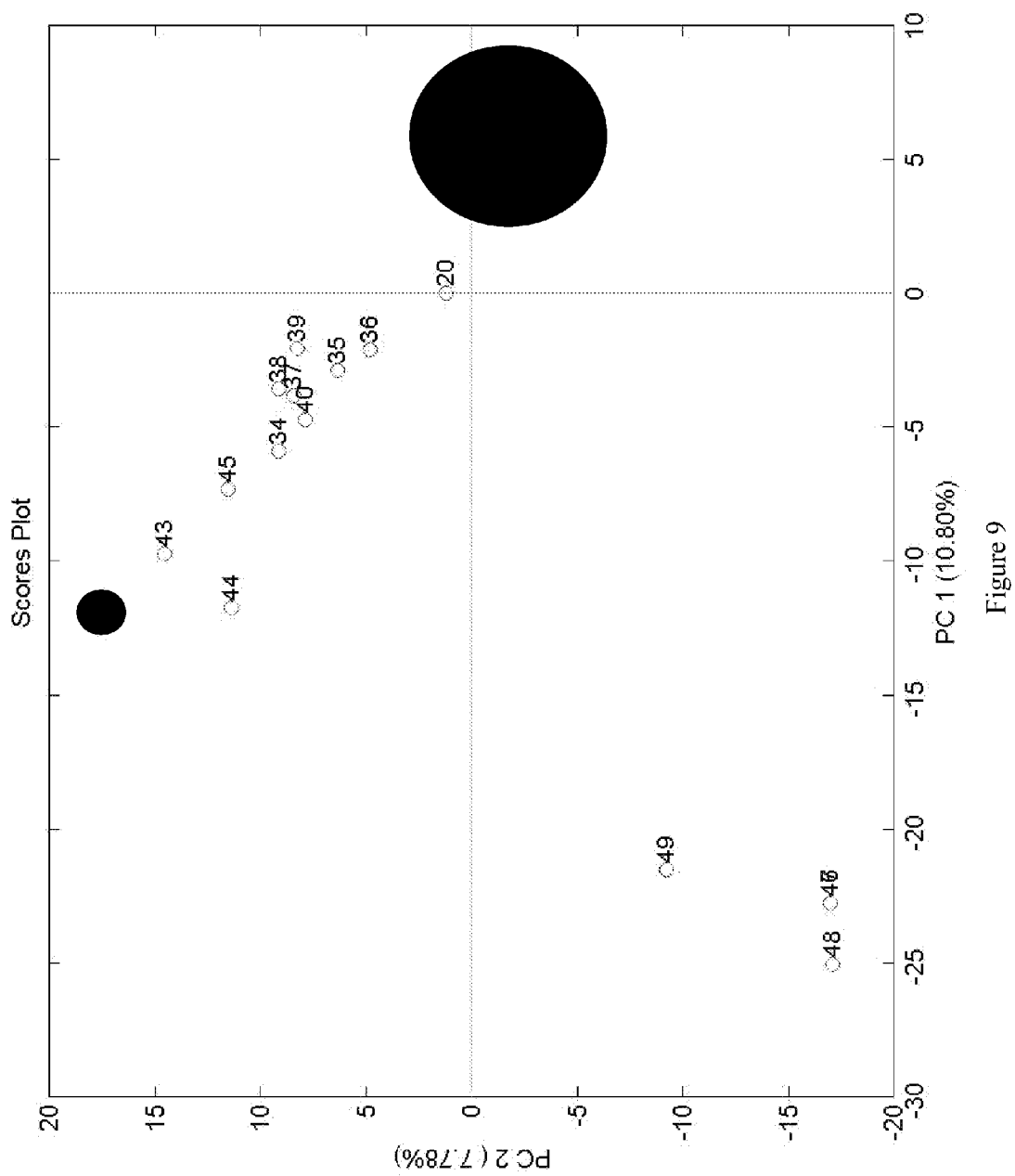

FIG. 9 illustrates a distribution of proteinase K homolog sequences (listed in FIG. 8) in the first two principal components of the sequence space. Sequences 46-49 are derived from thermostable organisms.

Figure 10:
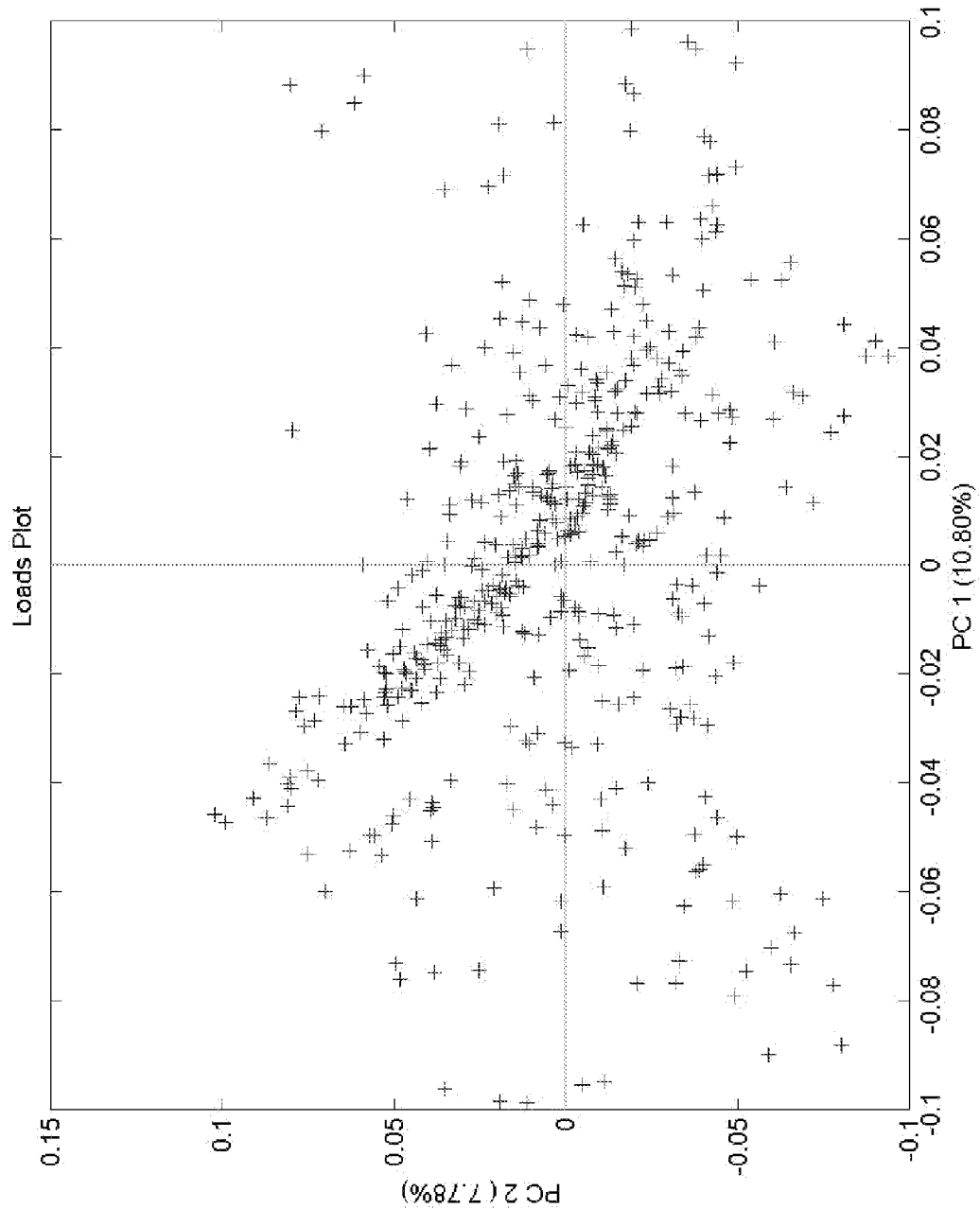

FIG. 10 illustrates a corresponding plot of all loads describing the influence of each variable on the sample distribution of FIG. 9

Figure 11:
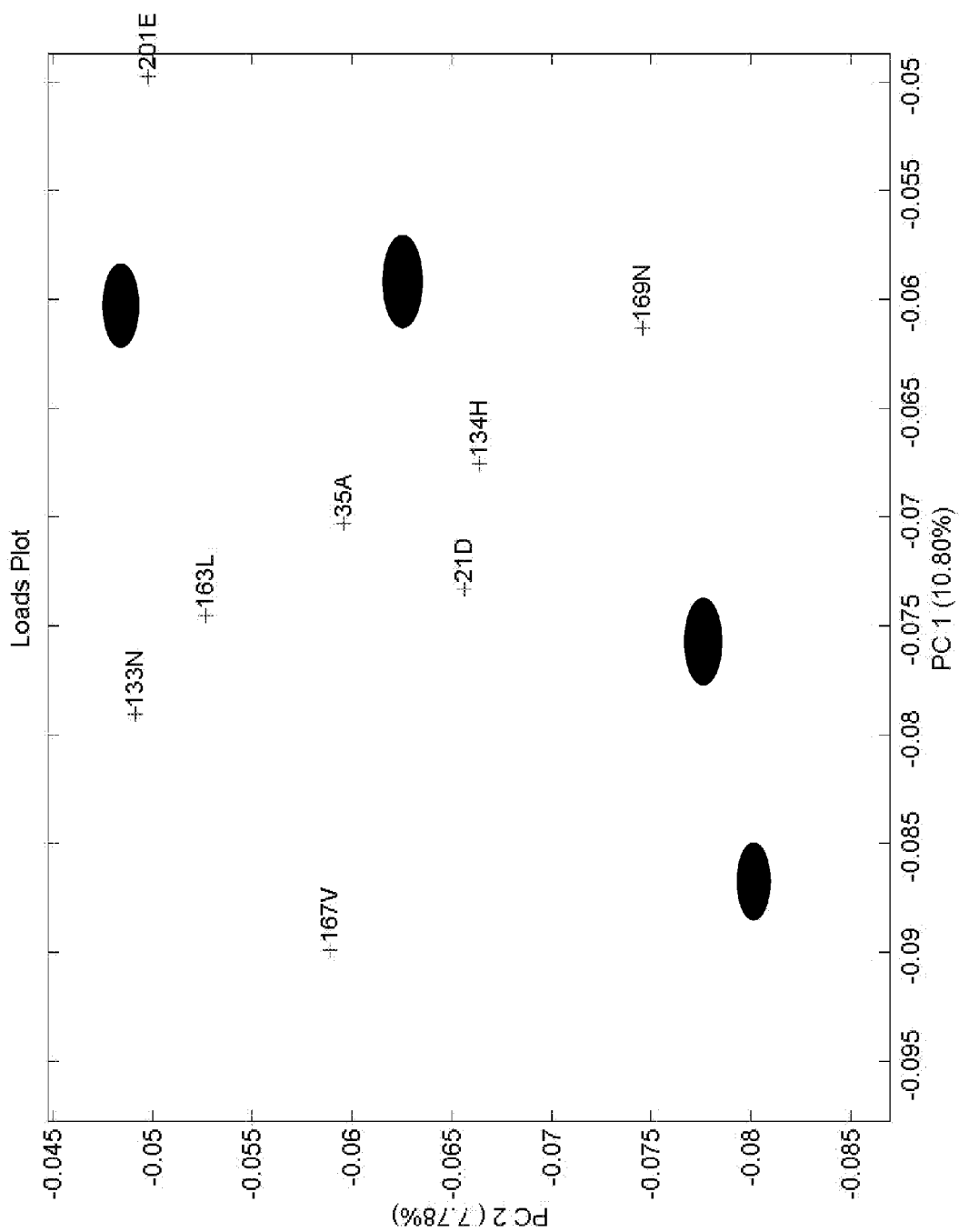

FIG. 11 provides magnified detail of the bottom left quadrant from FIG. 10.

FIG. 12 provides principal component analysis-derived loads for individual amino acids responsible for clustering of thermostable proteinase K homologs.

FIG. 13 illustrates sample output from an Expert System defining the 24 most highly scoring substitutions to be incorporated into a set of variants for initial mapping of proteinase K sequence-function space in accordance with an embodiment of the present invention.

FIG. 14 illustrates a first designed set of 24 variants for proteinase K. Each variant contains six substitutions from the wild type sequence. The numbers refer to the substitutions identified in FIG. 13.

FIG. 15 illustrates a second designed set of variants for proteinase K.

FIGS. 16A-16F illustrate amino acid changes in a set of synthesized proteinase K variants. Each column shows the changes from the wild type sequence present in one variant. A blank cell indicates the wild type sequence at that position. Amino acid numbering is shown in FIG. 6.

Figures 17B, 18:
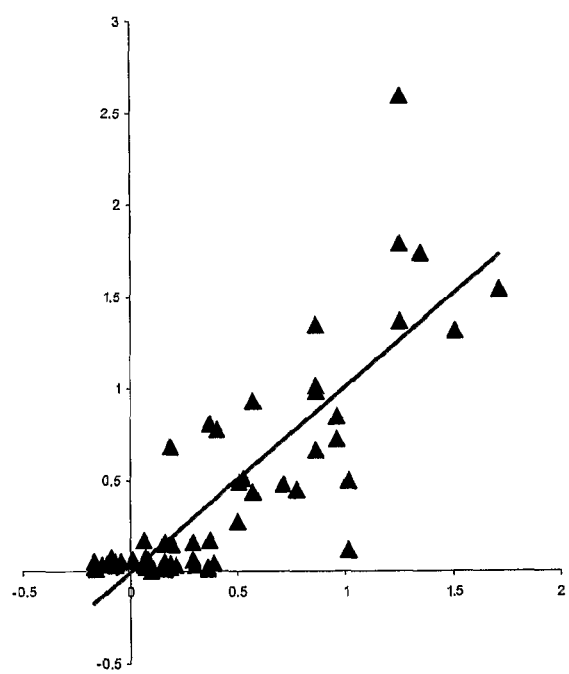

FIGS. 17A and 17B provide activity measurements of proteinase K variants. Proteinase K variants were assessed for six different hydrolytic activities. All activities are normalized to the average performance of the wild type proteinase K. In FIGS. 17A and 17B, y1: hydrolysis of a modified tetrapeptide, N-succinyl-Ala-Ala-Pro-Leu-p-nitroanilide (AAPL-p-NA) by purified proteinase K variants at pH 7.5; y2: thermostability ratio: activity after heat/activity without heat treatment, y6/y1; y4: hydrolysis of a modified tetrapeptide, N-succinyl-Ala-Ala-Pro-Leu-p-nitroanilide (AAPL-p-NA) by purified proteinase K variants at pH 4.5; y5: hydrolysis of a modified tetrapeptide, N-succinyl-Ala-Ala-Pro-Leu-p-nitroanilide (AAPL-p-NA) by purified proteinase K variants at pH 5.5; y6: hydrolysis of a modified tetrapeptide, N-succinyl-Ala-Ala-Pro-Leu-p-nitroanilide (AAPL-p-NA) at pH 7.5 by purified proteinase K variants which have been exposed to a heat treatment of 65° C. for 5 minutes; and y7: hydrolysis of casein measured as clearing zones, in an LB agar plate containing 2% skimmed milk, around a bacterial colony expressing the variant. Duplicate values indicate that a variant's activity was measured on two separate occasions.

FIG. 18 illustrates a comparison between values predicted and values measured for a protein sequence-activity model derived from sequences shown in FIG. 16 and activity data (y6) shown in FIG. 17. Measured activities of proteinase K variant activities towards AAPL-p-NA following a five minute 65° C. heat treatment on the y-axis are compared with those predicted by the model on the x-axis. All activities were measured at 37° C. and pH 7.0 using purified protein.

Figure 19:
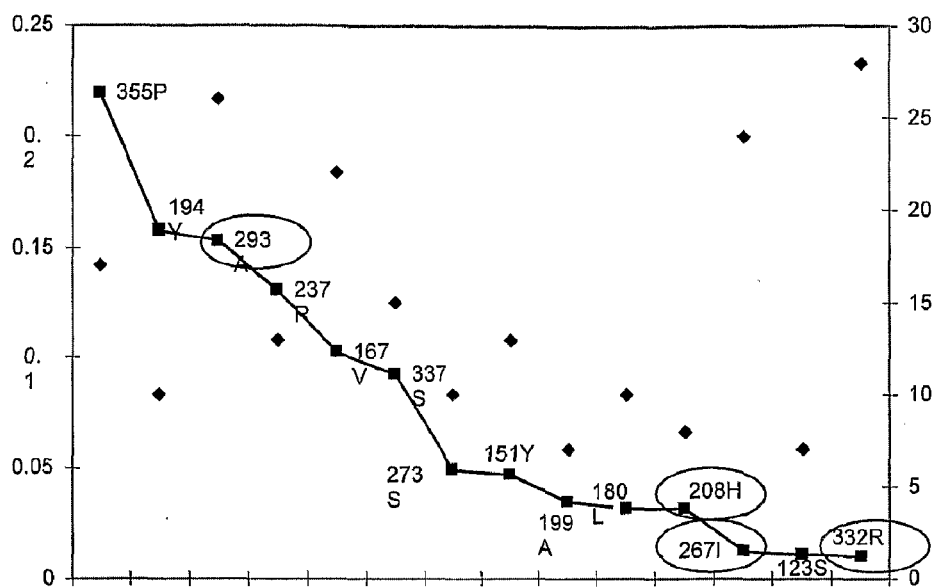

FIG. 19 illustrates the identification of amino acids contributing to a specific function from a sequence-activity model. Regression coefficients (squares, left axis) of variant amino acids were derived from the sequence-activity model relating the sequences of proteinase K sequence variants (with numbers lower than 49) to activity y6. The number of occurrences of each amino acid substitution are also shown (diamonds, right axis). Changes from the wild type sequence are circled.

Figure 20:
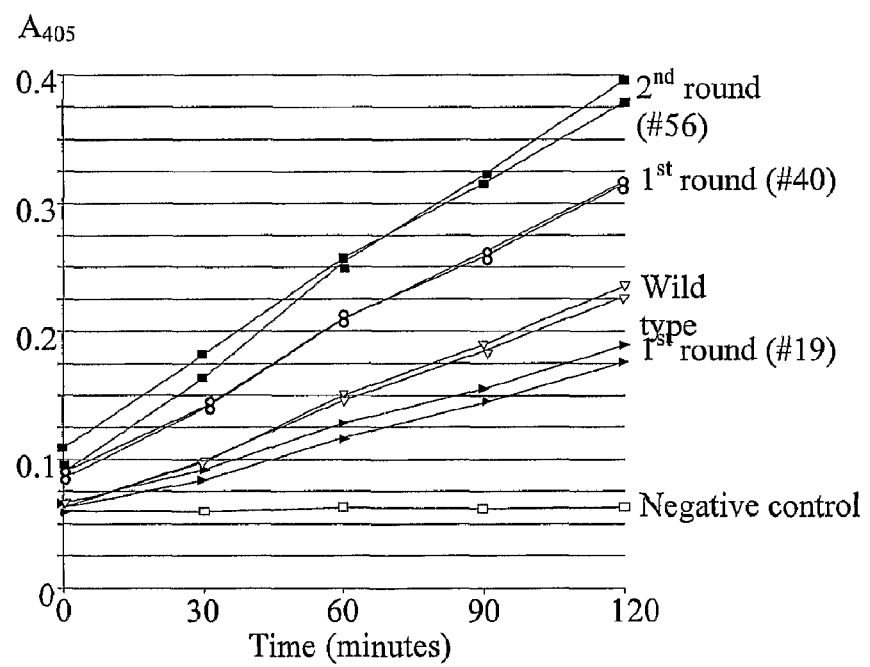

FIG. 20 illustrates the use of sequence-activity modeling to design a new variant with improved activity. Four amino acid substitutions were found to have positive regression coefficients in their contribution to activity following heat-treatment (y6). The variant test set contained one variant with one of these changes (#19) and one with three of these changes (#40). A new variant (#56) was synthesized to contain all four changes. The graph shows the activity of these variants towards AAPL-p-NA following five minute 65° C. heat treatment. Purified proteins were heated to 65° C. then incubated with AAPL-p-NA at pH 7.5. The reaction was followed by measuring the absorbance at 405 nm. Alterations from the wild type sequence are: #19, K208H (filled triangles); #S40, V267I, G293A, K332R (open circles); #56, K208H, V267I, G293A, K332R (filled squares).

FIG. 21 illustrates how different amino acids are important for different functions in proteinase K. Beneficial amino acid substitutions were calculated by sequence-activity modeling for three different proteinase K properties. Changes from the wild type sequence are underlined.

Figure 22:
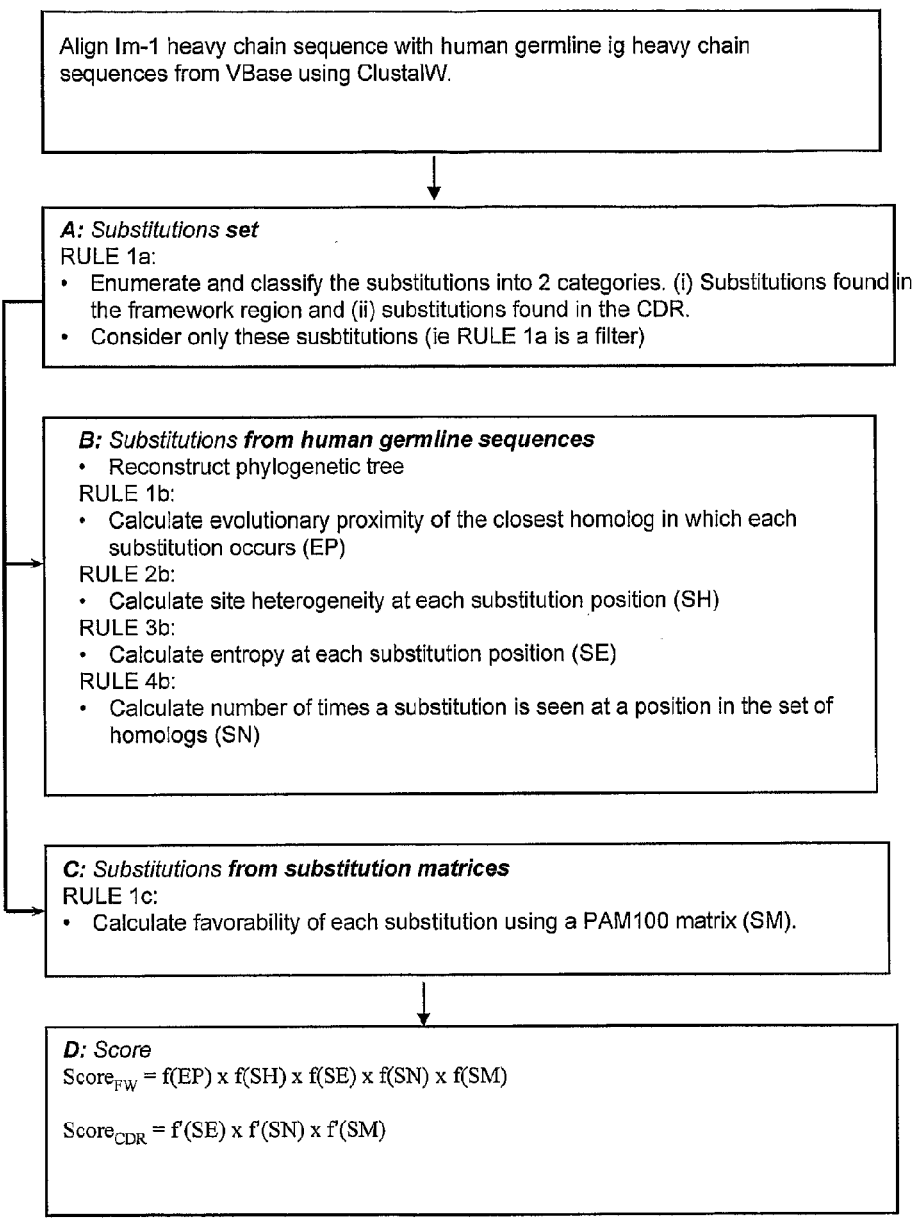
Figure 25:
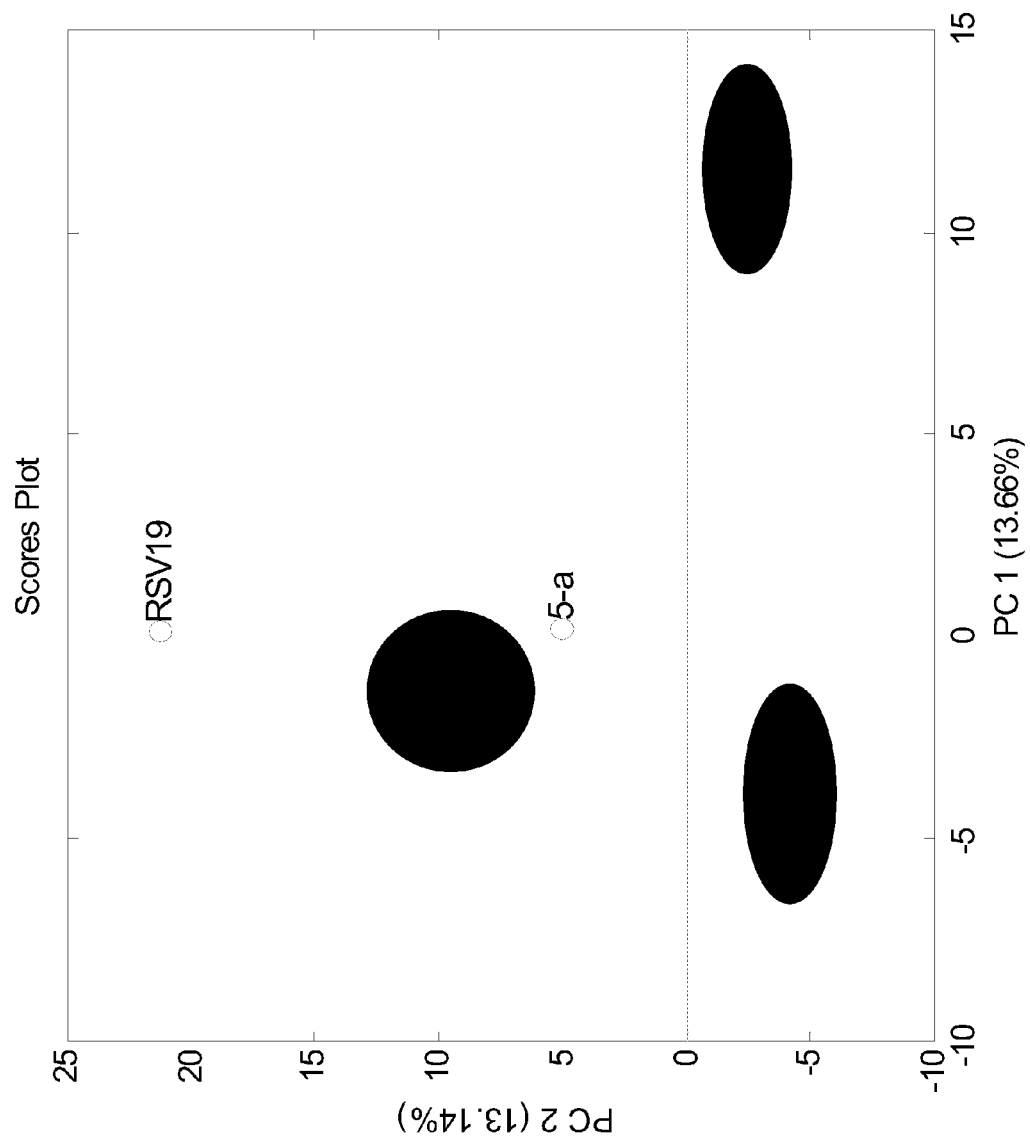
Figure 26:
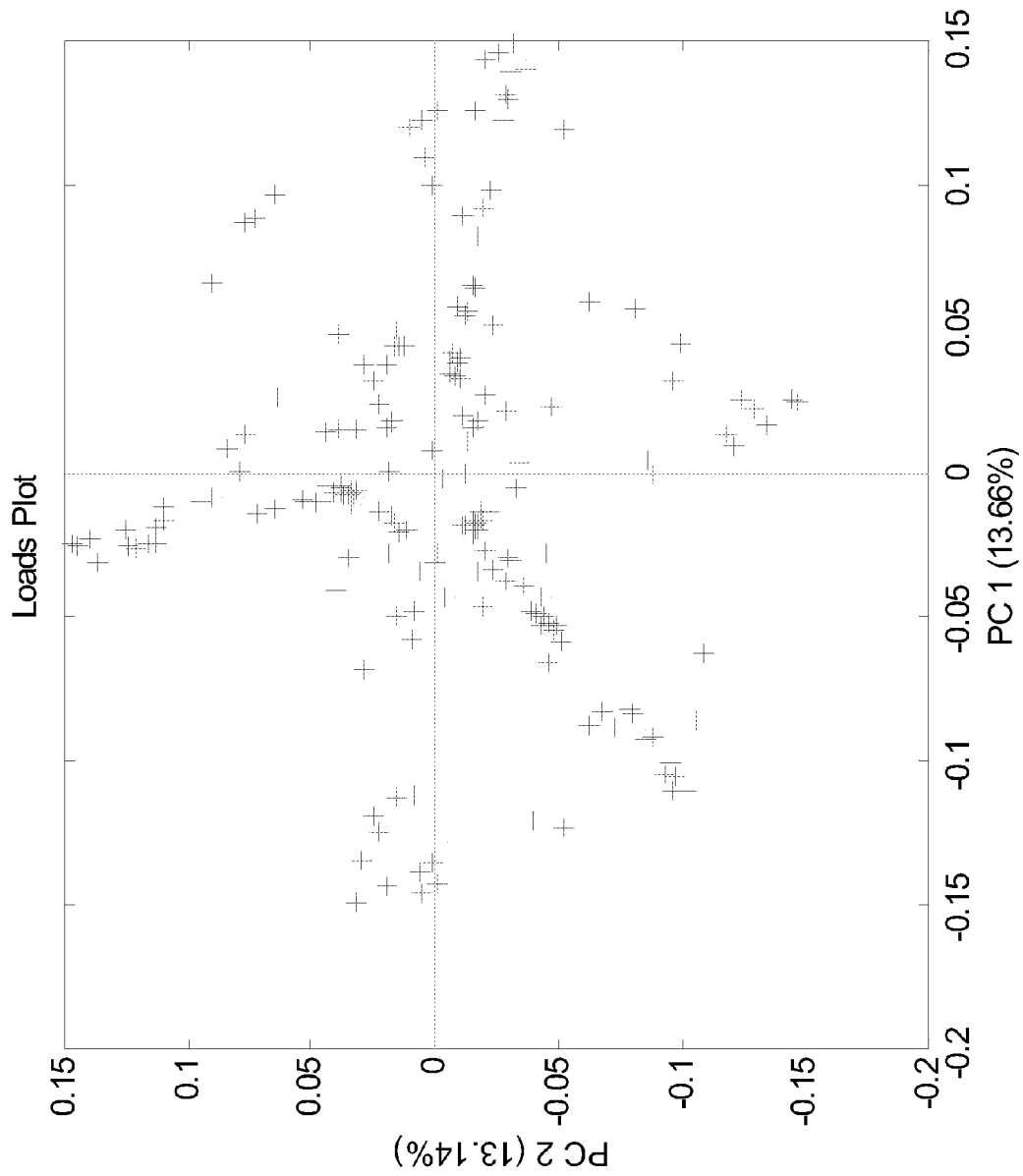
Figure 27:
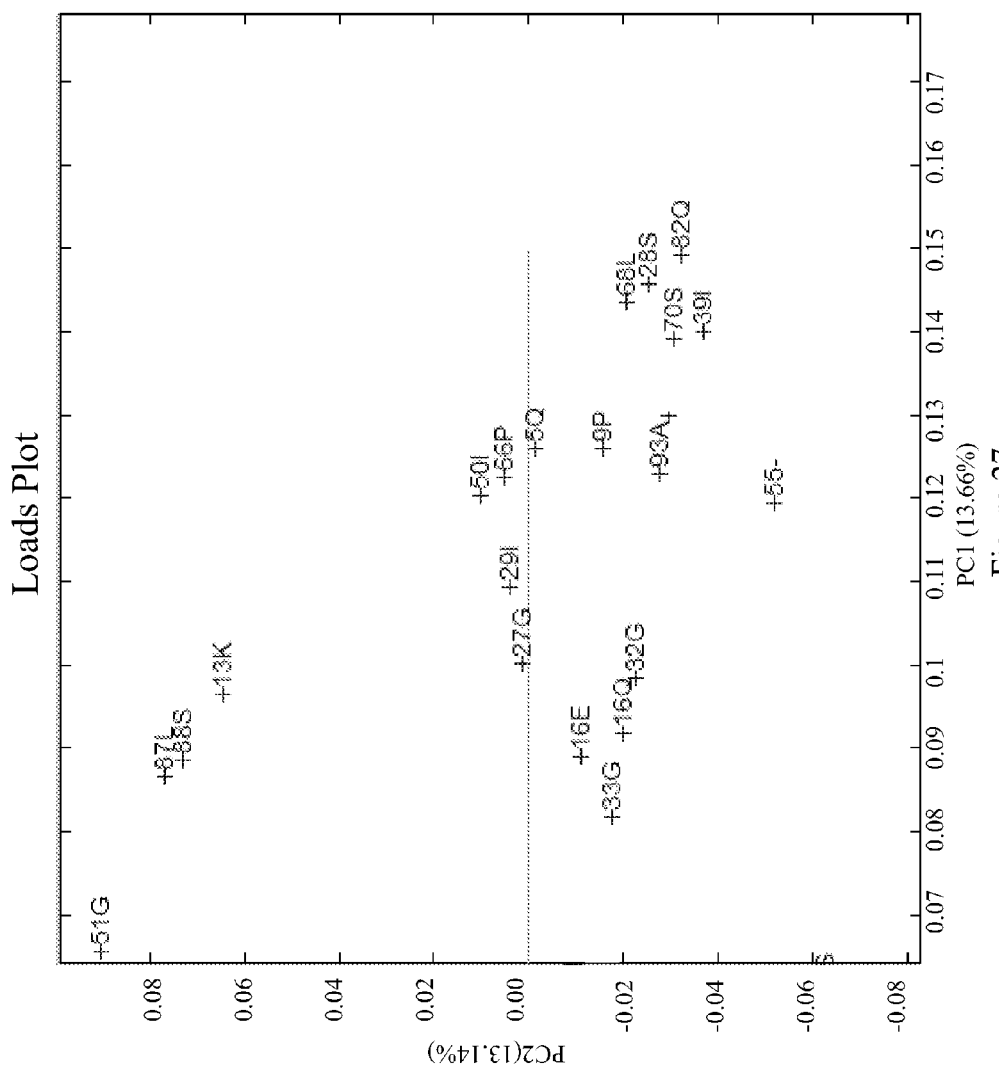

FIG. 22 is a schematic representation of a method for selecting amino acid substitutions for the optimization of antiviral activity of an antibody in accordance with an embodiment of the present invention.

FIG. 23 is a schematic representation of a method for selecting amino acid substitutions for the humanization of an antibody in accordance with an embodiment of the present invention.

FIG. 24 is a list of germline sequence locus identification numbers obtained from VBase (http://www.mrc-cpe.cam.ac.uk)

FIG. 25 illustrates a distribution of RSV antibody and antibody sequences (listed in FIG. 24) in the first two principal components of the sequence space.

FIG. 26 illustrates a corresponding plot of all loads describing the influence of each variable on the sample distribution of FIG. 25

FIG. 27 provides magnified detail of the right center from FIG. 26

FIG. 28 provides principal component analysis-derived loads for individual amino acids responsible for clustering of sequences in group containing the sequence 4-28.

FIG. 29 is a list of germline sequence locus identification numbers obtained from VBase (http://www.mrc-cpe.cam.ac.uk)

Figure 30:
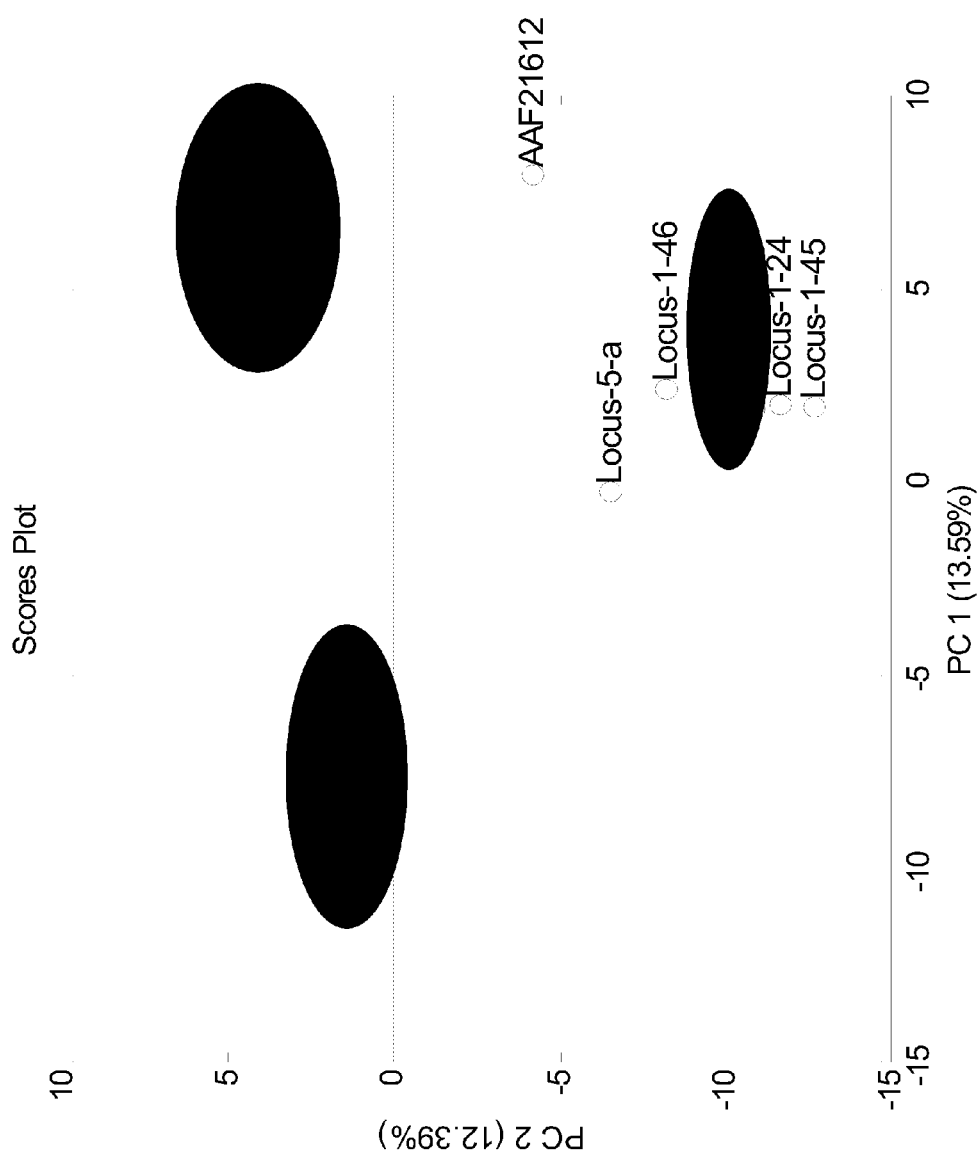

FIG. 30 illustrates a distribution of AAF21612 antibody and antibody sequences (listed in FIG. 29) in the first two principal components of the sequence space.

Figure 31:
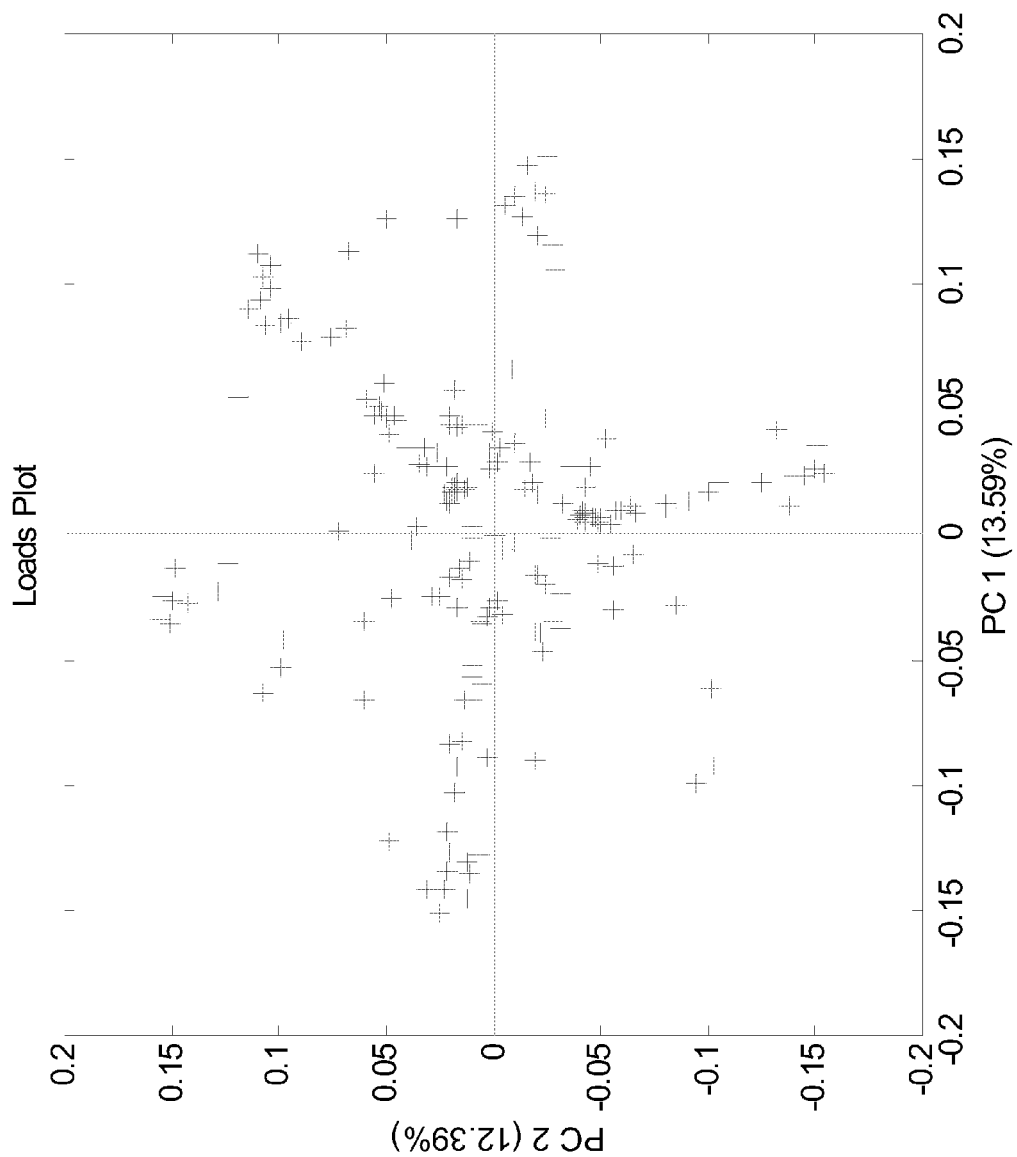

FIG. 31 illustrates a corresponding plot of all loads describing the influence of each variable on the sample distribution of FIG. 30

Figure 32:
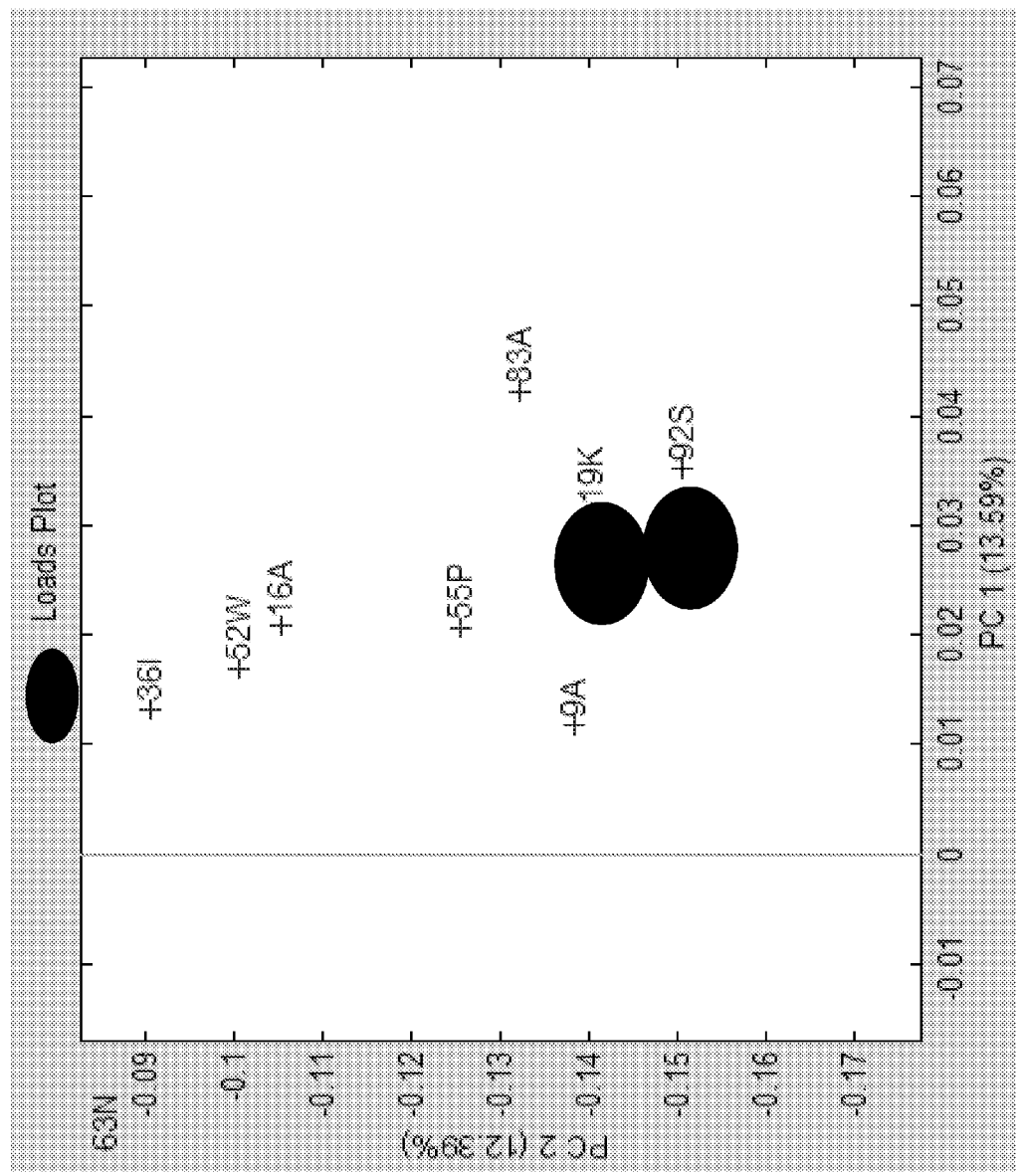

FIG. 32 provides magnified detail of the bottom center from FIG. 31

FIG. 33 provides principal component analysis-derived loads for individual amino acids responsible for clustering of sequences in group containing the sequence 5-a

5. DETAILED DESCRIPTION OF THE INVENTION

A general antibody humanization and/or maturation scheme is shown in FIG. 2. These steps found in FIG. 2 will be briefly introduced here and described in more detail below.

Step 01. An antibody or a plurality of antibodies, that partially or fully achieves the desired property (e.g., function, being humanized and/or matured) is used as a starting point (step 01).

Step 02. Substitutions to a sequence of step 01 are identified using a combination of changes to the antibody sequence. Such changes are either in monomer identity or in monomer physico-chemical properties. These changes span either the CDR and/or the framework region of heavy chain and/or the light chain of the antibody. For example, consider the case in which the heavy chain of the antibody is being humanized. In step 02, a determination can be made that the $21^{st}$ and $49^{th}$ positions of the heavy chain (based on the kabat numbering scheme) can be changed. Moreover, in some embodiments, a determination is made as to which substitutions can be made at such positions in step 02. For instance, step 02 may not only determine that the $21^{st}$ position of the antibody can be changed, but may also determine that this position should be changed to a glycine, alanine, or leucine.

In typical embodiments, several independent rules are used to determine which positions of the antibodies of step 01 can be changed. Each such rule scores or ranks individual substitutions based on different methods and based on the nature of optimization (i.e) humanization or maturation. Representative rules include, but are not limited to, rules based on (i) changes found in functional, structural or sequence classes, (ii) changes predicted to be favorable using substitution matrices, (iii) changes predicted using evolutionary analysis of the antibody structural and sequence classes, (iv) changes seen in random mutagenesis screening, (v) changes predicted by structural modeling, (vi) changes proposed by an expert on the antibody and (vii) changes predicted to be favorable using structural information (vii) changes derived from comparing the framework region of the antibodies with human germline sequences (viii) changes derived from comparing the framework regions of human antibodies (ix) changes derived from substitution matrices constructed from the positional frequencies of amino acids in the CDR regions of all antibodies. Any number of rules can be applied to the one or more antibodies of step 01.

In some embodiments of the present invention, each independent rule assigns a score for each possible substitution position (e.g. residue) in the antibody of step 01. The scores generated by each of the rules are then combined by methods and/or filters to determine the positions in the antibody that are suitable for change. These scores generated by each of the rules are specific to nature of the optimization process, (i.e) scores are independently derived for humanization of antibodies and for maturation of antibodies.

Step 03. Step 02 identified a set of candidate substitution positions in the antibodies of step 01. In step 03, a variant set incorporating such candidate substitutions is designed such that each candidate substitution is tested in combination with many different other candidate substitutions in order to cover the possible search space as evenly as possible (step 03).

To illustrate, consider the case in which the antibody of step 01 is a murine antibody and the $2^{nd}$, $5^{th}$, and $15^{th}$ kabat positions of the heavy chain have been identified as candidate substitution positions in step 03. Assuming that each of these three positions can be independently substituted with any of the twenty naturally occurring amino acids, there are $20^3-1$ different variant antibodies that could be constructed. In some instances, step 02 will constrain the types of amino acids that can be substituted at these positions based on the rules described above. Nevertheless, the full antibody sequence space proposed in step 02 even after filtering can be large. Step 03 seeks to minimize the number of variants that are constructed in order to evenly search and sample this large sequence space.

Step 04. Variant antibodies selected in step 03 are individually synthesized and tested for function(s) of interest in step 04. When the variant antibodies are synthesized individually it is easier to keep the number of changes and the number of variants synthesized and tested in each iteration of the process relatively small. In some embodiments, between 5 and 200, more preferably between 10 and 100, and even more preferably between 15 and 50 variants are synthesized and tested in step 04. By minimizing the number of variants synthesized and tested, relatively inaccurate high throughput assay screens can be avoided in step 04.

Step 05. Various machine-learning methods or other datamining techniques are used to model the relationship between the sequences and activities of the variant antibodies in step 05.

Step 06. The assessments of the affect of each substitution upon the properties (functions) of the antibodies by each model tested in step 05 are combined in step 06.

Step 07. The assessments of the affect of each substitution upon the properties (functions) of the antibodies by each tested model that was made in step 06 is used in step 07 to design a new set of variant antibodies for synthesis and testing Repeating steps 04-07. Steps 04 through 07 are repeated a number of times. Each iteration of steps 04-07 seeks to design a set of high scoring and diverse antibodies for synthesis and functional testing. Each new set of measurements from an iteration of step 04 is used to refine the sequence-activity model until an end point is reach, at which point the method progresses to step 08.

Step 08. The performance of the methods used to select substitution positions in step 02 and to model the sequence-activity relationships in instances of step 05 are assessed by analyzing the sequences of the best performing variants. In general, the best performing variants are any variants in any iteration of the cycle defined by steps 04-07 that score best in one or more functional assays for the target antibody. Step 08 provides a method for tuning the adjustable parameters of the system. Once these parameters have been adjusted, steps 02 through 07, including multiple iterations of the cycle defined by steps 04-07, are repeated. Advantageously, one of the adjustable parameters of the system is the individual weights for each of the methods applied in step 02. For example, those step 02 methods that were good at identifying substitution positions associated with high scoring antibody variants are up-weighted in the next instance of steps 02 through 07. The modification of weights applied to methods in step 02 based on the results of cycles of steps 04-07 allows the system to learn from previous results thereby improving the accuracy with which the system can identify beneficial substitutions (in step 02) and assess the contribution of substitutions to antibody activity (in steps 05 and 06).

5.1 Expert Systems for Defining a Sequence Space

Figure 1:
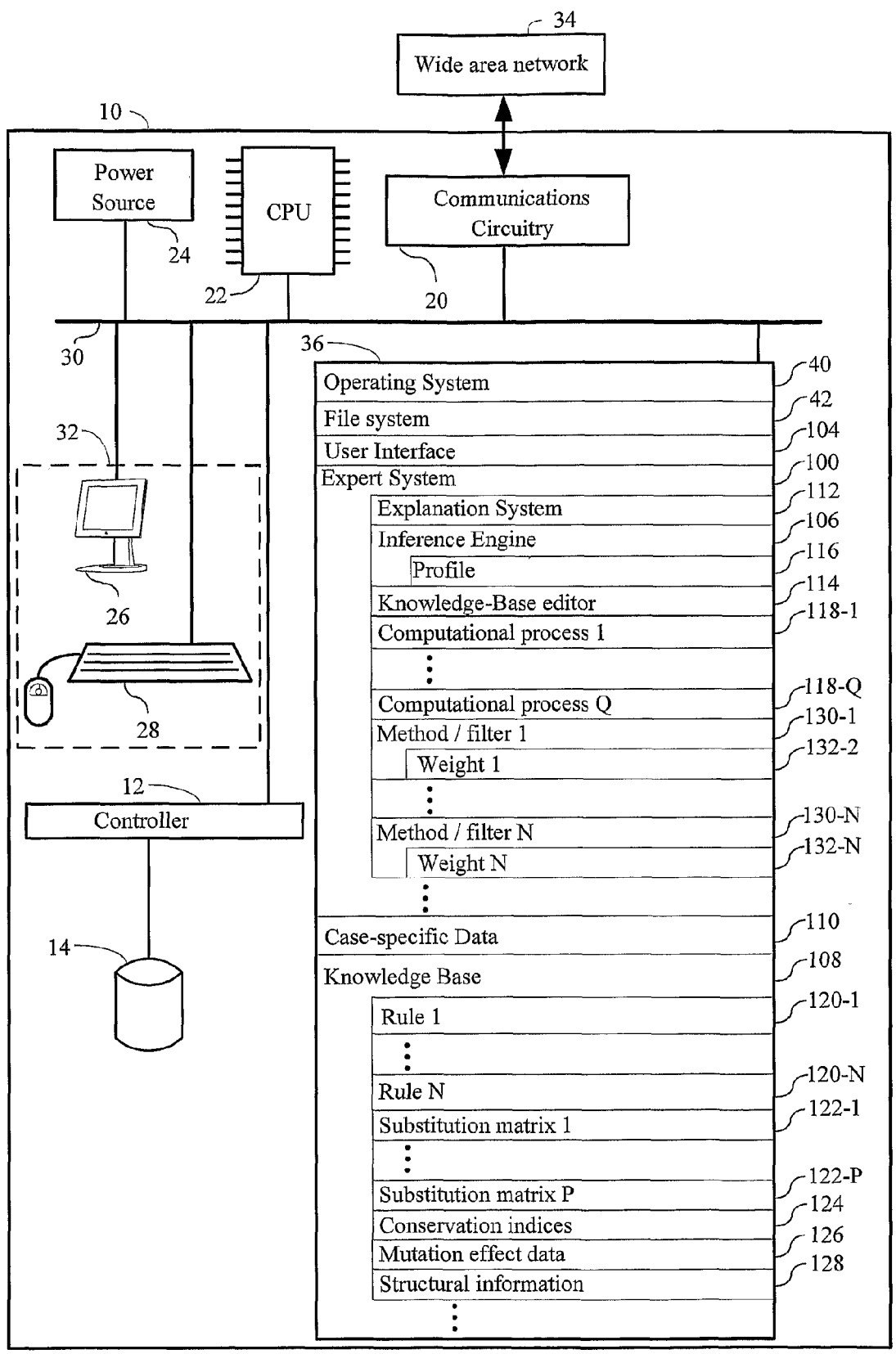
FIG. 1 illustrates an overview of the architecture of an Expert System in accordance with an embodiment of the present invention.

FIG. 1 details an exemplary system that supports the functionality described above. The system is preferably a computer system 10 having:

- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 or other output device;
- a network interface card 20 for connecting to any wired or wireless communication network 34 (e.g., a wide area network such as the Internet);
- an internal bus 30 for interconnecting the aforementioned elements of the system; and
- a power source 24 to power the aforementioned elements.

Operation of computer 10 is controlled primarily by operating system 40, which is executed by central processing unit 22. Operating system 40 can be stored in system memory 36. In a typical implementation, system memory 36 includes:

- operating system 40;
- file system 42 for controlling access to the various files and data structures used by the present invention;
- a user interface 104;
- an expert system 100;
- case-specific data 110; and
- knowledge base 108.

As illustrated in FIG. 1, computer 10 comprises case-specific data 110 and knowledge base 108. Case-specific data 110 and knowledge base 108 each independently comprise any form of data storage system including, but not limited to, a flat file, a relational database (SQL), and an on-line analytical processing (OLAP) database (MDX and/or variants thereof). In some specific embodiments, case-specific data 110 and/or knowledge base 108 is a hierarchical OLAP cube. In some specific embodiments, case-specific data 110 and/or knowledge base 108 comprises a star schema that is not stored as a cube but has dimension tables that define hierarchy. In some embodiments, case-specific data 110 and/or knowledge base 108 is respectively a single database. In other embodiments, case-specific data 110 and/or knowledge base 108 in fact comprises a plurality of databases that may or may not all be hosted by the same computer 10. In such embodiments, some component databases of case-specific data 110 and/or knowledge base 108 are stored on one or more computer systems that are not illustrated by FIG. 1 but that are addressable by wide area network 34.

It will be appreciated that many of the modules illustrated in FIG. 1 can be located on one or more remote computers. For example, some embodiments of the present application are accessible in web service-type implementations. In such embodiments, user interface module 104 and other modules can reside on a client computer that is in communication with computer 10 via network 34. In some embodiments, for example, user interface 104 can be an interactive web page.

In some embodiments, the case-specific data 110 and/or knowledge base 108 and modules (e.g. modules 100, 104, 112, 106, 116, 114, 118, 130, 132) illustrated in FIG. 1 are on a single computer (computer 10) and in other embodiments such data is hosted by several computers (not shown). Any arrangement of case-specific data 110 and knowledge base 108 and the modules illustrated in FIG. 1 on one or more computers is within the scope of the present invention so long as these components are addressable with respect to each other across network 34 or by other electronic means. Thus, the present invention fully encompasses a broad array of computer systems.

Now that an overview of a computer system and the data structures stored in such a computer system has been presented, more details on the inventive data structures and software modules of the present invention will be described.

Expert system 100 is a software module that includes stored knowledge and solves problems in a specific field (for example antibody engineering) by emulating some of the decision processes of a human expert(s). The first set of algorithms that chooses the substitutions and the sequence space to explore for antibody engineering (steps 02 and 03 of FIG. 2) may require expertise in the domains of polynucleotide structure and function, antibody structure and function, protein structural analysis and interpretation, protein structure and function, protein and nucleic acid phylogeny and evolution, chemical and enzymatic mechanisms, bioinformatics and related fields. Expert system 100 applies the knowledge to problems specified by a user who is not necessarily an expert in the domain(s). This invention describes the construction and use of expert system 100 for selecting substitutions useful for mapping and engineering antibody functions.

Two functions expert system 100 provides in order to define a sequence space to search are (i) the identification of one or more positions in the antibody at which substitution is likely to be accepted and where at least some substitutions, insertions, deletions or modifications are likely to result in a functional antibody and (ii) the identification of residues or modifications that are likely to result in a functional antibody when used to substitute or insert at each of the one or more positions identified in (i). An additional or alternative purpose of expert system 100 is the identification of residues or modifications that are likely to affect the desired properties or functions of the antibody. These functions are represented as step 02 in FIG. 2.

One aspect of this invention is the use of methods to identify positions that can be varied, then to synthesize a set of antibody variants containing these substitutions and to test the antibodies for one or more property or function, with the aim of deriving relationships between antibody sequence and function.

A user can interact with expert system 100 using user interface 104. In some embodiments, user interface 104 comprises menus, natural language or any other style of interaction. Expert system 100 uses inference engine 106 to reason using the expert knowledge stored in knowledge database 108 together with case-specific data 110 relating to the specific antibody or class of antibodies to be mapped and/or engineered. Case-specific data 110 can be acquired as input from the user of expert system 100, presented in knowledge base 108, or acquired from case-specific knowledge generated by the results of experimentation and the analysis facilitated by sequence-activity correlating methods of this invention described in further detail below. These sequence-activity correlating methods are performed in step 05 of FIG. 2, for example. The data from these sequence-activity correlating methods can additionally be used to add to or alter the information contained within knowledge base 108.

Expert knowledge will typically be stored in knowledge base 108 in the form of a set of rules 120. An exemplary rule 120 is:

```
IF (an antibody protein has known variants that possess some activity)
THEN {
        assign probabilities for incorporating the variant residues
        based on their occurrence in some set of other naturally
        occurring antibodies and/or synthetically derived antibodies
        using a substitution matrix to determine the likelihood of such
        a substitution occurring in nature
}
```

Another exemplary rule 120 is:

```
IF (desired activity is binding affinity)
THEN {
      Change weights used to score/ rank the substitutions found in known
      antibody classes that bind to the desired target
}
```

Figure 4:
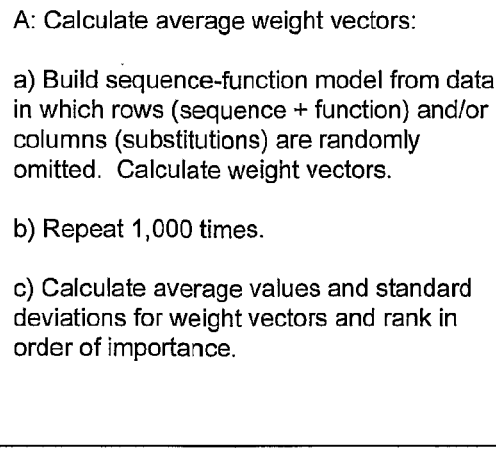
FIG. 4 illustrates a method for calculation of weights (e.g. contributions to activity) for each amino acid substitution in accordance with an embodiment of the present invention.
Figure 5:
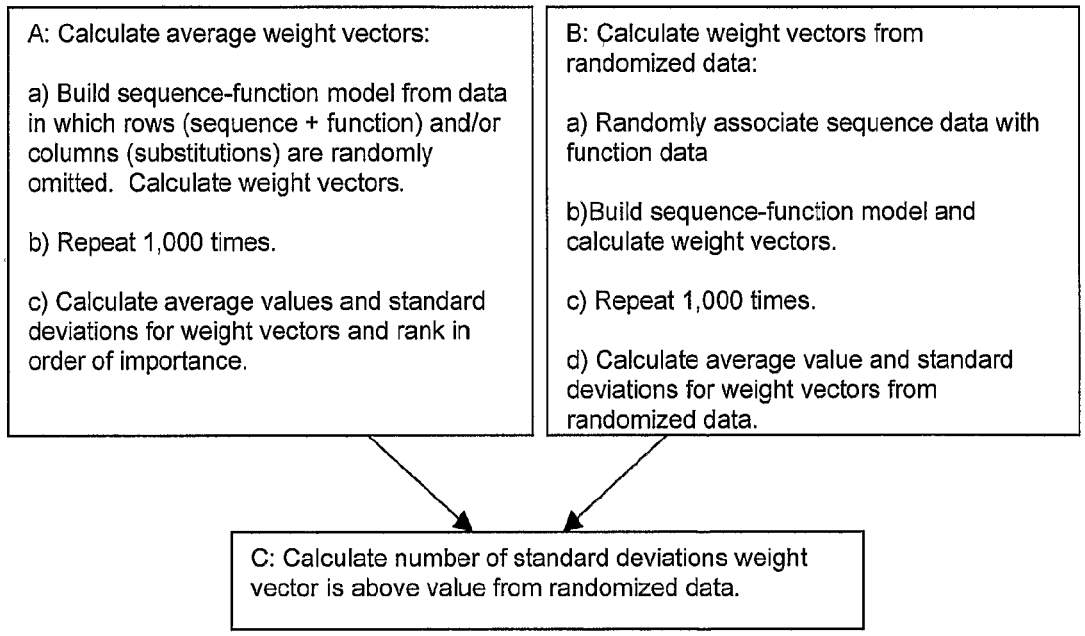
FIG. 5 illustrates a method for calculation of weights (e.g., contributions to activity) for each substitution in accordance with an embodiment of the present invention. This method provides information about the confidence of each weight by comparison with weights obtained from randomized data.

Additional examples of rules 120 are each of the filters described in FIGS. 4 and 5.

Case-specific data 110 can be precompiled by experts. It can also be obtained as user response to questions contained in a component of expert system 100, for example user interface 104, knowledge base 108 or inference engine 106.

The functionality relied on by rules 120 of expert system 100 can also be obtained, in part, by a set of automatic actions executed using one or more computational processes 118. An example of a computational process 118 is:

Upon input of a target sequence (from Step 01) {

202 Search one or more sequence databases for homologs of the target antibody sequence. Store any such sequences in knowledge base 108

204 Identify any functional information provided for any of these target antibody sequences by any of these databases. Store any such functional information in knowledge base 108

206 Search one or more structure databases for homologs of the target antibody sequence. Store any such homolog structural information in knowledge base 108.

208 Search one or more databases for known variants of the target antibody sequence. Store any sequence and functional information in knowledge base 108.

210 Compute the scores for every enumerated substitution found in steps 202 through 208 using select rules 120.

Computational processes 118 can be stored in knowledge base 108 as illustrated in FIG. 1, in expert system 100, or in any data structure that is accessible by expert system 100. Some embodiments of expert system 100 include explanation subsystem 112. Explanation subsystem 112 provides reasons to the user for why particular substitutions are selected by rules 120. Some embodiments of expert system 100 include knowledge base editor 114 to allow an administrator to add, delete, or modify components of knowledge base 108 including, but not limited to, rules 120.

In some embodiments, expert system 100 provides scores for each substitution enumerated along with the contribution to that score from various methods 130 used to evaluate the desirability of each substitution. The weights 132 for the various methods 130 are derived from knowledge base 108 and can be updated by an expert using knowledge base editor 108 and can also be updated automatically using rules in knowledge base 108.

Inference engine 106 is a software module that reasons using information stored in knowledge base 108. One embodiment of inference engine 106 is a rule-based system. Rule-based systems typically implement forward or backward chaining strategies. Inference engine 106 can be goal driven using backward chaining to test whether some hypothesis is true, or data driven, using forward chaining to draw new conclusions from existing data. Various embodiments of expert system 100 can use either or both strategies. For example, some topics that can be posed by expert system 100 in a goal driven/backward chaining strategy can include: (i) how conservative should an approach be, (ii) how many iterations of the process are likely to achieve the activity of interest, (iii) by what factor should the desired activity increase, and (iv) descriptions of any prior experiments that have failed and why they have failed. Answers to these topics allows expert system 100 to access information from experiments and data from the scientific literature or from personal communications that can be relevant for the design of the sequence space of interest.

Inference engine 106 can calculate a probability that a variant residue will provide a desired activity in an antibody of interest. The antibody can be an Fab fragment, $(Fab)_2$ fragment, a scFv, fragment, a polynucleotide having its own activity of interest, a polynucleotide that encodes an antibody having an activity of interest, or a polynucleotide that encodes a polypeptide that is responsible for synthesis of an antibody having an activity of interest.

A profile 116 can be created by inference engine 106 based on probability scores and weighting factors. In some embodiments, inference engine 106 calculates the probability that defined substitutions will result in an antibody having the desired function, for any variant of the reference antibody. For example, in some instances, knowledge base 108 can contain information describing residue positions in the reference sequence that exhibit a high degree of variance in homologs or among sequences in the same structural or sequence class. Inference engine 106 may thus give a high probability that substitutions at such positions will be active. One method of calculating the degree of amino acid variance is described by Gribskov, 1987, Proc Natl Acad Sci USA 84, 4355. As another example, in some instances, a sequence alignment can be available in knowledge base 108 to serve as the basis of a Hidden Markov model that can be used to calculate the probability that one specific residue will be followed by a second specific residue. These models also include probabilities for gaps and insertions. See, Krogh, "An introduction to Hidden Markov models for biological sequences," in *Computational Methods in Molecular Biology*, Salzberg et al., eds, Elsevier, Amsterdam. Such models can be used by inference engine 106 to calculate the probability that a particular substitution will possess a desired function.

In some embodiments of the present invention, a variety of different substitution matrices 122 stored in knowledge base 108 can be used by expert system 100 to identify suitable replacement residues for positions likely to accept substitutions. Specifically, substitutions specific for antibody framework regions and antibody CDR regions can be generated using the sequences in the database. Additionally, substitutions based on the amino acid frequencies compiled for every CDR position for every antibody class in the kabat database can be derived. In addition, the availability of a replacement residue that is likely to be functional can itself determine whether or not a position is likely to accept substitutions. This can be generated from functional sequences that are naturally occurring and/or generated synthetically whose properties have been measured. Substitution matrix 122 choices will impact the probability calculated for likely functionality of a variant. Thus, if mutations based on sequence alignment are desired, a substitution matrix 122 derived from the set of sequences should be chosen. Alternatively, if mutations that depend on general mutability are desired, a substitution matrix 122 reflecting this need should be chosen. Substitution matrices 122 can be calculated based on the environment of a residue, e.g., inside or accessible, in coil or in beta-sheet. See, for example, Overington et al., 1992, Protein Sci 1:216.

Methods to identify solvent accessible residues and to compute their solvent availability are known in the art. See, for example, Hubbard, Protein Eng 1:159 (1987). Such calculated solvent availability can be used to determine which substitution matrix 122 is used. More complex substitution matrices 122 that consider secondary structure, solvent accessibility, and the residue chemistry are also suitable for use in probability matrices. See, for example, Bowie & Eisenberg, Nature 356:83 (1992).

Conservation indices 124 stored in knowledge base 108 can be used by inference engine 106 to calculate probabilities that a substitution will result in an antibody with desired properties. In this capacity, one can avoid mutating residues that are highly conserved, or conversely, focus mutations on conserved regions of the antibody. Algorithms for calculating conservation indices 124 at each position in a multiple sequence alignment are known in the art. See, for example, Novere et al., 1999 Biophys. Journal 76:2329-2345.

Inference engine 106 can also use knowledge of the effects of single mutations as a factor in calculating the probability that a substitution will possess a desired function when mutation effect data 126 is stored in knowledge base 108. Mutation effect data 126 can originate, for example, from mutagenesis scans or from those substitutions found in naturally occurring variants that affect the function of interest.

Inference engine 106 can also use structural information 128 (e.g., crystal structure, in silico models of antibodies, de novo modeled antibody, etc.) stored in knowledge base 108. For example, inference engine 106 can assign higher probabilities to amino acid residues in framework regions that are close to the CDR of an antibody, as will affect activity and/or specificity than more distant residues. Similarly, proximity to an epitope, proximity to an area of structural conflict, proximity to a conserved sequence, proximity to a binding site, proximity to a cleft in the protein, proximity to a modification site, etc. can be calculated from structural information 128 and used to calculate the probability that a substitution will result in a functional antibody. To calculate the distance of a residue from a region of functional interest, physical distances obtained using a known crystal structure of the reference sequence can be used. Alternatively, molecular modeling approaches can be used. For example, the structure of the reference sequence can be predicted based on its homology to a known structure, and then used to calculate distances. Or the entire structure of the reference sequence can be predicted and distances then calculated from the predicted structure.

In some embodiments structural information 128 is energy minimized. For example, the behavior of an antibody can be modeled using molecular dynamic simulations. In a specific example, a crystal structure or a predicted structure can be subjected to molecular dynamic simulation in order to model the effect of various external conditions such as the presence of solvent, the effect of temperature and ionic strength, upon the determined or predicted structure.

In addition to the examples of elements of information that can be used as a part of a knowledge base 108 described above, other information that can contribute to an antibody knowledge base 108 that can then be used by inference engine 106 of an expert system 100 to calculate the probability that a substitution will possess a desired function include, but is not limited to, individual sequence analysis (including sequence complexity, sequence content and composition, internal base-pairing and secondary structure predictions) sequence comparisons (including structure-based sequence alignments, homology-based sequence alignments, phylogenetic comparisons based on multiple pairwise comparisons, phylogenetic comparisons based on principal component analysis of sequence alignments, Hidden Markov models), evolutionary molecular analysis, structural analysis (including those using X-ray crystallographic data, nuclear magnetic resonance studies, structure threading algorithms, molecular dynamic simulations, active site geometry, determination of surface, internal and active site residues), known or predicted data relating sequence or structure to functional mechanisms, chemical and biophysical properties of functional groups, known or predicted functional effects of changes (for example information derived from the Protein Mutant Resource database, from an evolutionary comparison of sequence and activity data or from a comparison binding pockets and residues for the antibody with binding pockets and residues for other antibodies or sets of antibodies), substitution matrices derived from sequence comparisons, mutations that are known or that can be predicted to affect physical properties of proteins (including stability, thermostability), known or predicted properties (including plasticity and tolerance to substitutions) of homologous or related antibodies (including other members of sequence, structurally or functionally related classes of antibodies), known or predicted immunological effects and constraints for specific sequence residues or motifs, known or predicted sequence effects on in vivo or in vitro post-translational or post-transcriptional modifications, known or predicted effects of the functional environment (including other proteins, nucleic acids or other molecules contained within a cell), measured or predicted biochemical or biophysical properties (including crystallization), effects of sequences on the expression of nucleic acids or proteins (including known or predicted RNA splice sites, protein splice sites, promoter sequences, transcriptional enhancer sequences, transcription and translation terminator sequences, sequences that affect the stability of a protein or nucleic acid, codon usage tables, nucleic acid GC content). Sources of this information can include, without limitation, text mined from scientific literature, data mined from genomic sequences, expressed sequences, structural databases and in second and subsequent iterations of the process, case specific data from the first points of the sequence space mapped.

In some embodiments of the present invention, knowledge base 108 is optionally preprocessed for information by knowledge base editor 114. For example, knowledge base 108 can contain all available antibody sequences. During preprocessing by knowledge base editor 114, such sequences can be, for example, (i) aligned and distributed on a phylogenetic tree, (ii) grouped by principal component analysis (PCA), (iii) grouped by nonlinear component analysis (NLCA) (iv) grouped by independent component analysis (ICA), used to create sequence profiles (see, for example Gribskov, 1987, Proc Natl Acad Sci USA 84, 4355), (v) used to create Hidden Markov models or (vi) used to calculate structures prior to interrogation by the user (vii) classified into canonical structural classes as defined by Chothis and lesk (REF). PCA, NLCA, and ICA is described in, for example, Duda et al., *Pattern Classification*, Second Edition, John Wiley & Sons, Section 10.13, which is hereby incorporated by reference.

In one embodiment, the output from an expert system 100 will describe the various substitutions recommended by methods 130 based on assignment of scores, confidences, ranks, or probabilities (hereinafter "scores") using rules 120 in knowledge base 108. In preferred embodiments, these scores are cumulative. That is, every rule 120 used by a method 130 will assign a score to the substitution under consideration and these scores can be higher if more rules are satisfied.

Figure 3:
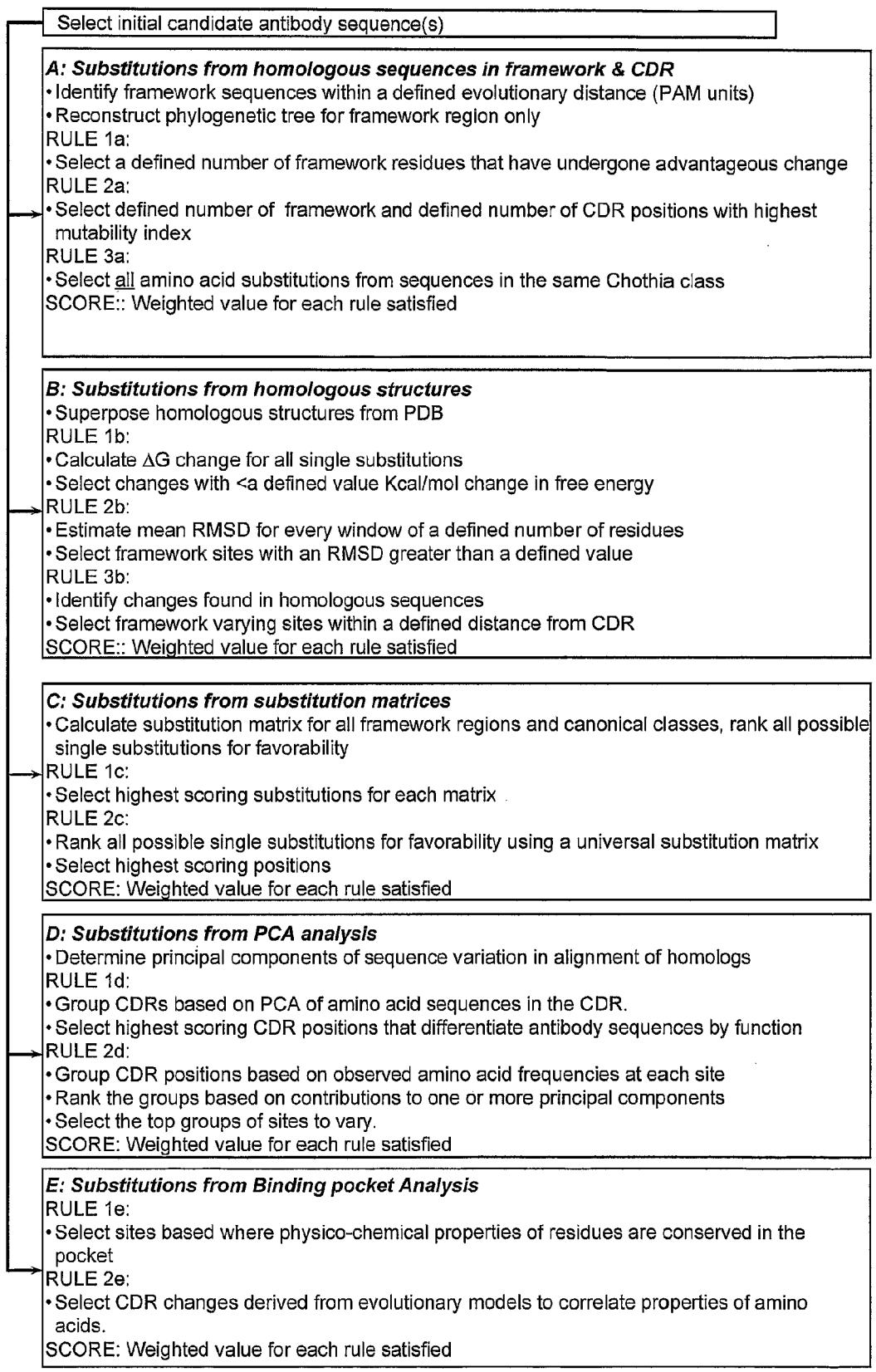
FIG. 3 is a schematic representation of a method for selecting amino acid substitutions for the optimization or humanization of antibodies in accordance with an embodiment of the present invention.

For example, FIG. 3 shows a series of steps that can be executed by expert system 100 in order to identify substitutions that are likely to increase the ability of an antibody to bind to a specific target antigen. Five independent methods 130 are shown for assessing the suitability of a substitution in the framework and CDRs: (i) substitutions from antibody sequences derived from other species and/or from synthetically derived antibodies and/or germline sequences from human and/or other species (ii) substitutions from homologous and modeled structures, (iii) substitutions from substitution matrices, (iv) substitutions from principal component analysis (PCA) and (v) substitutions from binding pocket analysis. For each method 130, one or more rules (filters) 120 defined in knowledge base 108 are used. For example, method (ii), substitutions from homologous structures, uses two rules 120. The first rule 120 is an estimate of the mean root mean square deviation (RMSD) from the target structure for every five residue window of the homolog structure, and select framework sites that deviate from the target structure by more than three A. The second rule 120 identifies amino acid substitutions that are found in homologous sequences and select framework sites that are within five A of the complementarity determining region. In FIG. 3 rules 120 are applied as filters: a substitution that satisfies one of the rules is considered to have passed through that filter and receives a score. For example, in FIG. 3, this score is 1. The rules 120 used (applied) by the four other methods 130 for assessing the suitability of substitutions shown in FIG. 3 are also applied as filters. The score for each method can then be combined, for example by summing them. All possible substitutions can then be ranked in order of their cumulative scores. Although there are many variants, in some embodiments of the present invention, a component of step 02 of FIG. 2 uses the following algorithm in order to identify suitable substitutions:

```
for each residue position j of the antibody identified in step 01
{
    for each possible substitution k of residue j
    {
        initialize score_{jk};
        for each method m (method 130) in a suite of methods
        {
            initialize score_m
            for each filter n (rule 120) in method m
            {
                compute filter n based on substitution k at position j;
                score_m = score_m + result of filter n;
            }
            score_{jk} = score_{jk} + score_m
        }
    }
    rank all scores_{jk}
```

Those substitutions that have satisfied more of the rules will have been assigned higher cumulative scores (score$_m$), and those with the highest scores will be selected for incorporation into a set of antibody variants.

There are many variations of ways to combine scores produced by two or more rules 120. Variations are possible (i) in the methods of assigning scores, (ii) in the methods of combining scores, and (iii) in the methods of assigning different weights to scores produced by different rules 120. Rules 120 can also be combined on a case by case basis, using expert knowledge. These rules 120 can be stored in a knowledge base 108 and can be executed by inference engine 106 using user input acquired by questioning the user for requirements and knowledge via the user interface 104.

5.1.1 Variations in the Method of Assigning Scores

In preferred embodiments, each rule 120 produces a reproducible quantitative value that can be used as a measure of the suitability of a substitution. However, there are many different ways in which quantitative scores can be obtained, and these ways can differ between different rules 120. A rule 120 can be used to produce an absolute quantitative score. This absolute quantitative score can be used directly, or it can be used to create a rank order list or a filter. As an example consider rule 1b of FIG. 3. Rule 1b calculates the difference in free energy between a target antibody and an antibody containing a substitution. This value can then be used in several different ways to compare the favorability of different substitutions. For example, (i) the absolute value of the free energy difference (caused by the substitution) can be used, (ii) the free energy differences of all possible substitutions can be ranked in order of favorability, then a subset of substitutions that are predicted to be the most favorable can be selected and assigned a score, (iii) the score can be a single value assigned to all of the substitutions belonging to the subset of the most favorable, (iv) the score can be a measure of the rank order of the substitution, so that the most favorable substitutions receive a higher score than those that are calculated to be less favorable, (v) a rule can also be used to rank all possible substitutions in order of predicted favorability and then eliminate a subset of these substitutions that are predicted to be the least favorable. In option (v), substitutions that were eliminated would receive a score of zero.

A way in which the predicted free energy change of a substitution can be used as a rule to obtain quantitative measures of the favorability of a substitution has been described. An absolute quantitative value obtained by any method for favorability can also be transformed by use of a function. In the case of free energy change, instead of using the free energy change itself the exp(free energy change) or step functions that can reflect (iii) above can be used. One of skill in the art will appreciate that there are other rules that can be applied to assess the effect of a substitution in order to produce absolute quantitative scores and all such other rules are included within the scope of the present invention.

5.1.2 Variations in the Method of Combining Scores

The scores produced by individual rules can be combined in a variety of ways. In some embodiments they are added together in the manner illustrated in the algorithm illustrated in Section 5.1 above. In some embodiments, the scores are multiplied together. For example,

```
for each residue position j of the antibody identified in step 01
{
    for each possible substitution k of residue j
    {
        initialize score_{jk};
        for each method m (method 130) in a suite of methods
        {
```

-continued

```
                initialize score_m
                for each filter n (rule 120) in method m
                {
                    compute filter n based on substitution k at
position j;
                    score_m = score_m × result of filter n;
                }
            score_jk = score_jk + score_m
            }
    }
    rank all scores_jk
```

In some embodiments, one or more rules 120 can be used as a filter, so that only substitutions passing the one or more filter are used, regardless of their scores from the other rules. For example,

```
    for each residue position j of the antibody identified in step 01
    {
        for each possible substitution k of residue j
        {
            initialize score_jk;
            set abort false
            for each method m (method 130) in a suite of methods
            {
                initialize score_m
                for each filter n (rule 120) in method m
                {
                    compute filter n based on substitution k at
position j;
                    if result of filter n is negative {
                        set abort true
                        break;
                    }
                    score_m = score_m + result of filter n;
            }
            if abort
            {
                set score_jk = 0
                break;
            }
            else
            {
                score_jk = score_jk + score_m
                /* or score = f1 (score_jk)* f2(score_m)*/
                /* scores can be functionally transformed
                or normalized
            */
            }
    }
    }
    rank all scores_jk
```

In some embodiments, a cumulative score can be produced by any mathematical function of the scores produced by two or more individual rules. For example,

```
for each residue position j of the antibody identified in step 01
{
    for each possible substitution k of residue j
    {
        initialize score_jk;
        for each method m (method 130) in a suite of methods
        {
            initialize score_m
            for each filter n (rule 120) in method m
            {
                compute filter n based on substitution k at
position j;
                score_m = score_m + weight_n ×(result of filter n);
        }
```

-continued

```
            score_jk = score_jk + score_m
        }
    }
    rank all scores_jk
```

In the exemplary algorithm above weight, is some rule 120 specific weight that is independently assigned to a rule. Such weights can be stored in knowledge base 108 and adjusted by an expert using knowledge-base editor 114 (FIG. 1).

In addition, prior to combination, scores produced by individual rules can be scaled or normalized and/or transformed by a mathematical function to facilitate their combination. For example, in the case humanization of RSV-19, the mutation I46V was identified as the most favorable substitution in the framework region by combining the scores from methods 130. The distance, expressed in fraction of amino acid differences, was transformed and a Poisson correction (−log [1-fraction]) applied and multiplied by the product of the absolute scores obtained from the other methods 130. The resulting scores for all substitutions were ranked and I46V (combination score 126) was ranked 1. In this example different criteria were used to compute the scores for the framework and CDR regions.

5.1.3 Variations in the Method of Assigning Weights to Scores from Different Rules As indicated in Section 5.1.2, the scores produced by individual rules 120 can be assigned different weights prior to being combined. For example, if the total score for a substituting monomer x at position i ($S_{ix}$) is obtained by adding the scores obtained by applying n different rules, the score can be expressed by Equations (1) or (2):

$$S_{ix}=W_1 i_x R_1+W_2 i_x R_2+W_3 i_x R_3+W_4 i_x R_4+W_5 i_x R_5+\ldots+W_n i_x R_n \qquad \text{(Eq. 1)}$$

where, $i_x R_n$ is the score given by rule n for substituting monomer x at position i; and $W_n$ is a weight applied to the score given by rule n $$S_{ix}=f(W_1 R_i(i_x), W_2 R_2(i_x), \ldots, W_j R_j(i_x)) \qquad \text{(Eq. 2)}$$

where, $R_j(i_x)$ is the score given by rule j for substituting monomer x at position i;

$W_j$ is a weight applied to scores given by rule j; and f is some mathematical function.

Rules (and weights) can be (i) specific for a substitution of monomer x at a specific location, (ii) specific for position for any and/or a group of monomer substitution(s), (iii) specific for any and/or a group of positions for a specific monomer x, (iv) specific for any substitutions derived from a particular and/or a group of homologs, (v) or specific for any position derived from a particular and/or a group of homologs.

The use of weights to modify scores obtained using different rules has a number of benefits.

Firstly, the use of weights to modify scores obtained using different rules 120 allows different rules 120 to have different degrees of influence over the final score for a substitution. For example if Rule 4 is the most important in determining the suitability of a substitution in a particular antibody, then this rule can be made to dominate the total score for the substitutions by making $W_4$ much higher than the other weights.

Secondly, the use of weights to modify scores obtained using different rules 120 allows different rules 120 to have different degrees of influence over the final score for a substitution depending upon the class or subclass of antibodies being considered. For example a rule 120 considering the structural effect of a substitution can be most important for engineering an antibody, while a rule 120 considering the statistical likelihood of a substitution using a substitution matrix can be most important for engineering a protease. In this case, by first determining to which class of antibody the target antibody belongs, expert system 100 can then be used to assign weights to the scores from different rules 120 that will result in the most accurate assessment of the favorability of substitutions. Moreover, as previously described, expert system 100 can assign different weights to different methods, to produce more control over how substitutions scores are computed.

Thirdly, the use of weights to modify scores obtained using different rules 120 allows expert system 100 to incorporate information obtained from previous experiments. For example, another aspect of the invention involves the use of sequence-activity relationships to empirically measure the contribution of substitutions to one or more activity of an antibody. This aspect of the invention is described more fully in Section 5.5. This sequence-activity determination effectively creates a feedback loop by which weights assigned to the scores from different rules 120 applied by expert system 100 can be adjusted. As an example, consider the case in which 20 substitutions within an antibody (represented by $S_1$-$S_{20}$) receive final combined scores $C_1$-$C_{20}$ from expert system 100. A set of antibodies that contain these substitutions are synthesized, and a sequence-activity relationships derived using wet lab assays. The sequence-activity relationships are used to determine actual scores that measure the fitness of each substitution for the desired activity of the antibody ($F_1$-$F_{20}$). The weights applied to each rule 120 and/or method 130 can then be adjusted so that the observed fitness of each substitution, $F_1$-$F_{20}$, correlate more closely with scores $C_1$-$C_{20}$ produced by expert system 100. In some embodiments, this correlation is the correlation between the absolute values of the scores for each substitution from expert system and the observed fitness of each substitution derived from the sequence-activity relationship. In some embodiments, the correlation can be a correlation between the rank order of effect of substitutions predicted by expert system 100 and the rank order of substitutions observed or derived from the sequence-activity relationship. The weights applied to each rule 120 can also be adjusted so that the correlation between the observed fitness of substitutions and the scores produced by expert system 100 is maximized for more than one set of substitutions, in one or more different target antibodies.

Different classes of antibodies can optionally be used to provide different sets of substitutions for comparing observed fitness and scores produced by expert system 100. This allows different weights to be calculated to apply to the scores produced by different rules 120 as a function of antibody class. One skilled in the art will appreciate that there are many possible variations of using experimental results to adjust weights applied to rule 120 scores. All such variants, whose predictive scoring functions can be adjusted based upon experimental data, are within the scope of the expert systems 100 of the present invention and can thus be considered systems capable of learning.

Because of the capacity for expert systems 100 of the present invention to learn by, for example, adjustment of rule 120 weights, in some instances it can be desirable to select substitutions that are favored strongly by different rules 120. Such selection can facilitate the establishment of the appropriate weights to be applied to different rules 120 used by expert system 100.

The score for a substitution based on two or more rules can be calculated independently or using conditional probabilities. An expert system 100 can produce scores for at least 2, 3, 4, 5, 6, 7, 8, 9, 10, 11, 12, 13, 14, 15, 16, 17, 18, 19, 20, 25, 30, 35, 40, 45, 50, 60, 70, 80, 90 or 100 positions in the reference sequence up to the entire sequence, and can include contiguous residues or noncontiguous residues or mixtures thereof. The expert system 100 can include at least 2, 3, 4, 5, 6, 7, 8, 9, 10, 11, 12, 13, 14, 15, 16, 17, 18, 19, 20, 25, 30, 35, 40, 45 or 50 different residues. Naturally occurring residues can be included in the expert system, as well as unnatural residues for synthetic methods, and combinations thereof.

In another embodiment of the invention, the above calculations can be performed by an expert with access to the relevant knowledge base 108, for example, by using user interface 104.

Examples of the ways in which such expert system 100 can be used to automatically select substitutions to make in an antibody will now be described in the following sections with reference to FIGS. 1 and 2. The following exemplary process is intended to illustrate one possible embodiment of the invention. One skilled in the art will recognize that there are many possible variations on this theme, and the following is not intended to limit the present invention. The selection process refers to the scheme shown in FIG. 3.

FIG. 3 shows a series of independent rules 120, each of which can be used to produce a score for any possible amino acid substitution in an antibody. In one embodiment of the invention, all possible single substitutions can be enumerated computationally and then scored according to one or more of the rules executed by expert system 100.

5.1.4 Rules Based on Substitutions from Related Antibody Sequences

One source of information that can be used to construct rules 120 that assess the likely effect of amino acid substitutions upon one or more activities of an antibody is the sequence of one or more homologous or related antibodies. See, for example, FIG. 3, rule 3a. Homologous sequences are generally analogous functionally and structurally, although having been subjected separately to different selective pressures they are also likely to be optimized differently. Antibody sequences variants can also be generated in the lab using many techniques and sequence properties of several such antibodies are available in the database and literature. Amino acids that differ between homologous sequences thus provide a guide to substitutions that are likely to yield functional though different antibody sequences. For humanization of antibodies, alignment of the target antibody with human germline sequences available in the databases is used to identify residues in the human framework. The sequences can be grouped into classes as defined by Chothia and Lesk (Chothia C, Lesk A M, "Canonical structures for the hypervariable regions of immunoglobulins." J Mol Biol. 1987 Aug. 20; 196(4):901-17). Alignment of homologous sequences can therefore be used to identify candidate substitution positions.

In one approach, homologous antibody sequences or sequence classes are aligned (e.g., by using using clustalw; Thompson et al., 1994, Nucleic Acids Res 22: 4673-80) and then a phylogenetic tree is reconstructed. Conservation indices can then be calculated for each site (e.g., Dopazo, 1997, Comput Appl Biosci 13: 313-7) and the information content calculated for each site (e.g., Zhang, 2002, J Comput Biol 9: 487-503). These scores can be exhaustively calculated for every position in the antibody. The scores reflect the extent of tolerance to substitutions in the antibody at each position. The scores can be normalized using the phylogenetic tree to eliminate bias in the homolog sequences found in databases (for e.g. ease of access to certain template DNAs results in sequences from certain class of organisms dominates the database.) Scores for a given alignment can also be normalized to have an average value of 0.0 and a standard deviation of 1.0, or other standard procedures can be used to compare and combine scores from multiple methods. These values can then be used directly as a score, as outlined above and in Equation (1) or Equation (2). In some embodiments, all sites with a score above a certain threshold value can be selected. For example, a cutoff (threshold) of 0.0 can be chosen (which is set to be the average score). In still other embodiments, all sites with a score below a certain threshold value can be eliminated. In some embodiments, the most variable (e.g., least conserved) sites can be selected by ranking the sites in order of these scores. For example the most highly scoring site can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 most highly scoring sites can be selected. In some embodiments the least variable (e.g., most conserved) sites can be eliminated by ranking the sites in order of these scores. For example, the least highly scoring site can be eliminated, or the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900 or 1000 least highly scoring sites can be eliminated (FIG. 3, Rule 1a).

Amino acid diversity and tolerance at each site can be measured as a fitness property of each amino acid at every location. In this approach all related antibody sequences available can be considered. The most fit residue for that position carries a higher value (e.g., Koshi et al., 2001, Pac Symp Biocomput 191-202; O. Soyer, M. W. Dimmic, R. R. Neubig, and R. A. Goldstein; Pacific Symposium on Biocomputing 7:625-636 (2002). Sites can be grouped into site-classes or treated independently. Sites and site classes most fit to change based on the substitution rate and the substitutions most favorable based on the fitness can be selected (FIG. 3, Rule 2*a*). In some embodiments, these values of fitness can then be used directly as a score, as outlined above and in Equation (1) or Equation (2). In some embodiments all sites with a score above a certain threshold value can be selected. For example, a cutoff (threshold) of 0.0 can be chosen (when the normalization of scores sets the wild type residue found in the reference to be 0.0. In some embodiments, all sites with a score below a certain threshold value can be eliminated. Threshold values of 0.0 or below can be eliminated, thereby only including amino changes that have a higher fitness value that the reference wild type amino acid found in that position. In some embodiments, the sites most tolerant to change can be selected by ranking the sites in order of these scores. For example, the most highly scoring site can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 most highly scoring sites may be selected. In some embodiments, the sites least tolerant to change can be eliminated by ranking the sites in order of these scores. For example, the least highly scoring site can be eliminated, or the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900 or 1000 least highly scoring sites can be eliminated.

For example, in the study of G-protein coupled receptors (GPCR) by Soyer et. al. (O. Soyer, M. W. Dimmic, R. R. Neubig, and R. A. Goldstein; Pacific Symposium on Biocomputing 7:625-636 (2002)), using the 8-site class model the class #8 was identified to have the highest substitution rate and the property correlating with fitness of amino acids at these positions was identified to be "charge transfer" propensity of the amino acid. In the present invention, amino acids in the sites that carry a higher relative fitness compared to the wild type amino acid found in that position are identified as suitable for substitution. The scores for these residues will be higher and can be combined with other methods 130.

Scores can also be assigned to residues from related sequences that are classified into the same canonical class as the target antibody. In this approach substitutions that are derived from sequences that are part of the same Chothia-Lesk canonical class can be scored (FIG. 3 Rule 3*a*).

5.1.5 Rules Based on Substitutions from Related Antibody Structures

The structures of many antibodies and their variants are also available in the RCSB protein data bank ((2002) *Acta Cryst. D* 58 (6:1), pp. 899-907); and Structural Bioinformatics (2003); P. E. Bourne and H. Weissig, Hoboken, N.J., John Wiley & Sons, Inc. pp. 181-198. The availability of structures can help identify amino acid changes that affect protein function. One way in which they can be used to do so is to avoid changes to the antibody of interest that will not be structurally tolerated by the antibody. Changes computed in-silico using energy functions and force fields correlate with experimentally measured free energy changes in the stabilities of proteins. See, for example, Privalov et al., 1988, Adv Protein Chem 39: 191-234; Lee, 1993, Protein Sci 2: 733-8; Freire, 2001, Methods Mol Biol 168: 37-68; and Guerois et al., 2002, J Mol Biol 320: 369-87). Therefore, candidate amino acid changes can be modeled into the structure(s) computationally and changes in the free energy computed. These computationally calculated changes in free energies resulting from the substitutions can then be used directly as a score, as outlined above and in Equation (1) or Equation (2). Alternatively, all changes can be selected that increase the free energy of the antibody by less than a certain value. For example, all changes that would increase the free energy by less than 1 kCal/mol can be selected, all changes that would increase the free energy by less than 1.5 kCal/mol can be selected, all changes that would increase the free energy by less than 2 kCal/mol can be selected, or all changes that would increase the free energy by less than 2.5 kCal/mol can be selected. In some embodiments, all changes can be eliminated that increase the free energy of the antibody by more than a certain value. For example, all changes that would increase the free energy by more than 1 kCal/mol can be eliminated, all changes that would increase the free energy by more than 1.5 kCal/mol can be eliminated, all changes that would increase the free energy by more than 2 kCal/mol can be eliminated, all changes that would increase the free energy by more than 2.5 kCal/mol can be eliminated. In some embodiments, the best tolerated substitutions can be selected by ranking the sites in order of the predicted increase in free energy. For example, the substitution with the lowest increase in free energy can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 substitutions with the lowest increase in free energy may be selected. In some embodiments, the substitutions with the greatest increases in free energy can be eliminated by ranking the sites in order of these scores. For example, the 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900, 1000, 2000, 3000, 4000, 5000, 6000, 7000, 8000, 9000, 10000, 12000, 14000, 16000, 18000 or 20000 substitutions with the greatest increases in free energy can be eliminated (FIG. 3, Rule 1b).

In alternative embodiments, multiple changes can be modeled into the structure(s) computationally and changes in the free energies resulting from the substitutions computed. These free energy values can be used to identify changes that are "valid" independently, but not together Amino acid changes that are independent can be selected preferentially Amino acid clashes that yield a higher free energy when compared to the free energies produced by modeling changes separately can be eliminated.

Regions of the antibody that differ structurally between antibodies are more likely to tolerate change, while those regions that are structurally conserved are likely to be less tolerant. Structures can be directly obtained from the database or predicted using various structure modeling software packages. Structures of homologs and mutants can be superposed on the wild type structure. See, for example, May et al., 1994, Protein Eng 7: 475-85; and Ochagavia et al., 2002, Bioinformatics 18: 637-40). Structural conservation can be calculated as the root mean squared (RMS) deviations of the backbones of the superposed chains. This can be computed as the deviations of individual residues, or more preferably as the deviations of a running average over a between two and ten residue stretch of the backbone between the target antibody and one or more homologous antibodies. These computationally calculated RMS deviations for every position between homologous structures can then be used directly as a score, as outlined above and in Equation (1) or Equation (2). In some embodiments, RMS deviations between the alpha carbons (or backbone atoms) in the structure of the target antibody and one or more homologous or related antibodies that are greater than a threshold value can be considered structurally labile and these sites can be selected. This threshold RMS deviation between homologous structures can be greater than 2 Å, 2.5 Å, 3 Å, 3.5 Å, 4 Å, 4.5 Å, 5 Å.

In some embodiments, RMS deviations between the alpha carbons in the structure of the target antibody and one or more homologous or related antibodies that are less than a threshold value can be considered structurally conserved and these sites can be eliminated. This threshold RMS deviation between homologous structures can be less than 2 Å, 2.5 Å, 3 Å, 3.5 Å, 4 Å, 4.5 Å, or 5 Å.

In some embodiments sites can be ranked in order of the calculated RMS deviations between the alpha carbons in the structure of the target antibody and one or more homologous or related antibodies and those with the highest calculated RMS deviations selected. For example, the site with the highest calculated RMS deviations between homologous structure can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 sites with the highest calculated RMS deviations between homologous structure may be selected.

In some embodiments, sites can be ranked in order of the calculated RMS deviations between the alpha carbons in the structure of the target antibody and one or more homologous or related antibodies and those with the lowest calculated RMS deviations eliminated. For example, the site with the lowest calculated RMS deviations between homologous structures can be eliminated or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 sites with the lowest calculated RMS deviations between homologous structure can be eliminated (FIG. 3, Rule 2b). Changes near binding sites (and CDRs) are highly likely to influence the activity of the antibody and are good candidates for substitution. All amino acid substitutions that are found in one or more variants can be tested for proximity to a binding or regulatory site of the antibody. In some embodiments, the distance between an amino acid substitution that is found in one or more homologs from a binding or catalytic or regulatory site can be used directly as a score, as outlined above and in Equation (1) or Equation (2). Alternatively, in some embodiments, all amino acid substitutions that are found in one or more homologs and that are within a threshold distance of a binding or regulatory site in the antibody can be selected. This threshold distance can be less than 2 Å, 2.5 Å, 3 Å, 3.5 Å, 4 Å, 4.5 Å, 5 Å, 5.5 Å, 6 Å, 6.5 Å, 7 Å. In still other embodiments, all amino acid substitutions that are found in one or more homologs and that are beyond a threshold distance of a binding or regulatory site in the antibody can be eliminated. This threshold distance can be more than 2 Å, 2.5 Å, 3 Å, 3.5 Å, 4 Å, 4.5 Å, 5 Å, 5.5 Å, 6 Å, 6.5 Å, or 7 Å. In still other alternative embodiments, all amino acid substitutions that are found in one or more homologs can be ranked in order of proximity to a binding or regulatory site in the protein and those that are closest to the binding or regulatory site selected by a rule 120. For example, the substitution closest to the binding or catalytic or regulatory site can be selected, or between 2 and 20, between 10 and 100, or the top 200 substitutions closest to the binding or catalytic or regulatory site can be selected. In still other alternative embodiments, all amino acid substitutions that are found in one or more homologs can be ranked in order of proximity to a binding or regulatory site in the antibody and those that are farthest from the binding or catalytic or regulatory site eliminated. For example, the substitution farthest from the binding or regulatory site can be eliminated. In some embodiments, between 2 and 20, between 10 and 100, or the top 200 substitutions farthest from the binding or regulatory site can be eliminated.

5.1.6 Rules Based on Substitutions from Substitution Matrices

Another source of information that can be used to construct rules 120 that assess the likely effect of amino acid substitutions upon one or more activities of an antibody is the frequency with which one amino acid is observed to substitute for another amino acid in different proteins. The matrix can be expressed in terms of probabilities or values derived from probabilities by mathematical transformation involving probabilities of transitions or substitutions (Pij) and observed frequencies of amino acids(Fi). Matrices using such transformation include scoring matrices like PAM100, PAM250, and BLOSUUM etc. See, for example, FIG. 3, rule 1c. Substitution matrices are derived from pairwise alignments of protein homologs from sequence databases. They constitute estimates of the probability that one amino acid will be changed to another while conserving function. Different substitution matrices are calculated from different sets of sequences. For example, they can be based on the structural environment of a residue (Overington, 1992, Genet Eng (N Y) 14: 231-49; and Overington et al., 1992, Protein Sci 1: 216-26.) or on additional factors including secondary structure, solvent accessibility, and residue chemistry (Luthy et al., 1992, Nature 356: 83-5. Substitution matrices can be derived for specific sites or group of sites in the antibody. Specifically, substitutions specific for antibody framework regions and antibody CDR regions can be generated using the sequences in the database. Additionally, substitutions can be derived based on the amino acid frequencies compiled for every CDR position for every antibody class in the kabat database.

A substitution matrix that best captures the observed sequences in the antibody family of interest can be calculated using the Bayesian method developed by Goldstein et al. (Koshi et al., 1995, Protein Eng 8: 641-645) and used to score all candidate substitutions.

In some embodiments these values can then be used directly as a score, as outlined above and in Equation (1) or Equation (2). The scores can expressed as Pij: the probability of substituting residue i with j. Any transformations of Pij can also be used. Pij can be computed for a specified evolutionary distance. In alternative embodiments, all substitutions with a probability above a certain threshold value may be selected. Threshold values of 0.00001, 0.00001, 0.0001, 0.01 or 0.1 can be used for probabilities and/or threshold values of −5, −4, −3, −2, −1, 0, 1, 2, 3, 4, 5 for any PAM matrix. In still other embodiments, all substitutions with a probability below a certain threshold value may be eliminated. Threshold values of 0.00001, 0.00001, 0.0001, 0.01 or 0.1 can be used for probabilities and/or threshold values of −5, −4, −3, −2, −1, 0, 1, 2, 3, 4, 5 for any PAM matrix In still other embodiments, the most favorable substitutions can be selected by ranking substitutions in order of their substitution matrix probability scores. For example, the most highly scoring substitution can be selected, or the top 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 most highly scoring substitutions can be selected. In still other embodiments, the least favorable substitutions can be eliminated by ranking substitutions in order of their substitution matrix probability scores. For example, the least substitution with the lowest substitution matrix probability may be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 substitutions with the lowest substitution matrix probability can be eliminated.

A substitution or a scoring matrix can be calculated by considering homologous and/or related antibodies from many different antibody classes (e.g., Benner et al., 1994, Protein Eng 7: 1323-1332; and Tomii et al., 1996, Protein Eng 9: 27-36) can be used to score all candidate substitutions. In some embodiments, these values can then be used directly as a score, as outlined above and in Equation (1) or Equation (2). In some embodiments, all substitutions with a probability above a certain threshold value can be selected. Threshold values of 0.00001, 0.00001, 0.0001, 0.01 or 0.1 can be used for probabilities and/or threshold values of −5, −4, −3, −2, −1, 0, 1, 2, 3, 4, 5 for any PAM matrix can be used. In still other embodiments, all substitutions with a probability below a certain threshold value can be eliminated. Threshold values of 0.00001, 0.00001, 0.0001, 0.01 or 0.1 can be used for probabilities and/or threshold values of −5, −4, −3, −2, −1, 0, 1, 2, 3, 4, 5 can be used for any PAM matrix. In still other embodiments, the most favorable substitutions can be selected by ranking substitutions in order of their substitution matrix probability scores. For example the most highly scoring substitution may be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 most highly scoring substitutions can be selected. In still other embodiments, the least favorable substitutions can be eliminated by ranking substitutions in order of their substitution matrix probability scores. For example, the least substitution with the lowest substitution matrix probability may be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000 substitutions with the lowest substitution matrix probability can be eliminated.

5.1.7 Rules Based on Substitutions from Principal Component Analysis of Sequence Alignments Antibody sequences can be mathematically represented in terms many variables, each variable representing the type of amino acid at a specific location. For example the sequence AGWRY can be represented by 5 variables, where variable 1 assumes a value of "A" corresponding to position 1, variable 2 is "G" corresponding to position 2 and so on. Each variable can assume 1 of 20 possibilities. Alternatively each variable can also represent multiple positions (say 2) and assume 1 of 400 values (for 2 positions) corresponding to 20×20=400 combination of possible amino acid pairs. Alternatively, each position can assume a value corresponding to a physico-chemical property of the amino acid instead of amino acid identity. Alternatively, each variable can be a combination of variables representing properties of amino acids. Alternatively, each variable can be represented in a binary form corresponding to presence or absence of a particular amino acid. Alternatively, each variable can be represented in a binary form corresponding to presence or absence of a defined group of amino acids.

Typical antibodies contain many hundred variables. A set of antibodies are various points in the variables space, and relationships between various antibodies can be represented in terms of the values of the variables corresponding to those antibodies. In such a high-dimension space (due to high degree of variables) antibodies can be clustered and classified using statistical techniques like the principal components analysis, k-means clustering, SVM etc.

Using such methods, particularly but not limiting to Principal Component Analysis (PCA), we can classify sequences and identify residues that differentiate various related antibody sequences and their functions. Typical antibody sequence alignments contain many amino acid positions at which differences occur, leading to a high number of dimensions required to represent the sequence space. A sequence alignment can be subjected to principal component analysis to identify new composite dimensions that describe and visualize a significant fraction of the variation between a set of sequences. The new dimensions (the principal components) can also be described in terms of the contributions of each monomer variation within the original sequence alignment to that dimension (the "loads"). Typically a single principal component contains contributions from tens or hundreds of different monomer differences within a set of antibody sequences. One powerful application of principal component analysis is that it can be used to suggest a relationship between antibody sequence and function. Antibody sequence can be represented in terms of the principal components of that sequence. Principal components can then be identified in which antibodies are grouped functionally. The loads of those principal components can then be used to identify the monomers that are most responsible for the grouping of the antibodies within sequence space. These monomers are thus good candidates for substitutions likely to affect function.

Thus for proteins, amino acid substitutions that are most important in differentiating and grouping sequences are often also those that functionally differentiate the proteins. Identification of such amino acids using dimension-reducing techniques such as principal component analysis has been described (e.g., Casari et al., 1995, *Nat Struct Biol* 2: 171-178; Gogos et al., 2000, *Proteins* 40: 98-105; and del Sol Mesa et al., 2003, J Mol Biol 326: 1289-1302). PCA can identify sequence features and substitutions corresponding to the desired phenotype of the protein and scores "loads" for these features in the direction of desired phenotype are used as absolute scores or as filters to identify substitutions.

An example of the use of principal component analysis for identification of favorable substitutions is also shown in FIGS. 8-12. FIG. 8 shows the accession number of the list of 49 proteases whose sequences are homologous to proteinase K. A property of interest in this example is activity during or after exposure of the protein to heat. The 49 sequences were subjected to principal component analysis, and the distribution of the sequences in the first two principal components is shown in FIG. 9. Proteases 46, 47, 48 and 49 were all obtained from thermostable organisms and can thus be expected to possess desirable thermostability properties. As shown in FIG. 9, these four proteases are grouped together in the first two principal components of the sequence space, characterized by strongly negative scores in both principal components 1 and 2. FIG. 10 shows the contributions (the "loads") of all amino acid differences within the alignment of the 49 proteases, to the new dimensions principal components 1 and 2. FIG. 11 shows an expanded detail of the lower left corner of FIG. 10 in which the identities of each amino acid contributing to the principal components are now shown. These amino acids are those most responsible for giving a protein sequence a strong negative score in principal component 1 and principal component 2. These contributions are quantitated in FIG. 12. Because these scores are also those seen for proteases from thermophilic organsisms, the amino acids that are primarily responsible for conferring these scores upon proteins are very good candidates for amino acids that may confer desirable properties, in this case thermostability.

An example of the use of principal component analysis related to antibody humanization for identification of favorable substitutions is also shown in FIGS. 24-28. FIG. 24 shows the sequence identification number listed by locus of germline sequence from VBase (available at http://www.mrc-cpe.cam.ac.uk/). A properties of interest in this example are characteristics of sequence 4-28. The heavy chain of sequences listed in FIG. 24 along with the heavy chain of the murine antibody RSV19 were subjected to principal component analysis, and the distribution of the sequences in the first two principal components is shown in FIG. 25. Sequence 4-28 is the sequence cluster containing sequences close in locus id. As shown in FIG. 25, these are grouped together in the first principal components of the sequence space, characterized by strongly positive scores in principal component 1. FIG. 26 shows the contributions (the "loads") of all amino acid differences within the alignment, to the new dimensions principal components 1 and 2. FIG. 27 shows an expanded detail of the right center of FIG. 26 in which the identities of each amino acid contributing to the principal components are now shown. These amino acids are those most responsible for giving a protein sequence a strong positive score in principal component 1. Some of these contributions are quantitated in FIG. 28. The amino acids that are primarily responsible for conferring these scores upon proteins are serve as candidates for amino acids that may confer desirable properties, in this case characteristics of germline sequence 4-28.

An example of the use of principal component analysis related to antibody maturation for identification of favorable substitutions is also shown in FIGS. 29-33. FIG. 29 shows the sequence identification number listed by locus of germline sequence from VBase (available at http://www.mrc-cpe.cam.ac.uk/). A property of interest in this example are characteristics of sequence 5-a. The heavy chains of germline sequences along with the heavy chain of AAF21612 were subjected to principal component analysis, and the distribution of the sequences in the first two principal components is shown in FIG. 30. Sequence 5-a is in the sequence cluster containing sequences close to locus id 1-x. As shown in FIG. 30, these sequences are grouped together in the second principal component of the sequence space, characterized by strongly negative scores in principal component 2. FIG. 31 shows the contributions (the "loads") of all amino acid differences within the alignment, to the new dimensions principal components 1 and 2. FIG. 32 shows an expanded detail of the lower center of FIG. 31 in which the identities of each amino acid contributing to the principal components are now shown. These amino acids are those most responsible for giving a protein sequence a strong negative score in principal component 2. Some of these contributions are quantitated in FIG. 33. The amino acids that are primarily responsible for conferring these scores upon proteins are very good candidates for amino acids that may confer desirable properties, in this case characteristics of germline sequence 5-a.

Any sequence principal component can be used that contributes to differentiating between two sets of antibodies and that is likely to reflect some functional differences of interest. In some embodiments, the "load" contributed by a substitution to one or more such principal component of sequence can be used directly as a score, as outlined above and in Equation (1) or Equation (2). In some embodiments, all substitutions with a "load" above a certain threshold value can be selected. Threshold values can be determined from the distribution of load values. For example, select top ten percent positive loads in principal component 1. In some embodiments, all substitutions with a "load" below a certain threshold value can be eliminated. For example, eliminate the top ten percent of the negative loads in principal component 1. In still other embodiments, the substitutions with the highest loads can be selected by ranking substitutions in order of their loads. For example, the substitution with the highest "load" can be selected, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 or 100 substitutions with the highest "loads" can be selected. In still other embodiments, the substitutions with the lowest loads can be eliminated by ranking substitutions in order of their loads. For example, the substitution with the lowest "load" can be eliminated, or the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, up to 50, up to 60, up to 70, up to 80, up to 90, up to 100, up to 110, up to 120, up to 130, up to 140, up to 150, up to 160, up to 170, up to 180, up to 190, up to 200, up to 210, up to 220, up to 230, up to 240, up to 250, up to 260, up to 270, up to 280, up to 290, up to 300, up to 310, up to 320, up to 330, up to 340, up to 350, up to 360, up to 370, up to 380, up to 390, up to 400, up to 500, up to 600, up to 700, up to 800, up to 900, up to 1000, up to 2000, up to 3000, up to 4000, up to 5000, up to 6000, up to 7000, up to 8000, up to 9000, up to 10000, up to 12000, up to 14000, up to 16000, up to 18000 or up to 20000substitutions with the lowest "loads" may be eliminated.

5.1.8 Other Exemplary Rules Based Upon Principal Component Analysis of Sequence Alignments All of the scores obtained as described in subsections 5.1.4 through 5.1.7 are just examples of ways in which such values can be calculated. These values can then be combined in one of the ways described in Section 5.1. One skilled in the art will readily appreciate that there are many variations on methods for obtaining quantitative measures of the predicted fitness of a substitution in a antibody in such a way that these values may subsequently be combined. All such variations are included as aspects of the invention.

By combining the scores obtained from the rules used in methods 132 of expert system 100, a set of substitutions can be identified for testing. These may be the substitutions with the highest aggregate scores, they may be the substitutions with the highest score for each individual rule 120, or they may be derived in some other way using the scores produced by the rules 120 used by methods 130 of expert system 100. In some embodiments, the number of substitutions selected by step 03 of FIG. 2 in one cycle of the optimization process is less than 1000 substitutions, more preferably less than 250 substitutions, more preferably less than 100 substitutions and more preferably less than 50 substitutions.

5.2 Design of an Antibody Variant Set

The rules discussed in Section 5.1 above and shown in FIG. 3 are one example of the way in which an initial sequence space can be defined. The sequence space is defined in terms of an initial target antibody sequence, and substitutions to be made in that target sequence. Each substitution is defined in terms of a position in the target antibody, and the identity of a monomer with which the monomer at that position in the target antibody is to be replaced. Selection of the target antibody corresponds to step 01 in FIG. 2. Definition of the sequence space corresponds to step 02 in FIG. 2. This section is directed to step 03 of FIG. 2.

Once an initial set of substitutions has been selected in accordance with Section 5.1, a set of variants incorporating these changes can be designed (the designed antibody variant set). This process corresponds to step 03 in FIG. 2. In preferred embodiments, this designed antibody variant set includes only a subset of the total number of possible variants that could be generated. For example, the total number of possible variant proteins in a sequence space defined by a target antibody containing all possible combinations of 24 substitutions is $2^{24} > 16,000,000$. However the methods of the present invention allow the interrogation of this sequence space by designing and synthesizing only a very small fraction of the total number of antibodies that are included in the sequence space defined by the initial target antibody and the substitutions. In some embodiments, the number of variants in the designed antibody variant set is less than 1000 variants, more preferably less than 250 variants and more preferably less than 100 variants. This is possible because, although the designed antibody variant set includes only a subset of the total number of possible variants (e.g. the possible combinations of substitutions), care is taken to test all antibody substitutions in many different sequence contexts. An example is shown in FIG. 14, where a set of 24 variants were designed to interrogate the sequence space defined by a target antibody sequence and 24 substitutions in FIG. 13. Here, each variant contains six substitutions, each substitution occurs six times within the designed antibody variant set, and each occurrence of each substitution takes place within a quite different context, that is it is combined with a different set of other substitutions each time.

The aim when designing a set of antibody variants to interrogate a sequence space defined by a target antibody sequence and a set of substitutions is to obtain a designed antibody variant set where the substitutions are distributed in such a way that a large amount of information can subsequently be extracted from sequence-activity relationships. In this respect the design of antibody variant sets has common elements with the design of experimental datasets from a diverse range of other disciplines including agriculture and engineering. Methods to optimize experimental datasets (experimental design or design of experiment: DOE) are described by Sir R. A. Fisher in 1920 (Fisher, The Design of Experiments, MacMillan Publishing Company; 9th edition, 1971). Plackett and Burman developed the idea further with the introduction of screening designs (e.g., Plackett et al., 1946, Biometrika 33: 305-325), and Taguchi subsequently introduced the orthogonal matrix (Taguchi, 1986, *Introduction to Quality Engineering*, Asian Productivity Organization, Distributed by American Supplier Institute Inc., Dearborn, Mich.). Any number of experimental design techniques can be used to maximize the information content of the designed antibody variant set including, but not limited to, complete factorial design, $2^k$ factorial design, $2^k$ fractional factorial design, central composite, latin squares, greco-latin squares, Plackett-Burmann designs, Taguchi design, and combinations thereof. See, for example, Box et al., 1978, *Statistics for Experimenters*. New York, Wiley, for examples of such techniques that can be used to construct a designed antibody variant set from the initial set of antibody substitutions selected in accordance with Section 5.1 that tests a maximum number of combinations in a minimal number of antibody variants.

The methods described above were designed to maximize the amount of information that could be obtained from a specified limited number of experiments that could be performed. This is conceptually comparable to the resource limitation seen in antibody optimization, where functional tests are complex and time, cost or other resource-limited. However, a significant difference between antibody optimization and other applications of experimental design is that for antibody optimization there is an additional constraint. In designing antibody variants, the simultaneous introduction of many changes can adversely affect functional properties of the antibody. In contrast to traditional experimental design strategies, it is advantageous in the present invention to reduce the number of previously untested substitutions present in each variant to ten or less, preferably to five or less, more preferably to between 3 and 10. For instance, in some specific embodiments, the number of previously untested substitutions present in each variant is 10, 9, 8, 7, 6, 5, 4 or 3. In other words, in subsequent cycles of steps 02 through 07, less than 10, 9, 8, 7, 6, 5, 4 or 3 new variants are chosen. Here, a variant references to an antibody that has a sequence that is identical to the sequence of the antibody selected in step 01 of FIG. 2 with the exception that there are one or more substitutions in the sequence. Here, a substitution refers to a mutation at a particular position in the antibody from the residue found at that position in the antibody selected in step 01 of FIG. 2 to some other residue.

To design an antibody variant set that will yield useful sequence-activity information upon analysis of the functional properties and sequences of the antibody variants, any method can be appropriate provided that the number of substitutions in each variant set is relatively small so that the majority of antibodies are active. For instance, in preferred embodiments, the number of previously untested substitutions present in each variant is preferably 9, 8, 7, 6, 5, 4, 3 or 2. Furthermore, it is desirable that each selected substitution be tried an approximately equal number of times in the designed antibody variant set. It is further desirable that each substitution be tested in many different sequence contexts. In other words each substitution appears in a number of different antibody variants, in each case being combined with a different set of other substitutions. In FIG. 14 the substitution L180I appears in variant 3 with P97S, E138A, Y194S, A236V, V267I and in variant 18 with N95C, S107D, V167I, G293A, I310K.

A variation of the above method is to require (i) that each substitution identified be tried an approximately equal number of times in the designed antibody variant set, and (ii) that as many different combinations of two substitutions (e.g. substitution pairs) as possible be tested. For example, to test forty substitutions in an antibody it may be desirable to incorporate a maximum of five changes per variant. For forty substitutions there are (40×39/2) 780 possible pairs of substitutions. In one variant with five substitutions there are ten pairs of substitutions. So in forty variants there will be a maximum of 400 substitution pairs. The aim is then to maximize the number of different substitution pairs that are tested and to try to represent each substitution five times. The substitution pairs can be scored with the initial selection algorithm, and the top scoring 400 substitution pairs tested. The solution to such a problem of finding variants with the constraints mentioned here is known as a coverage problem. The coverage problem is NP-hard. Therefore greedy and other forms of approximate solutions are used to solve the NP-hard problems in the present invention. For instance, in some embodiments, the algorithms described in Gandhi et al., 2001, Lecture Notes in Computer Science 2076: 225 are used. In some embodiments, the desired set of sequences can be evolved using monte carlo algorithms and genetic algorithms to maximize the number of pairs in the variant set. Genetic algorithms are described in Section 7.5.1 of Duda et al., 2001, *Pattern Classification*, Second Edition, John Wiley & Sons, Inc., New York, which is hereby incorporated by reference in its entirety. Further, similar algorithms can be used to expand the coverage problem to maximize the number of triplets, quadruplets and so on.

An exemplary code for maximizing the substitution pairs using an evolutionary coverage algorithm is shown below:

Let m be the number of identified substitutions, n be the number of variants to be synthesized, and k be the number of substitutions per variant.

Create n initial variants with k substitutions, each occurring n×k/m times among variants. This can be done randomly or sequentially. This set is not optimal. Then,

```
for 10000 iterations
{
        i. Choose two random variants;
       ii. Choose two random positions;
      iii. Count the number of distinct substitution pairs seen
           among variants;
       iv. Swap the substitutions (if any) at the two positions
           between the two chosen variants;
        v. Check if the number of substitutions per variant is k;
       vi. Check if number of times a given substitution
           occurs among all variants equals n×k/m;
      vii. Count the number of distinct substitution pairs seen
           among variants;
     viii. If the count from vii) is greater than count from iii) and
           v) and vi) are true, accept the changes to the variants
           from step iv), else, dismiss the changes and retain
           original values.
}
```

Alternatively, the set of substitutions can be divided into two or more groups and be used to design variants where each variant contains substitutions from a particular group, for example by dividing the antibody into functional domains such as different complementarity determining regions (CDRs) or framework regions. The substitutions in such a variant can be subject the coverage algorithms with constraints described above. Each group can also be combined with other groups of substitutions to design initial variants and coverage algorithm can be applied to combination of substitution groups. Groups of substitutions can be arrived at using knowledge of antibody domain and/or functional and structural properties of amino acid residues in the antibody. For example we can identify all substitutions based on Section 5.1 and select top scoring ones, and classify them into groups of substitutions based on which domain of the antibody they are present in such as different complementarity determining regions (CDRs) or framework regions. Alternatively, we can also classify substitutions based on the their special location in the protein structure (e.g surface position versus interior positions) based on experimentally determined structure or using prediction algorithms. Alternatively, substitutions can be classified based on their proximity to the binding sites (e.g residues <5 Å from the binding site belong to one class and residues >5 Å from the binding site to another). Constraints to number of substitutions to be designed in a variant from each substitution group can also be added (e.g., no more than two variants from each substitution group). For example, two substitutions can be chosen from the group close to the binding site and three from the group on the surface of the antibody. Such methods differ from typical experimental design or design of experiment (DOE) methods in the fact that no more than five changes in a variant are allowed and the occurrence of the selected pairs is maximized by scoring. Other DOE methods for distributing 40 substitutions would require as many as between 18 and 22 changes in an antibody, which would have a high likelihood of being detrimental to antibody function.

Alternatively or additionally, an antibody variant set can be created stochastically by library synthesis methods such as parallel site-directed mutagenesis, DNA shuffling or other methods for incorporating defined substitutions into an antibody such as those described in Section 5.8. In these instances the variant set contains substitutions distributed at random, so precisely defined variants are not synthesized. Instead, the introduction of substitutions is controlled so that the average number of substitutions incorporated into each variant is between 1 and 10, more preferably the average number of substitutions incorporated into each variant is between 1 and 5. Variants can then be selected at random and the distribution of substitutions can be determined by determining the sequence of the antibody. In some embodiments of the invention less than 1000 variants created by library synthesis methods are synthesized and sequenced, preferably less than 500 variants created by library synthesis methods are synthesized and sequenced, more preferably less than 250 variants created by library synthesis methods are synthesized and sequenced, even more preferably less than 100 variants created by library synthesis methods are synthesized and sequenced. In some embodiments that use libraries, the creation of a library can be simulated using computational modeling of shuffling and other methods. See, for example, Moore, 2001, Proc Natl Acad Sci USA 13, 3226-3231; Moore and Maranas, 2000, J Theor Biol. 205, pp. 483-503.

Once the antibody variant set has been designed, the variants are synthesized using methods known in the art. Representative, but nonlimiting synthetic methods are described in Section 5.8, below. Then the antibodies are tested for relevant biological properties. Such relevant biological properties include, but are not limited to antibody solubility and activity. Nonlimiting examples of how such antibody activity can be tested are described in Section 5.9 below. Together the synthesis and testing of the antibody variants represent step 04 in FIG. 2.

5.3 Methods for Mapping a Sequence Space to a Function Space

Once substitutions have been selected using expert system 100 (FIG. 2, step 04), and variants have been designed, synthesized and tested for one or more activity or function, it is desirable to use the sequence and activity information from the designed antibody variant set to assess the contributions of substitutions to the one or more antibody activity or function. This process is represented as step 05 in FIG. 2. Assessment of the contributions of substitutions to one or more antibody function can be performed by deriving a sequence-activity relationship. Such a relationship can be expressed very generally, for example as shown in Equation 3

$$Y=f(x_1, x_2, \ldots, x_i)$$ (Eq 3)

where,

Y is a quantitative measure of a property of the antibody (e.g., activity), $x_i$ is a descriptor of a substitution, a combination of substitutions, or a component of one or more substitutions in the sequence of the antibody, and f( ) is a mathematical function that can take several forms.

A model of the sequence-activity relationship can be described as a functional form whose parameters have been trained for the input data (Y and $x_i$). Protein sequences can be mathematically represented in terms of many variables (descriptors, predictors), each variable representing the type of amino acid at a specific location (linear form in terms of the position of the amino acid). For example, the sequence AGWRY can be represented by five variables, where variable one assumes a value of "A" corresponding to position 1, variable two is "G" corresponding to position two and so on. Each variable can assume 1 of 20 possibilities. Alternatively, each variable can also represent multiple positions (say two) and assume 1 of 400 values (for 2 positions) corresponding to 20×20=400 combination of possible amino acid pairs. For example, a variable can describe position one and two and assume a value of "AG" (thereby creating a variable that in non-linear in terms of position of the amino acid). Alternatively, each position can assume a value corresponding to a physico-chemical property of the amino acid instead of amino acid identity. For example, the position can be described in terms of the mass of the amino acid at that location. For the sequence AGWRY, a variable for position one can assume the value 71.09 and position two 57.052 and so on. Alternatively, each position can be described by one or several principal components derived to represent many physico-chemical properties of the amino acid present in that position. Alternatively, each variable can be a combination of variables representing properties of amino acids. Alternatively, each variable can be represented in a binary form corresponding to presence or absence of a particular amino acid. For example, consider two variants AGWRY and AKWRY, Position two can be "1" if G is present at that position and "0" if it is absent and the descriptor for that position can have the value "0" or "1." Alternatively, each variable can be represented in a binary form corresponding to presence or absence of a defined group of amino acids.

In equation 3, the functional form f( ) correlates descriptors of an antibody sequence ($x_i$) to its activity. In a simple embodiment of the invention, the function f can be a linear combination of $x_i$:

$$Y=w_1x_1+w_2x_2+\ldots+w_ix_i$$ (Eq. 5)

where $w_i$ is a weight (or coefficients of $x_i$).

In some embodiments, to derive a sequence-activity relationship, a set of descriptors ($x_i$) that can describe all of the substitutions within the antibody variant set is identified. Values of Y for each member of the antibody variant set are measured. Values for each weight ($w_i$) are then calculated such that the differences between values predicted for each value of Y by Equation 3 and those observed experimentally are minimized for the antibody variants set, or for a selected subset of such antibody variants.

The minimization step above can also use weights for different activity predictions and, in general, can use a loss function. In one embodiment this loss function can be squared error loss, where weights that minimize the sum of squares of the differences between predicted and measured values for the dataset are computed.

In some embodiments statistical regression methods are used to identify relationships between dependent ($x_i$) and independent variables (Y). Such techniques include, but are not limited to, linear regression, non-linear regression, logistic regression, multivariate data analysis, and partial least squares regression. See, for example, Hastie, *The Elements of Statistical Learning*, 2001, Springer, New York; Smith, *Statistical Reasoning*, 1985, Allyn and Bacon, Boston. In one embodiment, regression techniques like the PLS (Partial Least Square) can be used to solve for the weights ($w_i$) in the equation X. Partial Least Squares (PLS) is a tool for modeling linear relationships between descriptors. The method is used to compress the data matrix composed of descriptors (variables) of variant sequences being modeled into a set of latent variable called factors. The number of latent variable is much smaller than the number of variables (descriptors) in the input sequence data. For example, if the number of input variable is 100, the number of latent variables can be less than 10. The factors are determined using the nonlinear iterative partial least squares algorithm. The orthogonal factor scores are used to fit a set of activities to the dependent variables. Even when the predictors are highly collinear or linearly dependent, the method finds a good model. Alternative PLS algorithms like the SIMPLS can also be used for regression. In such methods, the contribution to the activities from every variable can be deconvoluted to study the effect of sequence on the function of the antibody.

In some embodiments, modeling techniques are used to derive sequence-activity relationships. Such modeling techniques include linear and non-linear approaches. Linear and non-linear approaches are differentiated from each other based on the algebraic relationships used between variables and responses in such approaches. In the system being modeled, the input data (e.g., variables that serve as descriptors of the antibody sequence), in turn, can be linearly related to the variables provided or non-linear combinations of the variables. It is therefore possible to perform different combinations of models and data-types: linear input variables can be incorporated into a linear model, non-linear input variables can be incorporated into a linear model and non-linear variables can be incorporated into a non-linear model.

Many functional forms of f( ) (Eqn. 3) can be used and the functional form can be combined using weights defined in the knowledge base 108 for analysis. For example, Function f( ) can assume non-linear form. An example of non-linear functional form is:

$$Y = w_{12} * x_1 * x_{2+} w_{123} * x_1 * x_{3+} \ldots + w_{nn} * x_n * x_n.$$

Non-linear functions can also be derived using modeling techniques such as machine learning methods. For example, the sequence($x_i$)-activity(Y) data to predict the activities of any sequence given the descriptors for a sequence can be determined using neural networks, Bayesian models, generalized additive models, support vector machines, classification using regression trees.

The data describing variants of the initial antibody can be represented in many forms. In some embodiments, all or a portion of the data is represented in a binary format. For example, representing the presence or absence of a specified residue at a particular position by a "1" or a "0" constitutes a linear binary variable. In another example, representing the presence of a specified residue at one position AND a second specified residue at a second position by a "1" constitutes a non-linear binary variable. In some embodiments, all or a portion of the data is represented as Boolean operators. In some embodiments, all or a portion of the data is represented as principal component descriptors derived from a set of properties. See, for example, Sandberg et al., 1998, J Med Chem. 41, 2481-91. Antibody input sequence data can also use descriptors based on comparison with a sequence profile (e.g., a hidden Markov model, or principal component analysis of a set of sequences). For example in FIG. 9, PC1 and PC2 values of the sequences can be used as descriptors for the sequences in that figure. In addition, any number of principle components can be used as descriptors. See, for example, Casari et al., 1995, Nat Struct Biol. 2:171-8; and Gogos et al., 2000, Proteins 40:98-105.

To initiate step 05 (FIG. 2), the antibody sequence data in the designed set and the results of the assays performed on the designed set are converted to a form that can be used in pattern classification and/or statistical techniques in order to identify relationships between the results of the assays and the substitutions present in the designed set. In general, such conversion involves a step in which independent variables and dependent variables are enumerated. Here, the independent variables are the various substitutions (mutations) that are present in the designed set. The dependent variables are the results of assays, such as those described in Section 5.9.

Each substitution can be considered independently. The presence or absence of a substitution or residue at a specific position can be used to describe one or more of the independent variables. The presence or absence of two or more substitutions or residues at two or more specific positions can be used to describe one or more of the independent variables. One or more physico-chemical descriptors of a substitution or residue at a specific position can be used to describe one or more of the independent variables. One or more physico-chemical descriptors of two or more substitutions or residues at two or more specific positions can be used to describe one or more of the independent variables. Then, pattern classification and/or statistical techniques are used to identify relationships between particular substitutions, or combinations of substitutions, and the assay data.

In some embodiments, supervised learning techniques are used to identify relationships between mutations in the designed set and antibody properties identified in assays results such as assays performed in Section 5.9. Such supervised learning techniques include, but are not limited to, Bayesian modeling, nonparametric techniques (e.g., Parzen windows, $k_n$-Nearest-Neighbor algorithms, and fuzzy classification), neural networks (e.g., hopfield network, multilayer neural networks and support vector machines), and machine learning algorithms (e.g., algorithm-independent machine learning). See, for example, Duda et al., *Pattern Classification*, $2^{nd}$ edition, 2001, John Wiley & Sons, Inc. New York; and Pearl, *Probabilistic Reasoning in Intelligent Systems: Networks of Plausible Inference*, Revised Second Printing, 1988, Morgan Kaufmann, San Francisco. For example, the sequence ($x_i$)-activity (Y) data can be sed to predict the activities of any sequence given the descriptors for a sequence using a neural network. The input for the network is the descriptors and the output is the predicted value of Y. The weights and the activation function can be trained using supervised decision based learning rules. The learning is performed on a subset of variants called the training set and performance of the network is evaluated on a test set.

In some embodiments, unsupervised learning techniques are used to identify relationships between mutations in the designed set and antibody properties identified in assays results such as assays performed in Section 5.9. Such unsupervised learning techniques include, but are not limited to stochastic searches (e.g., simulated annealing, Boltzmann learning, evolutionary methods, principal component analysis, and clustering methods). See, for example, Duda et al., *Pattern Classification, $2^{nd}$* edition, 2001, John Wiley & Sons, Inc. New York. For example, the weights in equation 5 can be adjusted by using monte carlo and genetic algorithms. The optimization of weights for non-linear functions can be complicated and no simple analytical method can provide a good solution in closed form. Genetic algorithms have been successfully used in search spaces of such magnitude. Genetic algorithms and genetic programming techniques can also be used to optimize the function form to best fit the data. For instance, many recombinations of functional forms applied on descriptors of the sequence variants can be applied.

In some embodiments, boosting techniques are used to construct and/or improve models developed using any of the other techniques described herein. A model of the sequence-activity relationship can be described as a functional form whose parameters have been trained for the input data (Y and $x_i$). Many algorithms/techniques to build models have been described. Algorithms applied on a specific dataset can be weak in that the predictions can be less accurate or "weak" (yielding poor models). Models can be improved using boosting techniques. See, for example, Hastie et al., *The Elements of Statistical Learning*, 2001, Springer, New York. The purpose of boosting is to combine the outputs of many "weak" predictors into a powerful "committee." In one embodiment of the invention, boosting is applied using the AdaBoost algorithm. Here, the prediction algorithm is sequentially applied to repeatedly modified versions of the data thereby producing a sequence of models. The predictions from all of these models are combined through a weighted majority vote to produce the final prediction. The data modification at each step consists of applying weights ($W^b_i$) to each of the i training observations. Initially weights are set to 1/N, where N is the number of training observation (sequence-activity data). The weights are modified individually in each successive iteration. Training observations that were predicted poorly by a particular model have their weights increased and training observations that were predicted more accurately have their weights decreased. This forces each successive model to concentrate on those training observations that are issued by the previous model. The step of combining the models to produce a "committee" assigns a weight to each model based on the overall prediction error of that model.

The various modeling techniques and algorithms described herein can be adapted to derive relationships between one or more desired properties or functions of an antibody and therefore to make multiple predictions from the same model. Modeling techniques that have been adapted to derive sequence-activity relationships for antibodies are within the scope of the present invention. Some of these methods derive linear relationships (for example partial least squares projection to latent structures) and others derive non-linear relationships (for example neural networks). Algorithms that are specialized for mining associations in the data are also useful for designing sequences to be used in the next iteration of sequence space exploration. These modeling techniques can robustly deal with experimental noise in the activity measured for each variant. Often experiments are performed in replicates and for each variant there will be multiple measurements of the same activity. These multiple measurements (replicate values) can be averaged and treated as a single number for every variant while modeling the sequence-activity relationship. The average can be a simple mean or another form of an average such as a geometric or a harmonic mean. In the case of multiple measurements, outliers can be eliminated. In addition, the error estimation for a model derived using any algorithm can incorporate the multiple measurements through calculating the standard deviation of the measurement and comparing the predicted activity from the model with the average and estimate the confidence interval within which the prediction lies. Weights for observations to be used in models can also be derived from the accuracy of measurement, for example, through estimating standard deviation and confidence intervals. This procedure can put less emphasis on variants whose measurements are not accurate. Alternatively, these replicate values can be treated independently. This will result in duplicating the sequences in the dataset. For example, if sequence variant i represented by descriptor values $\{x_j\}^{i1}$ has been measured in triplicates ($Y_{i1}$, $Y_{i2}$, $Y_{i3}$), the training set for modeling will include descriptor value $\{x_j\}^{i2}$ with activity $Y_{i2}$ and $\{x_j\}^{i3}$ with activity $Y_{i3}$ in addition to $\{x_j\}^{i1}$ with activity $Y_{i1}$, where $\{x_j\}^{i1} = \{x_j\}^{i2} = \{x_j\}^{i3}$.

A representative modeling routine in accordance with one embodiment of the invention comprises the following steps.

Step 302. Relevant descriptors of the monomeric variables are identified. These descriptors can convey physico-chemical properties relevant to the interaction between biomolecules or classify the monomers (residues) as discreet entities represented in binary form as described earlier. The former is preferred for residue positions in the antibody sequence where the number of different amino acid substitutions is four or more or where the variables can assume one of four possible values for those positions and the physico-chemical properties values are well distributed (e.g.) different from each other. The latter is preferred for positions that have four or less possible values for the relevant variable, and/or the values are clustered (e.g.) are not very different from each other. To create non-linear variables, new variables are formed that are a combination of monomeric variables. For example, consider two variants AGWRY and AKYRY. The linear binary form of the variable (descriptor) for position 2 assumes a value of "1" if G is present at that position and "0" if it is absent. Alternatively, a non-linear variable can be created in addition to the linear variables describing each position. In the above example, a new non-linear variable representing position "2" and "3" can assume four values in numeric form. In one form, the variable can assume a value of 11 for "GW", 10 for "GY", 01 for "KW" and 00 for "KY". In other representations of binary non-linear variable, four variables can describe position 2 and 3, where variable one assumes a value of "1" if the sequence at position 2 and 3 is "GW" and "0" otherwise and the second variable takes the values of "1" or "0" if the sequence is "GY" or otherwise and so on.

In some embodiments it is advantageous to identify regions and thereby variables based on factors including, but not limited to, structures, domains, motifs and exons, optionally using expert system 100 to do so, in order to weigh different variables and their contribution to the model or to build sequence activity models based on these factors. For example, a weight of "1" can be assigned to variables in the heavy chain of the antibody and "0" for variables in light chain of the antibody when modeling activity $Y_1$ and a weight of "0" can be assigned to variables in heavy chain and "1" for light chain when modeling activity $Y_2$. This weighting can also incorporate constraints such as immunogenicity and other functional considerations that may or may not be measured in experiments, but which can be fully or partially predicted using computational techniques. For example, a negative weight can be assigned to appearance of a T-cell epitope in a variant, or removal of glycosylation sites.

Step 304. In step 304 the parameters for the functional form of the sequence-activity relationship are optimized to obtain a model by minimizing the difference between the predicted values and real values of the activity of the antibody. Such optimization adjusts the individual weights for each of the descriptors identified in preceding steps using a refinement algorithm such as least squares regression techniques. Other methods that use alternative loss functions for minimization can be used to analyze any particular dataset. For example, in some antibody sequence-activity data sets, the activities may not be distributed evenly throughout the measured range. This will skew the model towards data points in the activity space that are clustered. This can be disadvantageous because datasets often contain more data for antibody variants with low levels of activity, so the model or map will be biased towards accuracy for these antibodies that are of lower interest. This skewed distribution can be compensated for by modeling using a probability factor or a cost function based on expert knowledge. This function can be modeled for the activity value or can be used to assign weights to data points based on their activity. As an example, for a set of activities in the range of 0 to 10, transforming the data with a sigmoidal function centered at five will give more weight to sequences with activity above five. Such a function can optionally also be altered with subsequent iterations, thereby focusing the modeling on the part of the dataset with the most desired functional characteristics. This approach can also be coupled with exploring techniques like a Tabu search, where undesired space is explored with lower probabilities.

In some embodiments, algorithms that optimize the sequence-activity model for the dataset by randomly starting with a solution (e.g., randomly assigning weights $w_i$) and using methods like hill-descent and/or monte-carlo and/or genetic algorithm approaches to identify optimal solutions.

In embodiments directed to antibody engineering, robustness of the models used is a significant criterion. Thus, obtaining several sub-optimal solutions from various initial conditions and looking at all the models for common features can be a desirable methodology for ensuring the robustness of the solution. Another way to obtain robust solutions is to create bootstrap data sets based on the input data, than estimate a p-value or confidence on the various coefficients of the model. In addition boosting techniques like AdaBoost can be used to obtain a "committee" based solution.

Step 306. Many mathematical modeling techniques for deriving a sequence-activity correlation are evaluated. Preferred mathematical modeling techniques used to identify and capture the sequence-activity correlation handle (i) very large numbers of variables (e.g 20 or more) and correlations between variables, (ii) linear and non-linear interactions between variables, and (iii) are able to extract the variables responsible for a given functional perturbation for subsequent testing of the mathematical model (e.g., models should be easily de-convoluted to assign the effect of variables describing the amino acids substitution with activities).

Step 308. In step 308 the coefficients (parameters) of the model(s) are deconvoluted to see which amino acid substitutions (variables/descriptors of the variants) influence the activity of the antibody. It can be important to identify which descriptors of the antibody are important for the activity of interest. Some of the techniques, such as partial least squares regression (SIMPLS) that uses projection to latent structures (compression of data matrix into orthogonal factors) may be good at directly addressing this point because contributions of variables to any particular latent factors can be directly calculated. See, for example, Bucht et al., 1999, Biochim Biophys Acta. 1431:471-82; and Norinder et al., 1997, J Pept Res 49:155-62. Other methods such as neural networks can learn from the data very well and make predictions about the activity of entire antibodies, but it may be difficult to extract information, such as individual contributing features of the antibody from the model. Modeling techniques/methods that directly correlate the amino acid variations to the activity are preferred because we can derive the sequence-activity map (relationship) to construct new variants not in dataset that have preferentially higher activities. These methods can be adapted to provide a direct answer and output in desired forms.

Step 310. In step 310 the models developed using various algorithms and methods in the previous step can be evaluated by cross validation methods. For example, by randomly leaving data out to build a model and making predictions of data not incorporated into the model is a standard technique for cross validation. In some instances of antibody engineering, data may be generated over a period of months. The data can be added incrementally to the modeling procedure as and when such data becomes available. This can allow for validation of the model with partial or additional datasets, as well as predictions for the properties of antibody sequences for which activities are still not available. This information may then be used to validate the model.

An example of internal model validation methods is shown in FIGS. 4 and 5. In these schemes a confidence score for each regression coefficient or weight vector can be generated for any antibody sequence-activity model.

For example, in one embodiment of the present invention, average values for weight functions can be obtained by omitting a part of the available data. Either individual sequences and their associated activities or individual substitution positions can be left out. A sequence-activity relationship can then be constructed from this partial data. This process can be repeated many times, each time the data to leave out is selected randomly. Finally an average and range of values for each weight function is calculated. The weight functions can then also be ranked in order of their importance to activity.

To assess the probability that a substitution is associated with an activity by random chance, the same weight function calculations can be performed when the sequences and activities are randomly associated (FIG. 5). In this case there should be no relationship between sequence and function, so weight functions arise only by chance. A measure of the confidence for the weight function can then be calculated. It is related to the number of standard deviations by which the value calculated when sequences and activities are correctly associated exceeds the value calculated when they are randomly associated. The above methods on model assessment, model inference and averaging are discussed in detail by Hastie et al., 2001, Springer Verlag, series in statistics.

Step 312. In step 312 new antibody sequences that are predicted to possess one or more desired property are derived. Alternatively it can be desirable to rank order the input variables for detailed sequence-activity correlation measures. The model can be used to propose sequences that have high probabilities of being improved. Such sequences can then be synthesized and tested. In one embodiment, this can be achieved if the effects of various sequence features of the antibodies on their functions are known based on the modeling. Alternatively, for methods like neural networks, $10^3$ or $10^6$ or $10^9$ or $10^{12}$ or $10^{15}$ or $10^{18}$ or as many as $10^{80}$ sequences can be evaluated in silico. Then those predicted by the model to possess one or more desired properties are selected.

Step 314. The statistical quality of the model fit to the input data is evaluated in step 314. Validation of sequence-activity correlation can be internal, using cross-validation of the data, or preferably external, by forecasting the functional perturbation of a set of new sequences derived from the model. Sequences with predicted values of their functional perturbations are then physically made and tested in the same experimental system used to quantify the training set. If the sequence-activity relationship of the dataset is satisfactory quantified using internal and external validation, the model can be applied to a) predict the functional value of other related sequences not present in the training set, and b) design new sequences within the described space that are likely to have a function value that is outside or within the range of function given by the training set.

The initial set of data can be small, so models built from it can be inaccurate. Initial models may not contain terms to account for amino acid interactions. Others have found that amino acid changes within an antibody are approximately additive and few interaction terms are required to describe the effects of mutations on protein function. See, for example, Aita et al. (2000) Biopolymers 54: 64-79; Aita et al. (2001) Protein Eng 14: 633-8; Choulier et al. (2002) Protein Eng 15:

373-82; and Prusis et al. (2002) Protein Eng 15: 305-11. However such interactions can be important and can result in a variant that incorporates all beneficial changes having low activity (Aita et al. (2002) Antibodies 64: 95-105) Improving the modeled relationship further depends upon obtaining better values for weights whose confidence scores are low. To obtain this data, additional variants designed as described in Section 5.4 below will provide additional data useful in establishing more precise sequence-activity relationships.

The output from each method for modeling a sequence-activity relationship can be one or more of: (i) a regression coefficient, weight or other value describing the relative or absolute contribution of each substitution or combination of substitutions to one or more activity of the antibody, (ii) a standard deviation, variance or other measure of the confidence with which the value describing the contribution of the substitution or combination of substitutions to one or more activity of the antibody can be assigned, (iii) a rank order of preferred substitutions, (iv) the additive & non-additive components of each substitution or combination of substitutions, (v) a mathematical model that can be used for analysis and prediction of the functions of in silico generated sequences, (vi) a modification of one or more inputs or weights used by an expert system 100 to select substitutions or (vii) a modification of the methods used by expert system 100 to design an antibody variant set.

5.3.1 Methods for Combining the Results from Two or More Sequence-Activity Relationship Modeling Methods.

It will be appreciated by one skilled in the art that each different method for deriving relationships between antibody sequences and activities can differ in the precise values of their outputs. In some embodiments of the invention it is therefore desirable to combine the outputs from two or more such methods for subsequent uses. This corresponds to step 06 in FIG. 2. There are a variety of ways in which such outputs can be combined. In some embodiments, each output can be independently applied to the subsequent design of antibody variants (FIG. 2, step 07) or the modification of parameters or weights used by expert system 100 for the selection of substitutions (FIG. 2 step 02) or the design of antibody variant sets (FIG. 2 step 03). In some embodiments, average values (or some other mathematical function of two or more values derived by two or more sequence-activity models) can be calculated for the regression coefficient, weight or other value describing the relative or absolute contribution of each substitution or combination of substitutions to one or more activity of the antibody (e.g., as defined in Equation 4 below). In some embodiments, the standard deviation, variance or other measure of the confidence with which the value describing the contribution of the substitution or combination of substitutions to one or more activity of the antibody can be assigned (e.g., as defined in Equation 4 below). In some embodiments, the rank order of preferred substitutions is used to combine the methods. In some embodiments, the additive (linear variables) and non-additive components (non-linear variables) of each substitution or combination of substitutions is combined:

$$V_{ix} = f(M_1(i_x), M_2(i_x), \ldots, M_j(i_x)) \quad \text{(Eq. 6)}$$

where, $V_{ix}$ is a combined measure of one of the descriptors measuring the performance of an antibody in which monomer x is substituted at position i;

$M_j(i_x)$ is a measure of one of descriptors measuring the performance of an antibody in which monomer x is substituted at position i, determined by sequence-activity correlating method j ($M_j(i_x)$ is the contribution of $i_x$ as determined by Model j); and f( ) is some mathematical function.

The methods used to derive sequence-activity relationships can be chosen or modified such that they better predict the performance of individual substitutions within a combination of other substitutions in an antibody, as described in more detail in Subsection 5.4.4.

5.4 Use of Sequence-Activity Relationships to Design Optimized Variants or Additional Variant Sets There are many ways to use the results of sequence-activity correlations described in Section 5.3 in the design of a subsequent set of variants. This corresponds to step 07 of FIG. 2. Conceptually, this step is similar to the processes corresponding to steps 02 and 03 in FIG. 2. It involves defining a sequence space in terms of an antibody sequence and a set of substitutions, then designing a set of antibody variants that incorporate those substitutions in different combinations.

5.4.1 Definition of the Sequence Space to Represent Additional Variant Sets

A few methods for defining a sequence space for an optimized variant or additional variant set, using an antibody sequence and a set of substitutions are enumerated here by way of examples not intended to limit the scope of the present invention.

In one embodiment the sequence space can be defined in terms of the original target antibody sequence and substitutions that have already been tested. In preferred embodiments of the invention, this method for defining the sequence space is used if the desired degree of further increase in one or more activity of the antibody is less than 10-fold, preferably less than 5-fold, more preferably less than 2-fold.

In another embodiment, the sequence space can be defined in terms of the original target antibody sequence and a combination of substitutions that have already been tested and those that have not yet been tested. In preferred embodiments of the invention, this method for defining the sequence space is used if the desired degree of further increase in one or more activity of the antibody is greater than 2-fold, preferably greater than 5-fold, and more preferably greater than 10-fold.

In still another embodiment, the sequence space can be defined purely in terms of the original target antibody sequence and substitutions that have not yet been tested. This method for defining the sequence space is generally most appropriate for the initial variant set as represented in FIG. 2 step 02.

5.4.2 Assessment of Previously Tested Substitutions for Incorporation into Optimized Variants or Additional Variant Sets The methods for selecting substitutions that have not previously been tested have been described in Section 5.1. Methods for selecting or eliminating substitutions that have previously been tested use one or more of the outputs from the methods for correlating antibody sequences with their activities. A few methods for defining a sequence space for an optimized variant or additional variant set, using an antibody sequence and a set of substitutions are enumerated here by way of examples. In the following examples, the term "substitution" can also mean a pair or larger group of substitutions (for example, when the descriptors of antibodies are represented in non-linear form as described in section 5.3), since sequence-activity relationships can produce regression coefficients, weights or other measurements of contribution to function and confidences for these measurements that apply not to individual substitutions but to specific combinations of these substitutions.

(i) A substitution can be selected if it has a positive regression coefficient, weight or other value describing its relative or absolute contribution to one or more activity of the antibody.

(ii) A substitution can be selected if it has a positive regression coefficient, weight or other value describing its relative or absolute contribution to one or more activity of the antibody, and it is at least one standard deviation, preferably two standard deviations or more preferably three standard deviations above neutrality.

(iii) A substitution can be selected if it has a positive regression coefficient, weight or other value describing its relative or absolute contribution to one or more activity of the antibody, and it has also been tested at least once, preferably at least twice, more preferably at least 3 times, more preferably at least 4 times, even more preferably at least 5 times.

(iv) A substitution can be selected if it has a positive regression coefficient, weight or other value describing its relative or absolute contribution to one or more activity of the antibody, and it is at least one standard deviation, preferably two standard deviations or more preferably three standard deviations above neutrality, and it has also been tested at least once, preferably at least twice, more preferably at least 3 times, more preferably at least 4 times, even more preferably at least 5 times.

(v) A substitution can be selected from a rank ordered list of substitutions. For example the most favorable substitution may be selected, or the 2, 3, 4, 5, 6, 7, 8, 9, 10, 11, 12, 13, 14, 15, 16, 17, 18, 19 or 20 most favorable substitutions can be selected.

(vi) A substitution can be selected from a rank ordered list of substitutions. For example, the most favorable substitution can be selected, or the 2, 3, 4, 5, 6, 7, 8, 9, 10, 11, 12, 13, 14, 15, 16, 17, 18, 19 or 20 most favorable substitutions can be selected, and it is at least one standard deviation, preferably two standard deviations or more preferably three standard deviations above neutrality.

(vii) A substitution can be selected from a rank ordered list of substitutions. For example, the most favorable substitution can be selected, or the 2, 3, 4, 5, 6, 7, 8, 9, 10, 11, 12, 13, 14, 15, 16, 17, 18, 19 or 20 most favorable substitutions can be selected, and it has also been tested at least once, preferably at least twice, more preferably at least 3 times, more preferably at least 4 times, even more preferably at least 5 times.

(viii) A substitution can be selected from a rank ordered list of substitutions. For example, the most favorable substitution may be selected, or the 2, 3, 4, 5, 6, 7, 8, 9, 10, 11, 12, 13, 14, 15, 16, 17, 18, 19 or 20 most favorable substitutions can be selected, and it is at least one standard deviation, preferably two standard deviations or more preferably three standard deviations above neutrality, and it has also been tested at least once, preferably at least twice, more preferably at least 3 times, more preferably at least 4 times, even more preferably at least 5 times.

(ix) A substitution can be selected if it has a negative regression coefficient, weight or other value describing its relative or absolute contribution to one or more activity of the antibody, and it is less than three standard deviations, preferably less than two standard deviations or more preferably less than one standard deviation below neutrality.

(x) A substitution can be selected if it has a negative regression coefficient, weight or other value describing its relative or absolute contribution to one or more activity of the antibody, and it has also been tested no more than 5 times, preferably no more than 4 times, more preferably no more than 3 times, more preferably no more than twice, even more preferably no more than once.

(xi) A substitution can be selected if it has a negative regression coefficient, weight or other value describing its relative or absolute contribution to one or more activity of the antibody, and it is less than three standard deviations, preferably less than two standard deviations or more preferably less than one standard deviation below neutrality, and it has also been tested no more than 5 times, preferably no more than 4 times, more preferably no more than 3 times, more preferably no more than twice, even more preferably no more than once.

(xii) A substitution can be eliminated if it has a negative regression coefficient, weight or other value describing its relative or absolute contribution to one or more activity of the antibody.

(xiii) A substitution can be eliminated if it has a negative regression coefficient, weight or other value describing its relative or absolute contribution to one or more activity of the antibody, and it is at least one standard deviation, preferably two standard deviations or more preferably three standard deviations above neutrality.

(xiv) A substitution can be eliminated if it has a negative regression coefficient, weight or other value describing its relative or absolute contribution to one or more activity of the antibody, and it has also been tested at least once, preferably at least twice, more preferably at least 3 times, more preferably at least 4 times, even more preferably at least 5 times.

(xv) A substitution can be eliminated if it has a negative regression coefficient, weight or other value describing its relative or absolute contribution to one or more activity of the antibody, and it is at least one standard deviation, preferably two standard deviations or more preferably three standard deviations above neutrality, and it has also been tested at least once, preferably at least twice, more preferably at least 3 times, more preferably at least 4 times, even more preferably at least 5 times.

5.4.3 Methods for Designing Antibody Variant Sets Incorporating Previously Tested Substitutions Antibody variants that combine or eliminate previously tested substitutions can serve at least two purposes. First, they can be used to obtain antibody variants that are improved for one or more property, activity or function of interest. Generally, though not exclusively, substitutions selected according to criteria (i)-(viii) in subsection 5.4.2 are most likely to be appropriate for this purpose. Second, they can be used to obtain additional information relating the sequence to the activity of an antibody, thereby improving the accuracy with which predictions can be made concerning the effect of substitutions upon one or more property, activity or function of an antibody. Generally, though not exclusively, substitutions selected according to criteria (i)-(xi) in subsection 5.4.2 are most likely to be appropriate for this purpose.

The following methods can be used to design antibody variants containing combinations of substitutions selected by one or more of the methods described in subsection 5.4.2.

Method 1. An antibody that has previously been tested for the one or more property, activity or function of interest is selected. In preferred embodiments the selected antibody has one of the 100 highest experimentally measured scores for the property, activity or function of interest, more preferably one of the 50 highest experimentally measured scores, even more preferably one of the 25 highest experimentally measured scores, even more preferably one of the 10 highest experimentally measured scores.

The substitutions in the selected antibody are combined with one or more substitutions selected by one or more of the methods described in subsection 5.4.2. In preferred embodiments less than 10 selected substitutions are used, more preferably less than 5 selected substitutions are used, even more preferably less than 3 selected substitutions are used.

Method 2. An antibody that has previously been tested for the one or more property, activity or function of interest is selected. In preferred embodiments the selected antibody has one of the 100 highest experimentally measured scores for the property, activity or function of interest, more preferably one of the 50 highest experimentally measured scores, even more preferably one of the 25 highest experimentally measured scores, even more preferably one of the 10 highest experimentally measured scores.

The substitutions in the selected antibody are combined with one or more substitutions selected by one or more of the methods described in subsection 5.4.2. In preferred embodiments less than 10 selected substitutions are used, more preferably less than 5 selected substitutions are used, even more preferably less than 3 selected substitutions are used. In addition, these substitutions are combined with one or more substitutions selected by one or more method described in Section 5.1 (i.e., by the methods used in step 03 of FIG. 2). In preferred embodiments, less than 10 of these last selected substitutions are used, more preferably less than 5 of these last selected substitutions are used, even more preferably less than 3 of these last selected substitutions are used.

Method 3. Two or more substitutions identified by one or more of the methods described in subsection 5.4.2 are selected. In preferred embodiments less than 100 selected substitutions, more preferably less than 50, and even more preferably less than 25 are used. One or more antibody variants containing these substitutions are designed using the methods described in Section 5.2.

Method 4. One or more substitutions selected by one or more of the methods described in subsection 5.4.2 are selected. In preferred embodiments less than 100 selected substitutions, more preferably less than 50, and even more preferably less than 25 are used. One or more substitutions are selected using one or more of the methods described in Section 5.1. In preferred embodiments, less than 100, and more preferably less than 50 of these selected substitutions are used. Then, one or more antibody variants are designed using the methods described in Section 5.2.

Method 5. One or more substitutions selected by one or more of the methods described in subsection 5.4.2 that contribute most positively to the property (e.g., function, activity of interest) are selected. In preferred embodiments, between 1 and 20 most positive substitutions are selected. One or more antibody variant that has already been tested for the property is selected. In preferred embodiments, the between 1 and 20 most active antibodies are selected. One or more of the selected substitutions is added to each of the one or more selected antibodies. In preferred embodiments, the number of substitution positions to be added to each antibody variant sequence is between 1 and 10, more preferably between 1 and 6, and even more preferably between 1 and 3.

Method 6. Substitutions whose regression coefficients, weights or other values describing the relative or absolute contribution to one or more activity of the antibody are positive are selected. Those substitutions whose regression coefficients, weights or other values describing the relative or absolute contribution to one or more activity of the antibody have confidences within a threshold distance from the randomized average weight for that substitution are eliminated. In preferred embodiments, this threshold distance is within 1 standard deviation, more preferably within 2 standard deviations. The substitutions with positive weights and high confidences are combined into a single variant. Alternatively, the selected substitutions are used to design a set of antibody variants as described in Section 5.2.

Method 7. Substitutions are ranked in the order in which confidences can be assigned to regression coefficients, weights or other values describing the relative or absolute contribution to one or more activity of the antibody. The substitutions with lowest confidence scores are selected. From the sequences of antibody variants whose activities have already been measured, those that have high values for the property of interest are selected. In preferred embodiments, between 1 and 20 tested antibody variant sequences with highest activities are selected. One or more of the selected substitutions is added to each selected variant. In preferred embodiments, the number of substitutions to be added to each antibody variant sequence is between 1 and 10, more preferably between 1 and 6, and even more preferably between 1 and 3.

Method 8. One or more antibody variants that have already been tested for the property of interest are selected. In preferred embodiments, between 1 and 20 most active antibodies are selected. One or more substitutions for which a contribution to the property has been calculated are selected. For each of the one or more selected antibodies, the following process is performed. One of the selected substitutions is added or removed and the predicted activity of the resultant antibody is calculated using one or more models for sequence-activity relationship as described in the section 5.3. Exemplary models include, but are not limited to (i) regression techniques that provide regression coefficients for the descriptors, (ii) models that generate weights or other value describing the relative or absolute contribution of each substitution or combination of substitutions to one or more activity of the antibody, (iii) models that provide standard deviation, variance or other measures of the confidence with which the value describing the contribution of the substitution or combination of substitutions to one or more activity of the antibody can be assigned, (iv) models that rank order preferred substitutions, (v) models that provide additive and non-additive components of each substitution or combination of substitutions, (vi) analytical mathematical models that can be used for analysis and prediction of the functions of in silico generated sequences (vii) supervised and unsupervised machine learning techniques like neural networks that can predict the activity of new antibody sequences expressed in terms of the descriptors that are used in modeling.

If the predicted activity of the new antibody is greater than the predicted value of the antibody before the change, the change is incorporated. Otherwise, the process reverts to the sequence of the antibody before the change. This process continues for a certain number of steps (preferably more than 10 steps, more preferably more than 100 steps, even more preferably more than 1000 steps) or until the predicted activity of the antibody converges to a value. Either the final antibody sequence in the series of iterations of the method, or the antibody sequence in the series with the highest predicted activity is selected. This process can optionally be performed more than once starting from each initial antibody sequence.

Method 9. As an optional addition to any of the design methods including methods 1, 2, 5, and 7, one or more substitutions determined to be detrimental to the desired property (e.g., by any of the criteria described in subsection 5.4.2 including criteria (xii)-(xv)) are eliminated.

Method 10. As an optional addition to any design method, newly designed variants that can be reached by making a certain number of substitutions to an antibody sequence whose activity has already been measured are discarded and not synthesized. In preferred embodiments newly designed variants that can be reached by making 10 or fewer substitutions to an antibody sequence whose activity has already been measured are not synthesized. More preferably, newly designed variants that can be reached by making 5 or fewer substitutions to an antibody sequence whose activity has already been measured are not synthesized. More preferably, newly designed variants that can be reached by making 3 or fewer substitutions to an antibody sequence whose activity has already been measured are not synthesized. Even more preferably, newly designed variants that can be reached by making 2 or fewer substitutions to an antibody sequence whose activity has already been measured are not synthesized. Most preferably, newly designed variants that can be reached by making 1 to an antibody sequence whose activity has already been measured are not synthesized.

One skilled in the art will appreciate that there are many possible ways of using sequence-activity information to design improved antibody variants. The schemes outlined above are intended to illustrate a few of the design possibilities.

5.4.4 Methods for Modifying the Choice and Combinations of Methods used to Determine Sequence-Activity Relationships The performances of different sequence-activity modeling methods can be quantitatively compared. Such comparisons can be used to modify variable parameters within each method, or to select methods of combining the results of two or more sequence-activity correlating methods as outlined in Subsection 5.3.1.

The outputs of methods that determine sequence-activity relationship are outlined in Section 5.3. These outputs can be combined to calculate the predicted activity of an antibody and the confidence with which that activity can be predicted. These predictions can be compared with activity values obtained experimentally for newly designed and synthesized antibody variants, and the method or methods of deriving sequence-activity relationships may be chosen or modified in one or more of the following ways.

1. The weights applied to the scores produced by the one or more sequence-activity correlating methods, for example as shown in Equation 4 or as described in Subsection 5.3.1 can be modified such that one or more of the following are true.
  (i) The activity value predicted for the most active newly designed and synthesized antibody variant most closely matches the experimentally determined activity for that variant.
  (ii) The rank order of activity values predicted for some number of the most active newly designed and synthesized antibody variants most closely match the experimentally determined rank order of activity for those variants. In preferred embodiments the rank order of activity values predicted for the 5 most active newly designed and synthesized antibody variants most closely matches the experimentally determined rank order of activity for those variants, more preferably the rank order of activity values predicted for the 10 most active newly designed and synthesized antibody variants most closely matches the experimentally determined rank order of activity for those variants, even more preferably the rank order of activity values predicted for the 15 most active newly designed and synthesized antibody variants most closely matches the experimentally determined rank order of activity for those variants.
  (iii) The fewest newly designed and synthesized antibody variants predicted to be more active than the initial target antibody possess experimentally determined activititiy that is lower than the initial target antibody.
  (iv) The fewest newly designed and synthesized antibody variants predicted to be more active than the most active previously tested antibody possess experimentally determined activities that are lower than the most active previously tested antibody.

2. The sequence-activity correlating method is chosen such that one or more of the following are true.
  (i) The activity value predicted for the most active newly designed and synthesized antibody variant most closely matches the experimentally determined activity for that variant.
  (ii) The rank order of activity values predicted for some number of the most active newly designed and synthesized antibody variants most closely match the experimentally determined rank order of activity for those variants. In preferred embodiments the rank order of activity values predicted for the 5 most active newly designed and synthesized antibody variants most closely matches the experimentally determined rank order of activity for those variants, more preferably the rank order of activity values predicted for the 10 most active newly designed and synthesized antibody variants most closely matches the experimentally determined rank order of activity for those variants, even more preferably the rank order of activity values predicted for the 15 most active newly designed and synthesized antibody variants most closely matches the experimentally determined rank order of activity for those variants.
  (iii) The fewest newly designed and synthesized antibody variants predicted to be more active than the initial target antibody possess experimentally determined activitities that are lower than the initial target antibody.
  (iv) The fewest newly designed and synthesized antibody variants predicted to be more active than the most active previously tested antibody possess experimentally determined activitities that are lower than the most active previously tested antibody.

3. In some embodiments, the process of steps 1 or 2 can be performed using regression techniques, machine learning or other multivariate data analysis tools to calculate or minimize the differences between the values predicted by the sequence-activity relationship, and those observed experimentally.

4. In some embodiments, the process of steps 1 or 2 can be performed using values predicted by the sequence-activity relationship, and those observed experimentally for more than one set of antibodies.

5. In some embodiments the process of step 4 can be performed using two or more datasets from antibodies that fall into the same class and subclass. For example, two or more sets of IgG antibodies, two or more sets of IgE antibodies, two or more sets of single chain antibodies, two or more sets of Fab fragments. Weights for expert system rules 120 that are modified using two or more datasets from antibodies of the same class and subclass can be stored, for example in knowledge base 108 or case-specific data 110. These weights or choices for sequence-activity determining methods can then be used by expert system 100 when a subsequent target antibody sequence and activity dataset of that class and subclass is presented.

6. In some embodiments the process of step 4 can be performed using two or more datasets from antibodies that fall into the same class. For example two or more sets of human antibodies, two or more sets of murine antibodies. Weights for expert system 100 rules 120 that are modified using two or more datasets from antibodies of the same class can be stored, for example in knowledge base 108 or case-specific data 110. These weights for expert system 100 rules 120 can then be used by expert system 100 when a subsequent target antibody sequence and activity dataset of that class and subclass is presented.

5.5 Use of Sequence-Activity Relationships to Train an Expert System for Substitution identification The endpoint of a process of antibody optimization is reached when one or more antibodies are obtained with one or more properties at the levels defined by a user, these activity levels being appropriate to allow the use of the antibody in performing a specific task. This corresponds to FIG. 2 step 08.

In addition to designing improved antibody variants, information from sequence-activity relationships can be used to provide information to improve the initial selection of substitutions, for example by modifying the weights applied to the scores produced by the expert system 100 as described in Section 5.1. As an example, the weights can be modified according to the following process.

1. As described in Section 5.3, the sequence-activity relationship can be used to calculate (i) a regression coefficient, weight or other value describing the relative or absolute contribution of each substitution or combination of substitutions to one or more activity of the antibody, (ii) a standard deviation, variance or other measure of the confidence with which the value describing the contribution of the substitution or combination of substitutions to one or more activity of the antibody can be assigned, and/or (iii) a rank order of preferred substitutions.

2. The results of applying two or more rules 120 of expert system 100 are combined and can be used to obtain (i) a score describing the predicted effect of a substitution upon one or more antibody property, (ii) a probability or confidence describing the predicted effect of a substitution upon one or more antibody property, activity or function, or (iii) a predicted rank order of preferred substitutions. Different values for each of these predictions can result from modifications of the weights applied to the scores produced by expert system 100 as described in Section 5.1, for example as shown in equations (1) or (2).

3. The weights applied to the scores produced by expert system 100 can be modified such that one or more of the following are true.
   (i) The regression coefficient, weight or other value describing the relative or absolute contribution of each substitution or combination of substitutions to one or more activity of the antibody that is derived from the sequence-activity relationship more closely corresponds with the score describing the predicted effect of a substitution upon one or more antibody property, activity or function that is derived from expert system 100.
   (ii) The standard deviation, variance or other measure of the confidence with which the value describing the contribution of the substitution or the combination of substitutions to one or more activity of the antibody can be assigned that is derived from the sequence-activity relationship more closely corresponds with the probability or confidence describing the predicted effect of a substitution upon one or more antibody property, activity or function that is derived from expert system 100.
   (iii) The rank order of preferred substitutions that is derived from the sequence-activity relationship more closely corresponds with the predicted rank order of preferred substitutions that is derived from expert system 100.

4. In some embodiments, the process of steps 1 to 3 can be performed using regression techniques, machine learning or other multivariate data analysis tools to minimize the differences between the values obtained from the sequence-activity relationship, and those predicted by expert system 100.

5. In some embodiments, the process of steps 1 to 3 can be performed using expert system 100 predictions and sequence-activity relationships for more than one set of antibodies.

6. In some embodiments the process of step 5 can be performed using two or more datasets from antibodies that fall into the same class and subclass. For example, two or more sets of, two or more sets of IgG antibodies, two or more sets of IgE antibodies, two or more sets of single chain antibodies, two or more sets of Fab fragments. Weights for expert system 100 rules 120 that are modified using two or more datasets from antibodies of the same class and subclass can be stored, for example in knowledge base 108 or case-specific data 110. These weights for expert system rules 120 can then be used by expert system 100 when a subsequent target antibody of that class and subclass is presented.

7. In some embodiments the process of step 5 can be performed using two or more datasets from antibodies that fall into the same class. For example, two or more sets of human antibodies, two or more sets of murine antibodies. Weights for expert system 100 rules 120 that are modified using two or more datasets from antibodies of the same class can be stored, for example in knowledge base 108 or case-specific data 110. These weights for rules 120 can then be used by expert system 100 when a subsequent target antibody of that class is presented.

By using a formal system for substitution selection, predictions made by expert system 100 can be improved so that preferences (e.g. higher weights) are given to selection methods 130 that have performed well in previous iterations.

Different algorithms and methods for identifying productive substitutions and for deriving sequence activity relationships may be better suited to different types of antibody, including different animal origins, different antibody fragments, optimization compared with humanization.

By using feedback loops of this nature, where quantitative scoring or ranking protocols are developed, a learning, automated computational system for antibody optimization can be developed. This system could include generic information applicable to all antibody classes and specific information applicable to a more limited subset of antibodies.

Such a computational system could be made available directly, via the internet and/or on a subscription basis.

5.6 Utility of the Variants of this Invention

Other useful products produced by the method of the invention include antibodies incorporating substitutions identified through construction and characterizing sets of variant antibodies. Where the antibody is encoded by a polynucleotide this also includes vectors (including expression vectors) comprising such polynucleotides, host cells comprising such polynucleotides and/or vectors, and libraries of antibodies, and libraries of host cells comprising and/or expressing such libraries of antibodies.

The antibodies developed using the methods of the invention can be used alone or in combination with other prophylactic or therapeutic agents for treating, managing, preventing or ameliorating a disorder or one or more symptoms thereof.

The present invention provides methods for preventing, managing, treating, or ameliorating a disorder comprising administering to a subject in need thereof one or more antibodies of the invention alone or in combination with one or more therapies (e.g., one or more prophylactic or therapeutic agents) other than an antibody of the invention. The present invention also provides compositions comprising one or more antibodies of the invention and one or more prophylactic or therapeutic agents other than antibodies of the invention and methods of preventing, managing, treating, or ameliorating a disorder or one or more symptoms thereof utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy that is known to be useful, or that has been used or is currently being used for the prevention, management, treatment, or amelioration of a disorder or one or more symptoms thereof can be used in combination with an antibody of the invention in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, Md. et al. (eds.), 17th Ed., Merck Sharp & Dohme Research Laboratories, Rahway, N.J., 1999; Cecil Textbook of Medicine, 20th Ed., Bennett and Plum (eds.), W. B. Saunders, Philadelphia, 1996 for information regarding therapies (e.g., prophylactic or therapeutic agents) that have been or are currently being used for preventing, treating, managing, or ameliorating a disorder or one or more symptoms thereof. Examples of such agents include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

The antibodies of the invention can be used directly against a particular antigen. In some embodiments, antibodies of the invention belong to a subclass or isotype that is capable of mediating the lysis of cells to which the antibody binds. In a specific embodiment, the antibodies of the invention belong to a subclass or isotype that, upon complexing with cell surface proteins, activates serum complement and/or mediates antibody dependent cellular cytotoxicity (ADCC) by activating effector cells such as natural killer cells or macrophages.

The biological activities of antibodies are known to be determined, to a large extent, by the constant domains or Fc region of the antibody molecule (Uananue and Benacerraf, Textbook of Immunology, 2nd Edition, Williams & Wilkins, p. 218 (1984)). This includes their ability to activate complement and to mediate antibody-dependent cellular cytotoxicity (ADCC) as effected by leukocytes. Antibodies of different classes and subclasses differ in this respect, as do antibodies from the same subclass but different species; according to the present invention, antibodies of those classes having the desired biological activity are prepared.

In general, mouse antibodies of the IgG2a and IgG3 subclass and occasionally IgG1 can mediate ADCC, and antibodies of the IgG3, IgG2a, and IgM subclasses bind and activate serum complement. Complement activation generally requires the binding of at least two IgG molecules in close proximity on the target cell. However, the binding of only one IgM molecule activates serum complement.

The ability of any particular antibody to mediate lysis of the target cell by complement activation and/or ADCC can be assayed. The cells of interest are grown and labeled in vitro; the antibody is added to the cell culture in combination with either serum complement or immune cells which may be activated by the antigen antibody complexes. Cytolysis of the target cells is detected by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

Use of IgM antibodies may be preferred for certain applications, however IgG molecules by being smaller may be more able than IgM molecules to localize to certain types of infected cells.

In some embodiments, the antibodies of this invention are useful in passively immunizing patients.

The antibodies of the invention can also be used in diagnostic assays either in vivo or in vitro for detection/identification of the expression of an antigen in a subject or a biological sample (e.g., cells or tissues). Non-limiting examples of using an antibody, a fragment thereof, or a composition comprising an antibody or a fragment thereof in a diagnostic assay are given in U.S. Pat. Nos. 6,392,020; 6,156,498; 6,136,526; 6,048,528; 6,015,555; 5,833,988; 5,811,310; 8 5,652,114; 5,604,126; 5,484,704; 5,346,687; 5,318,892; 5,273,743; 5,182,107; 5,122,447; 5,080,883; 5,057,313; 4,910,133; 4,816,402; 4,742,000; 4,724,213; 4,724,212; 4,624,846; 4,623,627; 4,618,486; 4,176,174 (all of which are incorporated herein by reference). Suitable diagnostic assays for the antigen and its antibodies depend on the particular antibody used. Non-limiting examples are an ELISA, sandwich assay, and steric inhibition assays. For in vivo diagnostic assays using the antibodies of the invention, the antibodies may be conjugated to a label that can be detected by imaging techniques, such as X-ray, computed tomography (CT), ultrasound, or magnetic resonance imaging (MRI). The antibodies of the invention can also be used for the affinity purification of the antigen from recombinant cell culture or natural sources.

5.7 Definitions

It is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Unless defined otherwise herein, all technical and scientific terms used herein have the same meaning as commonly understood by one of ordinary skill in the art to which this invention belongs. Singleton et al., *Dictionary Of Microbiology And Molecular Biology*, $2^{nd}$ ed., John Wiley and Sons, New York (1994), and Hale & Marham, *The Harper Collins Dictionary Of Biology*, Harper Perennial, N.Y. (1991) provide one of skill with a general dictionary of many of the terms used in this invention. Bioinformatic terms referring to expert systems are used in the same sense that they appear in Jackson, *Introduction To Expert Systems*, 3$^{rd}$ ed., Addison-Wesley, NY (1999). Although any methods and materials similar or equivalent to those described herein can be used in the practice or testing of the present invention, the preferred methods and materials are described. Unless otherwise indicated, nucleic acids are written left to right in 5' to 3' orientation; amino acid sequences are written left to right in amino to carboxy orientation, respectively. The headings provided herein are not limitations on the invention, but exemplify the various aspects of the invention. Accordingly, the terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides which can perform that function or which can be modified (e.g., reverse transcribed) to perform that function are used. Where the polynucleotides are to be used in a scheme which requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the NI and C6-NH2, respectively, of adenosine and between the C2-oxy, N3 and C4-NH2, of cytidine and the C2-NH2, N'-H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidi-ne) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other nonnatural base pairs may be synthesized by the method described in Piccirilli et al. (1990) Nature 343:33-37 for the synthesis of 2,6-diaminopyrimidine and its complement (1-methylpyrazolo-[4,3] pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands of base pairs.

The term "protein" refers to contiguous "amino acids" or amino acid "residues." Typically, proteins have a function. However, for purposes of this invention, proteins also encompasses polypeptides and smaller contiguous amino acid sequences that do not have a functional activity. "Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Sequence variants" refers to variants of discrete antibodies (that is antibodies whose sequence can be uniquely defined) including polynucleotide and polypeptide and variants. Sequence variants are sequences that are related to one another or to a common nucleic acid or amino acid "reference sequence" but contain some differences in nucleotide or amino acid sequence from each other. These changes can be transitions, transversions, conservative substitutions, non-conservative substitutions, deletions, insertions or substitutions with non-naturally occurring nucleotides or amino acids (mimetics). The phrase "optimizing a sequence" refers to the process of creating nucleic acid or protein variants so that the desired functionality and or properties of the protein or nucleic acid are improved. One of skill will realize that optimizing an antibody could involve selecting a variant with lower functionality than the parental protein if that is desired.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B:120-126); humanized antibody molecules (see, for example, Riechmann et al. (1988) Nature 332:323-327; Verhoeyan et al. (1988) Science 239:1534-1536; and U.K. Patent Publication No. GB 2,276,169, published Sep. 21, 1994); and, any functional fragments obtained from such molecules, wherein such fragments retain specific-binding properties of the parent antibody molecule.

As used herein, the terms "antibody" and "antibodies" further refer to monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab) fragments, disulfide-linked Fvs (sdFv), anti-idiotypic (anti-Id) antibodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

A typical antibody contains two heavy chains paired with two light chains. A full-length heavy chain is about 50 kD in size (approximately 446 amino acids in length), and is encoded by a heavy chain variable region gene (about 116 amino acids) and a constant region gene. There are different constant region genes encoding heavy chain constant region of different isotypes such as alpha, gamma (IgG1, IgG2, IgG3, IgG4), delta, epsilon, and mu sequences. A full-length light chain is about 25 Kd in size (approximately 214 amino acids in length), and is encoded by a light chain variable region gene (about 110 amino acids) and a kappa or lambda constant region gene. The variable regions of the light and/or heavy chain are responsible for binding to an antigen, and the constant regions are responsible for the effector functions typical of an antibody.

As used herein, the term "CDR" refers to the complement determining region within antibody variable sequences. There are three CDRs in each of the variable regions of the heavy chain and the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest, National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917, 1987, and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions can be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein can utilize CDRs defined according to any of these systems, although preferred embodiments use Kabat or Chothia defined CDRs.

As used herein, the term "epitopes" refers to fragments of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide (including, but not limited to an antibody) comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or protein. In a specific embodiment, a fragment of a protein or polypeptide retains at least one function of the protein or polypeptide.

As used herein, the term "immunospecifically binds to an antigen" and analogous terms refer to peptides, polypeptides, proteins (including, but not limited to fusion proteins and antibodies) or fragments thereof that specifically bind to an antigen or a fragment and do not specifically bind to other antigens. A peptide, polypeptide, or protein that immunospecifically binds to an antigen may bind to other antigens with lower affinity as determined by, e g., immunoassays, BIAcore, or other assays known in the art. Antibodies or fragments that immunospecifically bind to an antigen may be cross-reactive with related antigens. Preferably, antibodies or fragments that immunospecifically bind to an antigen do not cross-react with other antigens.

As used herein, the term "in combination" refers to the use of more than one therapies (e.g., more than one prophylactic agent and/or therapeutic agent). The use of the term "in combination" does not restrict the order in which therapies (e.g., prophylactic and/or therapeutic agents) are administered to a subject. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject.

As used herein, the term "pharmaceutically acceptable" refers approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing," and "prevention" refer to the inhibition of the development or onset of a disorder or the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the terms "prophylactic agent" and "prophylactic agents" refer to any agent(s) which can be used in the prevention of a disorder or one or more of the symptoms thereof In certain embodiments, the term "prophylactic agent" refers to an antibody of the invention. In certain other embodiments, the term "prophylactic agent" refers to an agent other than an antibody of the invention. Preferably, a prophylactic agent is an agent which is known to be useful to or has been or is currently being used to the prevent or impede the onset, development, progression and/or severity of a disorder or one or more symptoms thereof.

As used herein, the term "prophylactically effective amount" refers to the amount of a therapy (e.g., prophylactic agent) which is sufficient to result in the prevention of the development, recurrence, or onset of a disorder or one or more symptoms thereof, or to enhance or improve the prophylactic effect(s) of another therapy (e.g., a prophylactic agent).

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgous monkey, a chimpanzee, and a human), and most preferably a human. In one embodiment, the subject is a non-human animal such as a bird (e.g., a quail, chicken, or turkey), a farm animal (e.g., a cow, horse, pig, or sheep), a pet (e.g., a cat, dog, or guinea pig), or laboratory animal (e.g., an animal model for a disorder). In a preferred embodiment, the subject is a human (e.g., an infant, child, adult, or senior citizen).

As used herein, the terms "therapeutic agent" and "therapeutic agents" refer to any agent(s) which can be used in the prevention, treatment, management, or amelioration of a disorder or one or more symptoms thereof In certain embodiments, the term "therapeutic agent" refers to an antibody of the invention. In certain other embodiments, the term "therapeutic agent" refers an agent other than an antibody of the invention. Preferably, a therapeutic agent is an agent which is known to be useful for, or has been or is currently being used for the prevention, treatment, management, or amelioration of a disorder or one or more symptoms thereof.

As used herein, the term "therapeutically effective amount" refers to the amount of a therapy (e.g., an antibody of the invention), which is sufficient to reduce the severity of a disorder, reduce the duration of a disorder, ameliorate one or more symptoms of a disorder, prevent the advancement of a disorder, cause regression of a disorder, or enhance or improve the therapeutic effect(s) of another therapy.

As used herein, the terms "therapies" and "therapy" can refer to any protocol(s), method(s), and/or agent(s) that can be used in the prevention, treatment, management, and/or amelioration of a disorder or one or more symptoms thereof. In certain embodiments, the terms "therapy" and "therapy" refer to anti-viral therapy, anti-bacterial therapy, anti-fungal therapy, anti-cancer agent, biological therapy, supportive therapy, and/or other therapies useful in treatment, management, prevention, or amelioration of a disorder or one or more symptoms thereof known to one skilled in the art, for example, a medical professional such as a physician.

As used herein, the terms "treat," "treatment," and "treating" refer to the reduction or amelioration of the progression, severity, and/or duration of a disorder or amelioration of one or more symptoms thereof resulting from the administration of one or more therapies (including, but not limited to, the administration of one or more prophylactic or therapeutic agents).

The term "sequence alignment" refers to the result when at least two antibody sequences are compared for maximum correspondence, as measured using a sequence comparison algorithms. Optimal alignment of sequences for comparison can be conducted by any technique known or developed in the art, and the invention is not intended to be limited in the alignment technique used. Exemplary alignment methods include the local homology algorithm of Smith & Waterman, Adv. Appl. Math. 2:482 (1981), the homology alignment algorithm of Needleman & Wunsch, J. Mol. Biol. 48:443 (1970), the search for similarity method of Pearson & Lipman, Proc. Nat'l. Acad. Sci. USA 85:2444 (1988), by computerized implementations of these algorithms (e.g., GAP, BESTFIT, FASTA, and TFASTA in the Wisconsin Genetics Software Package, Genetics Computer Group, 575 Science Dr., Madison, Wis.), and by inspection.

The "three dimensional structure" of a protein is also termed the "tertiary structure" or the structure of the protein in three dimensional space. Typically the three dimensional structure of a protein is determined through X-ray crystallography and the coordinates of the atoms of the amino acids determined The coordinates are then converted through an algorithm into a visual representation of the protein in three dimensional space. From this model, the local "environment" of each residue can be determined and the "solvent accessibility" or exposure of a residue to the extraprotein space can be determined In addition, the "proximity of a residue to a site of functionality" or active site and more specifically, the "distance of the α or β carbons of the residue to the site of functionality" can be determined For glycine residues, which lack a β carbon, the a carbon can be substituted. Also from the three dimensional structure of a protein, the residues that "contact with residues of interest" can be determined. These would be residues that are close in three dimensional space and would be expected to form bonds or interactions with the residues of interest. And because of the electron interactions across bonds, residues that contact residues in contact with residues of interest can be investigated for possible mutability. Additionally, nuclear magnetic resonance spectroscopy can be used to determine the structure. Additionally, molecular modeling can be used to determine the structure, and can be based on an homologous structure or ab initio. Energy minimization techniques can also be employed.

Although not dependent on three dimensional space, the "residue chemistry" of each amino acid is influenced by its position in a protein. "Residue chemistry" refers to characteristics that a residue possesses in the context of a protein or by itself. These characteristics include, but are not limited to, polarity, hydrophobicity, net charge, molecular weight, propensity to form a particular secondary structure, and space filling size.

As used herein, the term "carrier" refers to a diluent, adjuvant, excipient, or vehicle. Carriers can be liquids, such as water and oils, including those of petroleum, animal, vegetable or synthetic origin, such as peanut oil, soybean oil, mineral oil, sesame oil and the like. The vehicles (e.g., pharmaceutical vehicles) can be saline, gum acacia, gelatin, starch paste, talc, keratin, colloidal silica, urea, and the like. In addition, auxiliary, stabilizing, thickening, lubricating and coloring agents can be used. When administered to a patient, the carriers are preferably sterile. Water can be the carrier when composition is administered intravenously. Saline solutions and aqueous dextrose and glycerol solutions can also be employed as liquid vehicles, particularly for injectable solutions. Suitable vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. Compositions, if desired, can also contain minor amounts of wetting or emulsifying agents, or pH buffering agents.

As used herein the term "functional domain" means a segment of a protein that has one or more of the following properties (i) a structurally independent section of a protein, (ii) a section of a protein that is homologous to a section of another protein, (iii) a segment of protein involved in one or more specific functions, (iv) an independently evolving unit in a protein, (v) a segment of protein containing a particular sequence motif, (vi) a section of the protein containing an active site, a binding site or a regulatory site. See, for example, Suhail A Islam, Jingchu Luo and Michael J E Sternberg, 1995, "Identification and analysis of domains in proteins," Protein Engineering 8, 513-525; Orengo et al., 1997, "CATH-A Hierarchic Classification of Protein Domain Structures," Structure 5, 1093-1108; and Pearl et al., 2000, "Assigning genomic sequences to CATH," Nucleic Acids Research 28, 277-282, which are each hereby incorporated by reference in their entirety.

An expert system 100 is computer program that represents and reasons with the knowledge of some specialist subject (antibodies) with a view to solving problems or giving advice (via rank ordering of substitutions with reasoning)

Knowledge acquisition is the transfer and transformation of potential problem-solving expertise (e.g. knowledge of analysing nucleotide or protein structure, nucleotide or protein phylogeny) from the knowledge source to a program.

Knowledge base 108 is the encoded knowledge for an expert system 100. In a rule-based expert system 100, a knowledge base 108 typically incorporates definitions of attributes and rules along with control information.

An inference engine 106 is software that provides the reasoning mechanism in expert system 100. In a rule based expert system 100, it typically implements forward chaining and backward chaining strategies.

A substitution in an antibody is the replacement of one monomer with a different monomer.

A virtual surrogate screen is a measure of the activity of an antibody in dimensions that are mathematically constructed from physical measurements of antibody properties in two or more assays.

The terms screen, assay, test and measurement are used interchangeably to mean a method of determining one or more property of an antibody.

A high throughput screen, assay, test or measurement is used to describe any method for determining one or more property of a plurality of antibodies either sequentially or simultaneously. The actual number of antibody variants whose properties can be determined by a test that is considered a high throughput screen varies from as few as 84 samples per day (Decker et al. (2003) Appl Biochem Biotechnol 105: 689-703.) to many millions. For the purposes of this invention we define a high throughput screen as an assay that can measure one or more antibody property for 400 antibody variants in 1 week, preferably a test that can measure one or more antibody property for 1,000 antibody variants in 1 week, more preferably a test that can measure one or more antibody properties for 10,000 antibody variants in one week.

5.8 Synthesis of Antibody Sequence Variants

Antibody variants can be synthesized by methods for constructing or obtaining specific nucleic acid or polypeptide sequences described in the art. Antibody variants are designed, for example, in step 03 of FIG. 2, as described in Section 5.2, above.

Oligonucleotides and polyucleotides can be synthesized using a variety of chemistries including phosphoramidite chemistry; optionally this synthesis may be performed using a commercially available DNA synthesizer. Oligonucleotides and polynucleotides may also be purchased from a commercial supplier of synthetic DNA.

Chemically synthesized oligonucleotides can be incorporated into larger polynucleotides to create one or more of the designed sequence variants using site-directed mutagenesis. Suitable site-directed techniques include those in which a template strand is used to prime the synthesis of a complementary strand lacking a modification in the parent strand, such as methylation or incorporation of uracil residues; introduction of the resulting hybrid molecules into a suitable host strain results in degradation of the template strand and replication of the desired mutated strand. See (Kunkel (1985) Proc Natl Acad Sci USA 82: 488-92.); QuikChange™ kits available from Stratagene, Inc., La Jolla, Calif. PCR methods for introducing site-directed changes can also be employed. Site-directed mutagenesis using a single stranded DNA template and mutagenic oligos is well known in the art (Ling & Robinson 1997, Anal Biochem 254:157 1997). It has also been shown that several oligos can be incorporated at the same time using these methods (Zoller 1992, Curr Opin Biotechnol 3: 348). Single stranded DNA templates are synthesized by degrading double stranded DNA (Strandase™ by Novagen). The resulting product after strain digestion can be heated and then directly used for sequencing. Alternatively, the template can be constructed as a phagemid or M13 vector. Other techniques of incorporating mutations into DNA are known and can be found in, e.g., Deng et al. 1992, Anal Biochem 200:81.

Multiple chemically synthesized oligonucleotides can together be assembled into larger polynucleotides to create one or more of the designed sequence variants. Oligonucleotides can be assembled into larger single- or double-stranded polynucleotides in vivo or in vitro by a variety of methods including but not limited to annealing, restriction enzyme digestion and ligation, particularly using restriction enzymes whose cleavage site is distinct from their recognition sites (see for example Pierce 1994, Biotechniques 16:708-15; Mandecki & Bolling 1988, Gene 68:101-7), ligation (see for example Edge at al 1981, Nature 292:756-62; Jayaraman & Puccini 1992 Biotechniques 12:392-8), ligation followed by polymerase chain reaction amplification (see for example Jayaraman et al 1991, Proc Natl Acad Sci USA. 88:4084-8), overlap extension using thermostable nucleotide polymerases and/or ligases (see for example Ye et al. 1992, Biochem Biophys Res Commun 186:143-9; Horton et al 1989 Gene. 77:61-8; Stemmer et al 1995 Gene. 164:49-53), dual asymmetric PCR (see for example Sandhu et al 1992, Biotechniques 12:14-6) stepwise elongation of sequences (see for example Majumder 1992, Gene. 110:89-94), the ligase chain reaction (see for example Au et al 1998, Biochem Biophys Res Commun. 248:200-3; Chalmers & Curnow 2001, Biotechniques 30:249-52), insertional mutagenesis (see for example Ciccarelli et al 1990 Nucleic Acids Res. 18:1243-8), the exchangeable template reaction (see Khudyakov et al 1993, Nucleic Acids Res. 21:2747-54), sequential ligation of one or more oligonucleotides to an anchored oligonucleotide (for example a biotinylated oligonucleotide immobilized on streptavidin resin), cotransformation into an appropriate host cell such as mammalian, yeast or bacterial cells capable of joining polynucleotides (see for example Raymond et al 1999, BioTechniques 26: 134-141), or any combination of steps involving the activity of one or more of a polymerase, a ligase, a restriction enzyme, and a recombinase. Oligonucleotides can optionally be designed to improve their assembly into larger polynucleotides and subsequent processing, for example by optimizing annealing properties and eliminating restriction sites (see for example Hoover & Lubkowski 2002, Nucleic Acids Res. 30:e43).

Synthesis of polynucleotide sequence variants can also be multiplexed. Individual variants can subsequently be identified, for example by picking and sequencing single clones. Other methods of deconvolution include testing for an easily measured phenotype (examples include but are not limited to colorigenic, fluorigenic or turbidity-altering reactions that can be visualized on agar plates), then grouping clones according to activity and selecting one or more clone from each group. Optionally the one or more clone from each group may be sequenced.

One example of multiplexed variant synthesis is to incorporate one or more oligonucleotides containing one or more alternative nucleotide substitutions into one or more polynucleotide reference sequences simultaneously. Oligonucleotides synthesized from mixtures of nucleotides can be used. The synthesis of oligonucleotide libraries is well known in the art. In one alternative, degenerate oligos from trinucleotides can be used (Gaytan, et al., 1998, Chem Biol 5:519; Lyttle, et al 1995, Biotechniques 19:274; Virnekas, et al 1994, Nucl. Acids Res 22:5600; Sondek & Shortle 1992, Proc. Natl. Acad. Sci. USA 89:3581). In another alternative, degenerate oligos can be synthesized by resin splitting (Lahr, et al 1999, Proc. Natl Acad. Sci. USA 96:14860; Chatellier, et al., 1995, Anal. Biochem. 229:282; and Haaparanta & Huse 1995, Mol Divers 1:39). Mixtures of individual primers for the substitutions to be introduced by site directed mutagenesis can be simultaneously employed in a single reaction to produce the desired combinations of mutations. Simultaneous mutation of adjacent residues can be accomplished by preparing a plurality of oligonucleotides representing the desired combinations. In an alternative embodiment, sequences are assembled using PCR to link synthetic oligos (Horton, et al 1989, Gene 77:61; Shi, et al 1993, PCR Methods Appl. 3:46; and Cao 1990, Technique 2:109). PCR with a mixture of mutagenic oligos can be used to create a multiplexed set of sequence variants that can subsequently be deconvoluted.

Cassette mutagenesis can also be used in creating multiple polynucleotide sequence variants. Using this technique, a set of sequences can be generated by ligating fragments obtained by oligonucleotide synthesis, PCR or combinations thereof. Segments for ligation can, for example, be generated by PCR and subsequent digestion with type II restriction enzymes. This enables introduction of mutations via the PCR primers. Furthermore, type II restriction enzymes generate non-palindromic cohesive ends which significantly reduce the likelihood of ligating fragments in the wrong order. Techniques for ligating many fragments can be found in Berger, et al., Anal Biochem 214:571 (1993).

Antibody variants can be synthesized as nucleic acid sequence variants according to any of the processes described here, followed by expression either in vivo or in an in vitro cell-free system. They may also be made directly using commercial peptide synthesizers. Antibody variants may additionally be synthesized by chemically ligating one or more synthetic peptides to one or more polypeptide segments created by expression of a polynucleotide (see for example Pal et al 2003 Protein Expr Purif. 29:185-92).

Antibody variants may optionally include non-natural amino acids, incorporated at specific positions in the protein sequence by a variety of methods (see for example Hyun Bae et al 2003, J Mol Biol. 328:1071-81; Hohsaka & Sisido 2002, Curr Opin Chem Biol. 6:809-15; Li and Roberts 2003, Chem. Biol 10:233-9).

The particular chemical and/or molecular biological methods used to construct the antibody sequence variants are not critical; any method(s) that provide the desired sequence variants can be used.

5.9 Representative Tests for Antibody Function

Section 5.2 described how a designed set of antibody variants was designed. This set of antibodies is then synthesized using, for example, the techniques described in Section 5.8. Then the antibodies are tested for relevant biological activity and/or antibody properties. Determination of what constitutes a relevant antibody property is a case specific exercise. Non-limiting examples of antibody properties that can be relevant in some embodiments of the present invention include, but are not limited to antigenicity, immunogenicity, immunomodulatory activity, expression of the antibody in a homologous host, expression of the antibody in a heterologous host, expression of the antibody in a plant cell, susceptibility of the antibody to in vitro post-translational modifications and susceptibility of the antibody to in vivo post-translational modifications.

Of particular relevance for this invention are antibody properties whose measurements are intensive in their use of such resources as time, space, equipment and experimental animals. Such characterizations can be rate limiting for empirical-based protein engineering approaches such as those methods applying directed evolution or screening libraries produced by other methods. A common solution to this limitation is to develop a high-throughput screen. See, for example, Olsen et al. (2000) Curr Opin Biotechnol 11:331-7.

High throughput screens typically do not measure the complex combination of functions that are desired in the final engineered antibody. High throughput screens can be used to measure some properties of the antibody, and the method of this invention allows the properties measured in two or more of these high throughput screens to be combined and used to create a virtual surrogate screen for the properties of interest. High throughput screens that may be used to measure potentially relevant antibody properties include but are not limited to: flow cytometry (Daugherty et al. (2000) J Immunol Methods 243: 211-27; Georgiou (2000) Adv Protein Chem 55: 293-315; Olsen et al. (2000) Curr Opin Biotechnol 11: 331-7.) solid phase digital imaging (Joo et al. (1999) Chem Biol 6: 699-706; Joern et al. (2001) J Biomol Screen 6: 219-23.), computational and cellular immunogenicity assays (Tangri et al. (2002) Curr Med Chem 9: 2191-9.), fluorescence anisotropy (Turconi et al. (2001) J Biomol Screen 6: 275-90.), flow cytometry, scintillation proximity (Jenh et al. (1998) Anal Biochem 256: 47-55; Skorey et al. (2001) Anal Biochem 291: 269-78.) or magnetic bead capture (Yeung et al. (2002) Biotechnol Prog 18: 212-20.) for measurement of surface density or binding affinity or avidity, cell surface display (Kim et al. (2000) Appl Environ Microbiol 66: 788-93.) [Little], fluorescence polarization assays for measuring protein phosphorylation or other cellular components (Parker et al. (2000) J Biomol Screen 5: 77-88; Allen et al. (2002) J Biomol Screen 7: 35-44; Kristjansdottir et al. (2003) Anal Biochem 316: 41-9.), assays that link cellular survival or growth to protein activity (Luthi et al. (2003) Biochim Biophys Acta 1620: 167-78.), assays that couple a reaction to a colorimetric or fluorimetric assay including two-hybrid or three-hybrid systems (Young et al. (1998) Nat Biotechnol 16: 946-50; Baker et al. (2002) Proc Natl Acad Sci USA 99: 16537-42.), a, electrospray and matrix adsorption laser desorption mass spectrometry (LC-MS and MALDI) for detection of small molecules and antibodies (Jankowski et al. (2001) Anal Biochem 290: 324-9; Raillard et al. (2001) Chem Biol 8: 891-8.), high performance liquid chromatography (HPLC), enzyme-linked immunosorbent assays (Fahey et al. (2001) Anal Biochem 290: 272-6; Mallon et al. (2001) Anal Biochem 294: 48-54.), detection of markers for cellular differentiation (Sottile et al. (2001) Anal Biochem 293: 124-8.), induction of a reporter gene in vivo or in vitro (Thompson et al. (2000) Toxicol Sci 57: 43-53.), small molecule or protein binding competition assays (Warrior et al. (1999) J Biomol Screen 4: 129-135; McMahon et al. (2000) J Biomol Screen 5: 169-76.) and time resolved fluorescence (Zhang et al. (2000) Anal Biochem 281: 182-6.).

Measurements of cell lines and primary cell cultures for cell-surface receptor surface density, measurements of cell surface receptor internalization rates, cell surface receptor post-translational modifications including phosphorylation, binding of antigens including but not limited to cellular growth factor receptors, receptors or mediators of tumor-driven angiogenesis, B cell surface antigens and proteins synthesized by or in response to pathogens, antigens produced by the induction of antibody-mediated cell killing, antigens produced by antibody-dependent macrophage activity, histamine, and antigens produced by induction of or cross-reaction with anti-idiotype antibodies.

Examples of antibody properties or activities whose measurement may be resource, time or cost-limited and that therefore cannot be accurately measured in high throughput are tests for the immunogenicity of an antibody, in vivo or cell-culture based viral titer measurements, any experiment in which an experimental animal or human being is used as a part of the measurement of one or more properties of the antibody, the level of expression of the antibody in a host, any experiment in which the antibody is produced within a plant particularly when the plant must be transformed with a polynucleotide encoding the antibody and the antibody be expressed within the plant, susceptibility of the antibody to be modified inside a living cell, susceptibility of the antibody to be modified not inside a living cell, measurement of the composition of a complex mixture of compounds whose composition has been altered by the action of the antibody (for example metabolomics or metabonomics, alteration of the properties of a cell for example alteration of the growth, replication or differentiation patterns of a cell or population of cells, therapeutic efficacy of an antibody and modulation of a signaling pathway.

Antibodies of the present invention or fragments thereof can be assayed in a variety of ways well-known to one of skill in the art. In particular, antibodies of the invention or fragments thereof can be assayed for the ability to immunospecifically bind to an antigen. Such an assay can be performed in solution (e.g., Houghten, 1992, Bio/Techniques 13:412 421), on beads (Lam, 1991, Nature 354:82 84), on chips (Fodor, 1993, Nature 364:555 556), in bacteria (U.S. Pat. No. 5,223,409), in spores (U.S. Pat. Nos. 5,571,698; 5,403,484; and 5,223,409), in plasmids (Cull et al., 1992, Proc. Natl. Acad. Sci. USA 89:1865 1869) or in phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

The antibodies of the invention or fragments thereof can be assayed for immunospecific binding to a specific antigen and cross-reactivity with other antigens by any method known in the art Immunoassays that can be used to analyze immunospecific binding and cross-reactivity include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well-known in the art (see, e.g., Ausubel et al., eds., 1994, Current Protocols in Molecular Biology, Vol. 1, John Wiley & Sons, Inc., New York, which is incorporated by reference herein in its entirety).

Antibodies of the invention or fragments thereof can also be assayed for their ability to inhibit the binding of an antigen to its host cell receptor using techniques known to those of skill in the art. For example, cells expressing a receptor can be contacted with a ligand for that receptor in the presence or absence of an antibody or fragment thereof that is an antagonist of the ligand and the ability of the antibody or fragment thereof to inhibit the ligand's binding can measured by, for example, flow cytometry or a scintillation assay. The ligand or the antibody or antibody fragment can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the ligand and its receptor. Alternatively, the ability of antibodies or fragments thereof to inhibit a ligand from binding to its receptor can be determined in cell-free assays. For example, a ligand can be contacted with an antibody or fragment thereof that is an antagonist of the ligand and the ability of the antibody or antibody fragment to inhibit the ligand from binding to its receptor can be determined Preferably, the antibody or the antibody fragment that is an antagonist of the ligand is immobilized on a solid support and the ligand is labeled with a detectable compound. Alternatively, the ligand is immobilized on a solid support and the antibody or fragment thereof is labeled with a detectable compound. A ligand can be partially or completely purified (e.g., partially or completely free of other polypeptides) or part of a cell lysate. Alternatively, a ligand can be biotinylated using techniques well known to those of skill in the art (e.g., biotinylation kit, Pierce Chemicals; Rockford, Ill.).

An antibody or a fragment thereof constructed and/or identified in accordance with the present invention can be tested in vitro and/or in vivo for its ability to modulate the biological activity of cells. Such ability can be assessed by, e.g., detecting the expression of antigens and genes; detecting the proliferation of cells; detecting the activation of signaling molecules (e.g., signal transduction factors and kinases); detecting the effector function of cells; or detecting the differentiation of cells. Techniques known to those of skill in the art can be used for measuring these activities. For example, cellular proliferation can be assayed by $^3H$-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and FACS analysis. The activation of signaling molecules can be assayed, for example, by kinase assays and electrophoretic shift assays (EMSAs).

The antibodies, fragments thereof, or compositions of the invention are preferably tested in vitro and then in vivo for the desired therapeutic or prophylactic activity prior to use in humans. For example, assays which can be used to determine whether administration of a specific pharmaceutical composition is indicated include cell culture assays in which a patient tissue sample is grown in culture and exposed to, or otherwise contacted with, a pharmaceutical composition, and the effect of such composition upon the tissue sample is observed. The tissue sample can be obtained by biopsy from the patient. This test allows the identification of the therapeutically most effective therapy (e.g., prophylactic or therapeutic agent) for each individual patient. In various specific embodiments, in vitro assays can be carried out with representative cells of cell types involved a particular disorder to determine if a pharmaceutical composition of the invention has a desired effect upon such cell types. For example, in vitro assay can be carried out with cell lines.

In yet other forms of antibody assays, the effect of an antibody, a fragment thereof, or a composition of the invention on peripheral blood lymphocyte counts can be monitored/assessed using standard techniques known to one of skill in the art. Peripheral blood lymphocytes counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in subject can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen which is conjugated to FITC or phycoerythrin, and measuring the number of T-cells by FACS.

The antibodies, fragments, or compositions of the invention used to treat, manage, prevent, or ameliorate a viral infection or one or more symptoms thereof can be tested for their ability to inhibit viral replication or reduce viral load in in vitro assays. For example, viral replication can be assayed by a plaque assay such as described, e.g., by Johnson et al., 1997, Journal of Infectious Diseases 176:1215-1224 176: 1215-1224. The antibodies or fragments thereof administered according to the methods of the invention can also be assayed for their ability to inhibit or downregulate the expression of viral polypeptides. Techniques known to those of skill in the art, including, but not limited to, western blot analysis, northern blot analysis, and RT-PCR can be used to measure the expression of viral polypeptides.

Antibodies, fragments, or compositions of the invention can be tested in additional in vitro assays that are well-known in the art. Such additional In vitro assays known in the art can also be used to test the existence or development of resistance of bacteria to a therapy. Such in vitro assays are described in Gales et al., 2002, Diag. Nicrobiol. Infect. Dis. 44(3):301-311; Hicks et al., 2002, Clin. Microbiol. Infect. 8(11): 753-757; and Nicholson et al., 2002, Diagn. Microbiol. Infect. Dis. 44(1): 101-107.

The antibodies, fragments, or compositions of the invention can be assayed for the ability to treat, manage, prevent, or ameliorate a fungal infection or one or more symptoms thereof. Any of the standard anti-fungal assays well-known in the art can be used to assess such acitivty. For instance, tests recommended by the National Committee for Clinical Laboratories (NCCLS) (See National Committee for Clinical Laboratories Standards. 1995, Proposed Standard M27T. Villanova, Pa., all of which is incorporated herein by reference in its entirety) and other methods known to those skilled in the art (Pfaller et al., 1993, Infectious Dis. Clin. N. Am. 7: 435-

444) can be used. Such antifungal properties can also be determined from a fungal lysis assay, as well as by other methods, including, inter alia, growth inhibition assays, fluorescence-based fungal viability assays, flow cytometry analyses, and other standard assays known to those skilled in the art.

Further, any in vitro assays known to those skilled in the art can be used to evaluate the prophylactic and/or therapeutic utility of an antibody disclosed herein for a particular disorder or one or more symptoms thereof.

The antibodies, compositions, or combination therapies of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; such aspects include, but are not limited to, the temporal regime of administering the therapies (e.g., prophylactic and/or therapeutic agents) whether such therapies are administered separately or as an admixture, and the frequency of administration of the therapies.

Animal models can be used to assess the efficacy of the antibodies, fragments thereof, or compositions of the invention for treating, managing, preventing, or ameliorating a particular disorder or one or more symptom thereof.

The antibodies, fragments thereof of compositions of the present invention can be assayed for their ability to decrease the time course of a particular disorder by at least 25%, preferably at least 50%, at least 60%, at least 75%, at least 85%, at least 95%, or at least 99%. The antibodies, compositions, or combination therapies of the invention can also be assayed for their ability to increase the survival period of organisms (e.g., humans) suffering from a particular disorder by at least 25%, preferably at least 50%, at least 60%, at least 75%, at least 85%, at least 95%, or at least 99%. Further, antibodies, fragments thereof, compositions, or combination therapies of the invention can be assayed their ability reduce the hospitalization period of humans suffering from viral respiratory infection by at least 60%, preferably at least 75%, at least 85%, at least 95%, or at least 99%.

The toxicity and/or efficacy of the antibodies, fragments thereof, or compositions of the present invention can be assayed by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Antibodies that exhibit large therapeutic indices are preferred. While antibodies that exhibit toxic side effects can be used, care should be taken to design a delivery system that targets such agents to the site of affected tissue in order to minimize potential damage to uninfected cells and, thereby, reduce side effects.

Technological advances in the future may make it possible to measure in higher throughput properties that can currently be measured only in low throughput. One skilled in the art will readily see that the methods of this invention may be used to correlate any antibody properties that are not easily measured with a high-throughput assay with other properties that are readily measured in high throughput.

5.10 Kits

The invention provides kits comprising a set of variant or a single variant in a set of variants that have been refined by the apparatus and methods describe herein.

The invention also provides a pharmaceutical pack or kit comprising one or more containers filled with a variant of set of variants of the present invention. The pharmaceutical pack or kit may further comprise one or more other prophylactic or therapeutic agents useful for the treatment of a particular disease. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.11 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material.

In a specific embodiment, an article of manufacture comprises packaging material and a pharmaceutical agent and instructions contained within said packaging material, wherein said pharmaceutical agent is a humanized antibody and a pharmaceutically acceptable carrier, and said instructions indicate a dosing regimen for preventing, treating or managing a subject with a particular disease. In another embodiment, an article of manufacture comprises packaging material and a pharmaceutical agent and instructions contained within said packaging material, wherein said pharmaceutical agent is a humanized antibody, a prophylactic or therapeutic agent other than the humanized antibody and a pharmaceutically acceptable carrier, and said instructions indicate a dosing regimen for preventing, treating or managing a subject with a particular disease. In another embodiment, an article of manufacture comprises packaging material and two pharmaceutical agents and instructions contained within said packaging material, wherein said first pharmaceutical agent is a humanized antibody and a pharmaceutically acceptable carrier and said second pharmaceutical agent is a prophylactic or therapeutic agent other than the humanized antibody, and said instructions indicate a dosing regimen for preventing, treating or managing a subject with a particular disease.

The present invention provides that the adverse effects that may be reduced or avoided by the methods of the invention are indicated in informational material enclosed in an article of manufacture for use in preventing, treating or ameliorating one or more symptoms associated with a disease. Adverse effects that may be reduced or avoided by the methods of the invention include but are not limited to vital sign abnormalities (e.g., fever, tachycardia, bardycardia, hypertension, hypotension), hematological events (e.g., anemia, lymphopenia, leukopenia, thrombocytopenia), headache, chills, dizziness, nausea, asthenia, back pain, chest pain (e.g., chest pressure), diarrhea, myalgia, pain, pruritus, psoriasis, rhinitis, sweating, injection site reaction, and vasodilatation. Since some of the therapies may be immunosuppressive, prolonged immunosuppression may increase the risk of infection, including opportunistic infections. Prolonged and sustained immunosuppression may also result in an increased risk of developing certain types of cancer.

Further, the information material enclosed in an article of manufacture can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

6. EXAMPLES

6.1 Engineering a Protein (Proteinase K) Using Expert Substitution Selection Methods and Sequence-Activity Relationships The design, synthesis and analysis of sequence variants of proteinase K is described here as an example of the use of sequence-activity relationships to engineer desired properties into a protein. Also described is the analysis of these variants using six different functional tests, and methods for determining components of a virtual screen.

FIG. 6 shows the amino acid sequence of proteinase K that occurs naturally in the fungus *Tritirachium album* Limber (Gunkel et al. (1989) Eur J Biochem 179: 185-194) (SEQ ID NO.: 2) together with an *E. coli* leader peptide (SEQ ID NO.: 1). FIG. 7 shows a nucleotide sequence designed to encode proteinase K (SEQ ID NO.: 3). The sequence has been modified from the original *Tritirachium album* sequence by removing an intron, adding an *E. coli* leader peptide and altering the codons used to resemble the distribution found in the highly expressed genes of *E coli*. The gene was synthesized for the natural proteinase K from oligonucleotides.

Several different criteria were used to identify positions and substitutions to make in the proteinase K sequence as detailed below 6.1.1 Principal Component Analysis to Identify Substitutions that may Contribute to Thermostability The proteinase K gene was used as probe against GenBank using BLAST based algorithms A BLAST score was chosen as a cut-off that identified more than ten but less than one hundred related sequences. This search identified the 49 sequences identified in FIG. 8.

The sequences (49 rows×728 variables) were represented in a Free-Wilson method of qualitative binary description of monomers (Kubinyi, 3D QSAR in drug design theory methods and applications. Pergamon Press, Oxford, 1990, pp 589-638), and distributed in a maximally compressed space using principal component analysis so that the first principal component (PC) captured 10.8 percent of all variance information (eigenvalue of 79), the second principal component (PC) captured 7.8 percent of all variance information (eigenvalue of 57), the third principal component (PC) captured 6.9 percent of all variance information (eigenvalue of 50), the fourth principal component (PC) captured 6.2 percent of all variance information (eigenvalue of 45), the fifth principal component (PC) captured 5.4 percent of all variance information (eigenvalue of 39) and so on until $728^{th}$ principal component (PC) captured 0 percent of all variance information (Eigenvalue 0).

All sequences were plotted in the first six principal components, which captured a total of 42 percent of all variance information present in the 728 dimensions. Sequences 46, 47, 48, 49 are all derived from thermophilic organisms and are all well separated from the proteinase K homologs 1-45 in both of the first two principal components, as shown in FIG. 9.

A corresponding plot of all loads describes the influence of each variable on the sample distribution in the various PC's. The correlation between loads (influence of variables—in this case amino acid residues) and score (distribution of samples—here proteinase K homologs) illustrates graphically which residues are unique in determining the phylogenetic separation of genes 46-49 from genes 1-45. This is shown in FIG. 10.

Subsequently, the lower left corner of the bottom left quadrant of the loads plot was magnified and the variables labeled (FIG. 11). By adding the PC1 and PC2 value for each variable one can rank order the influence of each residue for their reciprocal effect on sample distribution. This distribution of residue effects can be due to common ancestral history or can be due to functional constraints among this group of samples.

As can be seen in FIG. 11, residues that are completely co-evolving (due to sampling effects, phylogenetic ancestry or other) will have the exact same load and consequently collapse the variable space in as many dimensions as there are absolute coevolving residues. This is illustrated in the graph where residues 15D, 18D, 19Q, 22L, 23P, 65Y, 66D, 110R, 137P, 164D, 189C, 198R all are completely co-evolving and all have profound effect on the distribution of samples 46-49 in PC1 and PC2. After removing residues that are unique for only one of the extreme samples, residues that are common to the thermophiles but unique to one individual were retained and further explored. Variables here can be amino acids as depicted in this example, or any type of feature. Features include, but are not limited to, physico-chemical properties of one or more amino acid residues. The residues can be a block or modulated within the gene, or it can be a combination of residues not genetically linked such as in the example above of residues 15D, 18D, 19Q, 22L, 23P, 65Y, 66D, 110R, 137P, 164D, 189C, 198R.

The loads for the amino acids most responsible for the clustering of thermophilic proteinase K homologs are shown in FIG. 12. This information was then incorporated into knowledge base 108. This is an example of pre-processing information.

6.1.2 Structural Information for Homologous Enzymes

The BLAST search of Genbank for proteinase K homologs also revealed that proteinase K is homologous to subtilisin and other serine proteases. Subtilisin in particular has been extensively studied. The structures of naturally occurring and variant subtilsins have been obtained, and there is a large body of data regarding the functional effects of a substantial number of mutations. See, for example, Bryan, 2000, Biochim Biophys Acta 1543:203-222. Sequence and structural alignments of proteinase K with subtilisin allowed for the identification of homologous positions in proteinase K having changes known to improve activity or thermostabilize subtilisin. This information was incorporated into the knowledge base 108. This is an example of pre-processing information.

6.1.3 Sequence Information from Thermostable Close Homologs

Amongst the closest ten homologs of proteinase K identified by BLAST search of Genbank, are enzymes known to be thermostable. These enzymes were aligned positions that were conserved between the thermostable homologs but not found in non-thermostable homologs were identified. This information was then incorporated into the knowledge base 108. This is an example of pre-processing information.

6.1.4 Sequence Information from Close Homologs

One of the homologs identified in the BLAST search was highly related to proteinase K (>95% sequence identity) and also thermostable. The sequence of this protein was aligned with proteinase K and all amino acid changes between the two enzymes were identified. This information was then incorporated into the knowledge base 108. This is an example of pre-processing information.

6.1.5 Information Processing

Using the information described above that was placed in knowledge base 108, the following rules 120 were defined.

(a) Changes that are already present in proteinase K were eliminated.

(b) Changes that occur in the pro-region of the protein were eliminated (c) A score proportional to the load from the PCA analysis was added.

(d) A score for conservative changes was added.

(e) A score for changes found in a close homolog (>95% identical) was added.

(f) A score for change found in a close homolog that is thermostable but not in close homologs that are not thermostable was added.

An initial sequence space of 24 residues was defined using rules (a) through (f). Changes with the top 24 scores were picked. These residues are shown in FIG. 13.

These variations and all combinations of these variations encompass a sequence space of over a million different sequences. To reduce the number of variants to test in the first set of variants a design based on prior knowledge and single site statistics considerations was used (FIG. 2, step 03).

Based on information about the plasticity of serine proteases and subtilisin genes, variants with six changes per clone were designed. In this example all of the 24 top-scoring changes were equally represented. In other embodiments, a set of variants that represent each change with a frequency reflecting its actual score could have been designed. In this case, 24 clones were designed that cover the sequence space uniformly. One way to measure the uniformity of the space covered is by counting the number of instances a particular substitution (e.g., N95C) is seen in the 24 clones. This number was set at six for all the variations identified. This means, that in the set of variations synthesized, each of the identified mutations occurs six times. For example, the mutation N95C is found in six of the variants, the mutation P97S is found in six of the variants, and so forth.

The variants defined by this process are listed in FIG. 14, where FIG. 13 serves as the key for FIG. 14. For example, "95" in FIG. 14 means "N95C", "355" in FIG. 14, means "P335S".

The polynucleotides encoding each proteinase K variant defined in FIG. 14 were synthesized by PCR-based assembly of synthetic oligonucleotides. The sequence of each variant was confirmed using an ABI sequencer. The ability of each of these variant proteins to hydrolyze casein was then measured simply to determine whether the proteinase K variants had any protease activity. This is the first step in exploring the sequence space. (FIG. 2, step 04).

This data, as well as data measuring the activity of proteinase K towards the hydrolysis of polylactide, can be used to analyze the data using sequence-activity correlating methods to evaluate the substitutions (steps 05 and 06 of FIG. 2). In turn, this information can be used to update knowledge base 108 and to perform additional iterations of the method to thus further explore the sequence space for improvements in desired properties.

Preliminary data indicated that changes at residues 95, 97, 138, 208, 236, 237, 265 and 299 were found only in poorly performing variants. Changes at residues 123, 145, 167, 273, 293, 310, 332, 337 and 355 were found in medium performing variants. Changes at residues 107, 151, 180, 194, 199 and 267 were found in high performing variants. Using this information the next round of sequence sets was designed and is shown in FIG. 15.

Additionally, from the results of the experiments, expert system 100, in conjunction with the sequence-activity correlating methods inferred that the proline to serine change (seen at positions 97 and 265) for flexibility and structural perturbation twice resulted in disadvantageous changes. This information was coded into the knowledge base 108 for future experiments. This is one illustration of updating knowledge base 108.

The sequence of each constructed variant is shown in FIG. 16. The activity of the variants towards casein, which is a large polymeric substrate like polylactide, was measured. Variant activity towards a modified tetrapeptide, N-succinyl-Ala-Ala-Pro-Leu-p-nitroanilide (AAPL-p-NA) which undergoes a colorimetric change upon protease-mediated hydrolysis (Sroga et al. (2002) Biotechnol Bioeng 78: 761-9), was also measured. Using this substrate, the activity of the variants at three different pH values (7, 5.5 and 4.5) was measured. The activity of variants following a five minute heat treatment at 65° C. was also measured. The activities observed for each property measured are shown in FIG. 17.

For each of the proteinase K activities tested, a partial least squares regression (PLSR) was used to model the relationship between amino acid substitution and proteinase activity (the sequence-activity relationship) for variants 10-49. The application of these methods to nucleic acids, peptides and proteins has been described previously. See, for example, Geladi et al.,1986, Analytica Chimica Acta 186: 1-17; Hellberg et al., 1987, J Med Chem 30: 1126-35; Eriksson et al., 1990, Acta Chem Scand 44: 50-55; Jonsson et al., 1993, Nucleic Acids Res. 21: 733-739; Norinder et al., 1997, J Pept Res 49: 155-62; Bucht et al., 1999, Biochim Biophys Acta 1431: 471-82.

The PLSR-based sequence activity model was used to assign a regression coefficient to each varied amino acid. The predicted activity for a proteinase K variant was calculated by summing the regression coefficients for amino acid substitutions that are present in that variant. In this case, terms to account for interactions between the varied amino acids were not included, although this can also be done. See, for example, Aita et al., 2002, Biopolymers 64: 95-105. FIG. 18 shows a correlation between the predictions of the sequence-activity model and the measured ability of heat-treated proteinase K variants to hydrolyze AAPL-p-NA.

The utility of the sequence-activity model was tested for its ability to predict the activity of variants that have not been measured, or to identify amino acid substitutions that contribute positively to a specific protein property and that can then be experimentally combined. To test the sequence activity model for heat-tolerant hydrolyzers of AAPL-p-NA, the regression coefficients from the model were tested, as shown in FIG. 19.

Four of the amino acid changes had been incorporated into the variants were predicted to have a positive effect on the activity of proteinase K after heating. These were K208H, V267I, G293A and K332R. Among the variants synthesized in the initial set of 48, one (NS40) contained three of these changes (V267I, G293A and K332R) and one (NS19) contained the other (K208H). To test the predictive power of our model, a variant (NS56) containing all four of these changes was synthesized and its activity was compared with that of NS19 and NS40.

As shown in FIG. 20, combining the four changes identified by the PLSR model produced a variant with greater post-heat treatment activity towards AAPL-p-NA than the single or triple changes. By synthesizing and measuring the activities of only 48 variants a new variant that was further improved for measured activity was designed. This demonstrates that the combination of low-throughput screening and mathematical analysis is useful for protein engineering.

The current paradigm for empirical protein engineering is to employ high throughput screens to test libraries of thousands of variants. See, for example, Lin et al., 2002, Angew Chem Int Ed Engl 41: 4402-25. In general, high throughput screens do not measure all of the properties that are important for the final application. One common way of overcoming this discrepancy is the use of tiered screens, in which high throughput screens that measure only one or two of the properties of interest are followed by lower throughput screens that more accurately reflect the desired protein characteristics. See, for example, Ness et al., 2000, Adv Protein Chem 55: 261-292. This technique relies on the assumption that the high throughput primary screen will identify the amino acid substitutions that are important for the final function but will also select some false positives. False positives do not actually contribute to the final function and are eliminated by subsequent screens. The alternative possibility, that amino acids that would be beneficial for the final application may be missed by the initial high throughput screen (false negatives), is seldom considered. By prematurely discarding substitutions that would be beneficial for the desired function, the protein engineering process may be unnecessarily prolonged or even fail.

Having measured several properties of the proteinase K variants described above and validated the predictive power of the sequence-activity modeling of the present invention, the validity of the high throughput screening approach was explored in more depth. Although no high throughput screening was explored in this example, all of the assays described above could easily be adapted for use as high throughput primary screens. Hydrolysis of casein incorporated into media plates has been used as a primary screen for protease libraries. See, for example, Ness et al., 1999, Nat Biotechnol 17: 893-896; Ness et al., 2002, Nat Biotechnol 20: 1251-5. Hydrolysis of AAPL-p-NA has also been described. See, for example, Sroga et al., 2002, Biotechnol Bioeng 78: 761-9. Testing AAPL-p-NA hydrolysis at lowered pH (5.5 or 4.5) might be considered an appropriate surrogate for the low pH tolerance that will be required by an enzyme that is producing lactic acid from polylactide. Similarly testing AAPL-p-NA hydrolysis following heat treatment may measure the stability that will be required for an enzyme that must resist the thermal stresses of incorporation into a plastic. Thermostability was expressed in three ways: (i) as the absolute level of activity remaining following heat treatment, (ii) as the activity remaining relative to the activity prior to heat treatment, and (iii) as the product of these two values. Having obtained values for each of these proteinase properties, the correlation between the properties was examine, and the amino acid substitutions that would be selected by each screen were compared.

Three representative activities were selected for further analysis: (i) activity towards AAPL-p-NA at pH 7.0, (ii) absolute activity towards AAPL-p-NA following five minutes at 65° C., and (iii) activity towards casein. For each of these activities PLSR models similar to that shown in FIG. 18 were constructed, and the regression coefficients for each amino acid substitution were calculated as shown for thermal tolerance in FIG. 19. The changes calculated to contribute positively to each property are shown in FIG. 21.

The difference between beneficial amino acids selected by the three different representative assays is striking. Use of any of these measurements as the primary assay would select some amino acid changes that are not important for the others. These would be false positives, for example, use of casein hydrolysis as a primary screen would identify six changes (S107D, S123A, V167I, Y194S, A199S and S273T) that have a negative effect on activity towards AAPL-p-NA, with or without heating. Perhaps even more importantly, the casein primary screen would have falsely attributed a negative value to three of the four changes important for thermal tolerance (K208H, V267I and G293A).

This failure of a tiered screening strategy is not simply a result of selecting an inappropriate surrogate substrate. Similar results would have been seen had activity towards AAPL-p-NA been used as a primary screen followed by a test for thermal tolerance. In this case half of the beneficial changes would still have been discarded as false negatives (K208H and V267I). This analysis shows that measuring properties that are different from those of the final application can result both in incorporation of sequence changes that do not contribute to the desired phenotype, as well as omission of those that do.

A method for engineering proteins based on design, synthesis and testing of small numbers of individual variants followed by mathematical modeling to determine a sequence-activity relationship has been described. Sequence-activity models that can be used predictively to design improved variants have also been described.

By incorporating the principles of experimental design, individual design and synthesis of sequence variants allows a more efficient search of sequence space than a library approach (Hellberg et al. (1991) *Int J Pept Protein Res* 37: 414-424). Another advantage of the modeling approach is that it facilitates empirical protein engineering but requires only very low numbers of variants to be tested. This means that the need for high throughput screens is obviated. This analysis indicates that high throughput and tiered screening can be fundamentally flawed strategies for protein engineering. Both conserved reaction conditions and use of the same substrate appear susceptible to selection of false positives and rejection of false negatives. The performance of high throughput screens will be further compromised when the primary screen is selected on the basis of throughput rather than faithful replication of the final application.

6.2 Identifying a Set of Substitutions and Defining a Set of Variants Representing that Sequence Space for Antibodies with Improved Neutralization of Respiratory Syncitial Virus In this example, the optimization procedures of the present invention are illustrated for an antibody that binds and neutralizes Respiratory Syncytial Virus (RSV). The sequence of one such antibody is publicly available (Genbank accession #AAF21612). A significant benefit of the computational antibody design system using the methods described in this invention is that only relatively small numbers of variants need to be synthesized and tested. This allows the use of functional tests that are more comprehensive than binding assays. Viral neutralization for example, is an important antibody function but the sequence and structural determinants are poorly understood.

Methods used to identify substitutions in the framework and CDR regions of the heavy chain of the AAF21612 antibody sequence are as follows. The sequence of the heavy chain of the AAF21612 antibody was aligned using the kabat numbering system with germline human ig heavy chain sequences retrieved from the VBase database. A total of 49 sequences were aligned. This alignment may not limited to germline human sequences. Alternatively, all sequences that are in the same structural class as AAF21612 as defined by Chothia and Lesk (Chothia and Lesk, 1986, EMBO Journal 5, 823-826) can be used.

These 49 sequences were processed and substitutions scored according to a modified version of the scheme shown in FIG. 3. The modified process is shown in FIG. 22.

Rule 1a. Align the sequences using kabat numbering and select all substitutions found in any of the germline sequences. Classify the substitutions into two categories: (i) substitutions found in the framework region and (ii) substitutions found in the CDR.

Rule 1b. Reconstruct a phylogenetic tree using the Clustal W software based on the amino acid alignment in the framework region. For each substitution, calculate the evolutionary proximity of the closest germline in which that substitution occurs. The evolutionary proximity EP is calculated as follows:

$$p = n_d/n$$

where,
p is the p-distance,
$n_d$ is the number of amino acid differences between two sequences; and
n is the total number of amino acids in the protein.
Further, $$d = -\ln(1-p)$$

where,
d is the Poisson-corrected p-distance between two sequences; and
$\ln(1-p)$ is the natural logarithm of the p-distance.
And, $$EP = 1/d$$

where,
EP is the evolutionary proximity.

Rule 1c. For each substitution in the framework group and in the CDR, calculate the favorability of that substitution using a PAM100 matrix.

$$SM = PAM(A_o, A_s)/10$$

where,
$A_o$ is the original amino acid at a position,
$A_s$ is the substitution amino acid, and
$PAM(A_o, A_s)$ is a measure of the average probability that $A_o$ is substituted with $A_s$ in a large set of protein homolog families.

Rule 2b. For each position, calculate the site heterogeneity, that is a measure of the number of different amino acids present at that position. The site heterogeneity is calculated as the number of different amino acids seen at a position in the set of homologs (SH).

Rule 3b. For each position calculate the site entropy as follows:

$$SE = -\Sigma\{(P_{Ai}/N) \times \ln(P_{Ai}/N)\}$$

where,
N is the number of homologous sequences,
$P_{Ai}$ is the number of times amino acid i occurs at position P,
$\ln(P_{Ai}/N)$ is the natural log of $P_{Ai}/N$, and
$\Sigma$ is the sum for all amio acids for position P.

Rule 4b. For each substitution count the number of times it occurs in the set of homologs (SN)

The total score is then calculated for framework and CDR region substitutions as follows:

$$Score_{FW} = f(EP) \times f(SH) \times f(SE) \times f(SN) \times f(SM),$$

where f( ) is a mathematical function. In this case the function was the parameter in the parentheses multiplied by 1, but the use of functions allows different weights to be applied in subsequent cycles.

$Score_{CDR} = f(SE) \times f(SN) \times f(SM)$, where f( ) is a mathematical function. In this case the function f( ) was the parameter in the parentheses multiplied by 1, but the use of functions f( ) allows different weights to be applied in subsequent cycles.

Based in the above scores, twenty substitutions in both the CDR and framework were identified. The results from use of this substitution-scoring scheme is shown in Table 1:

TABLE 1

| Framework substitutions | | CDR substitutions | |
|---|---|---|---|
| K78R | 0.465651 | V30M | 35.63365 |
| H73Q | 0.398614 | D65N | 35.55048 |
| S79A | 0.389751 | G51S | 32.24937 |
| L08V | 0.352089 | N31S | 30.06633 |
| S24T | 0.345752 | L52aY | 30.05984 |
| L01V | 0.338391 | L52aN | 9.380159 |
| S20A | 0.337918 | N31H | 25.66902 |
| G26S | 0.337206 | E56K | 25.53363 |
| D27S | 0.333916 | D65T | 22.22917 |
| V45I | 0.321903 | F33V | 21.71887 |
| L42V | 0.311439 | A53D | 21.88011 |
| C19A | 0.280519 | A53P | 19.17291 |
| S68N | 0.279479 | A53Q | 12.47777 |
| M74L | 0.258614 | F59V | 16.86972 |
| N75S | 0.254877 | V55L | 16.06146 |
| I69T | 0.243678 | G51N | 13.5927 |
| T21S | 0.238389 | E56Q | 11.17192 |
| R13S | 0.227712 | V55F | 10.78488 |
| V86R | 0.221026 | F33I | 9.900269 |
| G85A | 0.21849 | S62T | 8.950517 |

A set of forty variants were then designed with the following criteria:
1. Include five substitutions in each variant
2. Maximize the number of different pairs of substitutions that occur. If each variant contains five substitutions, it contains ten sets of pairs. There is thus a maximum of 400 pairs represented in forty variants. The variant set below was optimally design to maximize the number of pairs observed.

In addition, the relative number of framework versus CDR substitution can be modulated. A maximum number of framework and/or CDR substitutions in a variant is set.

This set was calculated by in silico evolution. An initial set of variants each containing five substitutions was randomly chosen. Substitutions were then altered randomly. If a change increased the number of substitution pairs in the variant set it was accepted. Otherwise it was rejected. The process continued for 10,000 iterations. The final set of variants is shown in Table 2.

TABLE 2

| Variant-1 | L01V | S20A | G26S | T21S | F59V |
|---|---|---|---|---|---|
| Variant-2 | S20A | L42V | C19A | S68N | G85A |
| Variant-3 | S79A | L08V | L01V | R13S | G85A |
| Variant-4 | S79A | N75S | V30M | F59V | V55F |
| Variant-5 | N31S | C19A | E56K | A53D | V86R |
| Variant-6 | H73Q | S68N | R13S | V30M | A53P |
| Variant-7 | K78R | M74L | V86R | G85A | G51N |
| Variant-8 | L08V | S20A | L52aN | G51N | F33I |
| Variant-9 | V45I | C19A | D65N | L52aN | N31S |
| Variant-10 | G26S | M74L | N75S | R13S | A53Q |
| Variant-11 | L01V | V86R | L52aN | A53D | V55L |
| Variant-12 | L42V | N31S | L52aY | G51S | F59V |
| Variant-13 | L08V | D65T | A53D | L52aY | F33V |
| Variant-14 | S68N | G51S | F59V | V55L | F33I |
| Variant-15 | K78R | H73Q | S79A | L52aY | F33I |
| Variant-16 | G26S | D27S | V45I | G51N | E56Q |
| Variant-17 | K78R | C19A | N75S | I69T | N31H |
| Variant-18 | V45I | T21S | G85A | V30M | V55L |
| Variant-19 | K78R | S20A | D65N | G51S | E56Q |
| Variant-20 | K78R | D27S | D65T | F33V | S62T |
| Variant-21 | S79A | L42V | A53Q | V55L | G51N |
| Variant-22 | M74L | I69T | D65T | E56Q | F33I |
| Variant-23 | S24T | L01V | I69T | G51S | A53P |
| Variant-24 | V45I | L42V | M74L | N31H | A53P |
| Variant-25 | L42V | I69T | T21S | V86R | E56K |
| Variant-26 | S20A | I69T | V30M | N31S | F33V |
| Variant-27 | G26S | S68N | L52aY | E56K | D65T |
| Variant-28 | C19A | V86R | F33V | A53Q | F59V |
| Variant-29 | H73Q | L08V | N31H | V55L | S62T |
| Variant-30 | K78R | L08V | G26S | N31S | V55F |
| Variant-31 | S20A | D27S | E56K | A53Q | V55F |
| Variant-32 | S79A | S24T | S68N | T21S | A53D |
| Variant-33 | L42V | R13S | D65N | V55F | F33I |
| Variant-34 | D27S | G85A | G51S | L52aN | N31H |
| Variant-35 | N75S | T21S | F33V | A53P | S62T |
| Variant-36 | R13S | L52aY | F33V | V55L | E56Q |
| Variant-37 | L01V | V45I | S68N | V55F | S62T |
| Variant-38 | L08V | S24T | C19A | V30M | E56Q |
| Variant-39 | S79A | D27S | C19A | M74L | N31S |
| Variant-40 | H73Q | S24T | D27S | V86R | D65N |

6.3 Identifying a Set of Substitutions and Defining a Set of Variants Representing that Sequence Space for Humanizing and Optimizing Murine Antibodies for Neutralizing of Respiratory Syncitial Virus In this example, a humanization procedure for a murine antibody RSV19 that binds and neutralize RSV (Respiratory Syncytial Virus) is illustrated. A significant benefit of the computational antibody design system using the methods described in this invention is that only small numbers of variants will be synthesized and tested. This allows the use of functional tests that are more complicated than selection for binding. Antibody humanization is an important antibody function but the sequence and structural determinants are poorly understood.

The methods used to identify substitutions in the framework and CDR regions of the heavy chain of the RSV-19 antibody sequence are as follows. The sequence of the heavy chain of the RSV-19 antibody was aligned using the kabat numbering system with germline human ig heavy chain sequences retrieved from VBase database This alignment may not limited to germline human sequences. Alternatively, all human antibody sequences that are in the same structural class as AAF21612 as defined by Chothia and Lesk (Chothia and Lesk, 1986, EMBO Journal 5, 823-826) can be used. A total of 45 sequences were aligned.

The sequences were processed and substitutions scored according to a modified version of the scheme shown in FIG. 3. The modified process is shown in FIG. 23.

Rule 1a. Align sequences using kabat numbering and select all substitutions found in any of the germline sequences. Classify the substitutions into two categories: (i) substitutions found in the framework region and (ii) substitutions found in the CDR. Select only these substitutions and consider them separately.

Rule 1b. Reconstruct a phylogenetic tree using the Clustal W software based on the amino acid alignment in the framework region. For each substitution, calculate the evolutionary proximity of the closest germline in which that substitution occurs. The evolutionary proximity (EP) is calculated, where EP is as defined in Section 6.2.

Rule 1c. For each substitution in the framework group and in the CDR, calculate the favorability of that substitution using a PAM100 matrix. SM is as defined in Section 6.2.

Rule 2b. For each position calculate the site heterogeneity, that is a measure of the number of different amino acids present at that position. The site heterogeneity is calculated as the number of different amino acids seen at a position in the set of homologs (SH).

Rule 3b. For each position calculate the site entropy SE using the algorithm describe in Section 6.2.

Rule 4b. For each substitution, count the number of times it occurs in the set of homologs (SN).

The total score is then calculated for framework and CDR region substitutions as follows:

$$Score_{FW} = f(EP) \times f(SH) \times f(SE) \times f(SN) \times f(SM),$$

where f( ) is a mathematical function. In this case the function was the parameter in the parentheses multiplied by 1, but the use of functions allows different weights to be applied in subsequent cycles.

$$Score_{CDR} = f(SE) \times f(SN) \times f(SM),$$

where f( ) is a mathematical function. In this case the function was the parameter in the parentheses multiplied by 1, but the use of functions allows different weights to be applied in subsequent cycles.

Based on the above scores, twenty substitutions in both the CDR and the framework were identified. The results of using this substitution-scoring scheme are shown in Table 3:

TABLE 3

| Framework substitutions | | CDR substitutions | |
|---|---|---|---|
| I46V | 0.389716 | D31S | 30.52868 |
| K19R | 0.364451 | V53T | 28.91288 |
| D69N | 0.330972 | D52cS | 28.58028 |

TABLE 3-continued

| Framework substitutions | | CDR substitutions | |
|---|---|---|---|
| R13K | 0.314539 | N52aS | 26.10288 |
| T82aA | 0.304669 | M35bV | 25.5501 |
| I29F | 0.275096 | K30S | 24.93946 |
| N73T | 0.270393 | Q54Y | 23.36634 |
| S71K | 0.268009 | Q60K | 23.19751 |
| T70S | 0.264867 | D52bG | 22.92382 |
| A16G | 0.262967 | H35S | 21.86205 |
| A85V | 0.261951 | E52D | 20.6664 |
| S72N | 0.258769 | D50S | 20.49003 |
| T66S | 0.253018 | M65I | 20.19161 |
| T23A | 0.2495 | N52aG | 20.19023 |
| N90R | 0.249449 | A63V | 19.17104 |
| A67R | 0.24173 | K58S | 18.77169 |
| Q41K | 0.22512 | E52S | 18.50896 |
| D69T | 0.218449 | F59V | 18.24618 |
| N28T | 0.217729 | D52cN | 17.85268 |
| R38A | 0.215293 | P57D | 17.60608 |

A set of forty variants were then designed with the following criteria:

1. Include four to six substitutions in each variant
2. Maximize the number of different pairs of substitutions that occur. If each variant contains five substitutions, it contains ten sets of pairs. There is thus a maximum of 400 pairs represented in forty variants. The variant set below was optimally designed using the evolutionary algorithm to maximize the number of pairs observed.

In addition, the relative number of framework versus CDR substitution can be modulated. A maximum number of framework and/or CDR substitutions in a variant can be set. For humanization, substitutions of human residues in framework regions are preferred. Substitutions in the CDR are designed to retain the activity while changing the amino acid in framework region more biased towards human sequences.

This set was calculated by in silico evolution. An initial set of variants each containing five substitutions was chosen randomly. Substitutions were then altered randomly. If a change increased the number of substitution pairs in the variant set it was accepted. Otherwise it was rejected. The process continued for 10000 iterations. The final set of variants is shown in Table 4.

TABLE 4

| | | | | | |
|---|---|---|---|---|---|
| Variant-1 | I29F | N73T | S71K | Q41K | N52aG |
| Variant-2 | N73T | A85V | S72N | T66S | R38A |
| Variant-3 | D69N | R13K | I29F | D69T | R38A |
| Variant-4 | D69N | N90R | D31S | N52aG | F59V |
| Variant-5 | N52aS | Q54Y | Q60K | H35S | E52S |
| Variant-6 | K19R | T66S | D69T | D31S | D50S |
| Variant-7 | I46V | T23A | N28T | R38A | K58S |
| Variant-8 | R13K | N73T | K30S | K58S | D52cN |
| Variant-9 | A16G | S72N | V53T | K30S | D52bG |
| Variant-10 | S71K | T23A | N90R | D69T | M65I |
| Variant-11 | I29F | N28T | K30S | H35S | A63V |
| Variant-12 | A85V | N52aS | M35bV | K30S | D31S |
| Variant-13 | R13K | D52bG | H35S | D50S | M65I |
| Variant-14 | T66S | D52cS | N52aG | A63V | D50S |
| Variant-15 | I46V | K19R | D69N | M35bV | D52cN |
| Variant-16 | S71K | T70S | A16G | K58S | E52S |
| Variant-17 | I46V | S72N | N90R | A67R | Q54Y |
| Variant-18 | A16G | Q41K | R38A | D31S | A63V |
| Variant-19 | I46V | N73T | V53T | D52cS | E52S |
| Variant-20 | I46V | T70S | D52bG | E52D | P57D |
| Variant-21 | D69N | A85V | M65I | A63V | K58S |
| Variant-22 | T23A | A67R | D52bG | E52S | D52cN |
| Variant-23 | T82aA | I29F | A67R | D52cS | D50S |
| Variant-24 | A16G | A85V | T23A | Q54Y | D50S |
| Variant-25 | A85V | A67R | Q41K | N28T | Q60K |
| Variant-26 | N73T | A67R | D31S | N52aS | E52D |
| Variant-27 | S71K | T66S | M35bV | Q60K | D52bG |
| Variant-28 | S72N | N28T | E52D | M65I | N52aG |
| Variant-29 | K19R | R13K | Q54Y | A63V | P57D |
| Variant-30 | I46V | R13K | S71K | N52aS | F59V |
| Variant-31 | N73T | T70S | Q60K | M65I | F59V |
| Variant-32 | D69N | T82aA | T66S | Q41K | H35S |
| Variant-33 | A85V | D69T | V53T | F59V | D52cN |
| Variant-34 | T70S | R38A | D52cS | K30S | Q54Y |
| Variant-35 | N90R | Q41K | E52D | D50S | D52cN |
| Variant-36 | D69T | M35bV | E52D | A63V | P57D |
| Variant-37 | I29F | A16G | T66S | F59V | P57D |
| Variant-38 | R13K | T82aA | S72N | D31S | E52S |
| Variant-39 | D69N | T70S | S72N | T23A | N52aS |
| Variant-40 | K19R | T82aA | T70S | N28T | V53T |

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Aspects of the present invention can be implemented as a computer program product that comprises a computer program mechanism embedded in a computer readable storage medium. For instance, the computer program product could contain the program modules and/or data structures shown in FIG. 1. These program modules may be stored on a CD-ROM, magnetic disk storage product, digital video disk (DVD) or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for determining a measure of confidence for a descriptor in a first sequence activity relationship for an antibody of interest, the method comprising:

(a) identifying a plurality of positions in said antibody of interest and, for each respective position in said plurality of positions, one or more substitutions for the respective position, wherein the plurality of positions and the one or more substitutions for each respective position in the plurality of positions collectively define an antibody sequence space;

(b) selecting a first plurality of variants of the antibody of interest, thereby forming a variant set, wherein said variant set comprises a subset of said antibody sequence space, wherein each respective variant in the first plurality of variants has one or more substitutions in the amino acid sequence of the antibody of interest;

(c) modeling, using a suitably programmed computer, a plurality of sequence-activity relationships between (i) a respective plurality of descriptors, wherein each descriptor in the respective plurality of descriptors is a descriptor for one or more corresponding substitutions at one or more corresponding positions of the antibody of interest in the variant set and (ii) a plurality of quantitative measures of a property, wherein each quantitative measure in the plurality of quantitative measures is a measurement of the property exhibited by a respective variant in the variant set, the plurality of sequence-activity relationships including the first sequence activity relationship, and wherein each respective sequence-activity relationship in said plurality of sequence-activity relationships includes at least one descriptor that is found in another sequence-activity relationship in said plurality of sequence-activity relationships;

each respective sequence-activity relationship in said plurality of sequence-activity relationships is either
- (A) between (i) a subset of the plurality of descriptors and (ii) the plurality of quantitative measures or
- (B) between (i) the plurality of descriptors and (ii) a subset of the plurality of quantitative measures;

each descriptor in the plurality of descriptors is weighted by a corresponding weight in a plurality of weights, and wherein said modeling comprises determining, for each respective weight in the plurality of weights, a respective first value and a respective second value for the respective weight using sequence-activity relationships in the plurality of sequence-activity relationships that include the descriptor corresponding to the weight, wherein the respective second value is a measure of confidence in the respective first value.

2. The method of claim 1, the method further comprising repeating said selecting (b), and said modeling (c) until a variant in said variant set exhibits a value for said property that exceeds a predetermined value.

3. The method of claim 2 wherein said predetermined value is a value that is greater than the value for the property that is exhibited by said antibody of interest.

4. The method of claim 1, the method further comprising repeating said selecting (b), and said modeling (c) until a variant in said variant set exhibits a value for said property that is less than a predetermined value.

5. The method of claim 1, wherein said plurality of positions and the one or more substitutions for each respective position in the plurality of positions are identified by said identifying (a) using a plurality of rules.

6. The method of claim 5, wherein each rule in the plurality of rules defines an action to be taken in response to a computational test selected from the group of computational tests consisting of:
- (i) a proximity of a position in the plurality of positions to a structurally defined region within the antibody;
- (ii) a physico-chemical property of an amino acid at a position within a plurality of antibody sequences;
- (iii) a principal component analysis of amino acids found at one or more positions within a plurality of antibody sequences;
- (iv) a presence or an absence of a substitution in an antibody that is homologous to said antibody of interest;
- (v) a presence or an absence of a substitution in a specific class of antibodies that are homologous to said antibody of interest;
- (vi) a favorability of a substitution to a position in the antibody of interest calculated using a substitution matrix;
- (vii) a probability of a substitution to a position in the antibody of interest calculated from a conservation index;
- (viii) a favorability of a substitution to a position in the antibody of interest calculated from a comparison of homologous sequences;
- (ix) a mutability of a position in the antibody of interest calculated from a comparison of homologous sequences;
- (x) a favorability of a substitution to a position in the antibody of interest calculated from a comparison of structures that are homologous to said antibody of interest; and
- (xi) a mutability of a position in the antibody of interest calculated from a comparison of structures that are homologous to said antibody of interest.

7. The method of claim 1, wherein a descriptor in the plurality of descriptors is
- (i) a substitution at a position in said plurality of positions represented by all or a portion of the variants in said variant set,
- (ii) a plurality of substitutions at a position in said plurality of positions represented by all or a portion of the variants in said variant set, or
- (iii) one or more substitutions in one or more positions in said plurality of positions represented by all or a portion of the variants in said variant set.

8. The method of claim 7, wherein a sequence-activity relationship in said plurality of sequence activity relationships is modeled by said modeling (c) by a method that comprises regressing:

$$V_{measured} = W_{11}P_1S_1 + W_{12}P_1S_2 + \ldots + W_{1N}P_1S_N + \ldots + W_{M1}P_MS_1 + W_{M2}P_MS_2 + \ldots + W_{MN}P_MS_N$$

wherein,
- M and N are each positive integers;
- $V_{measured}$ is the measured property exhibited by variants in said variant set;
- $W_{MN}$ is a contribution to the measured property by substitution N at position M;
- $P_M$ is a position in said plurality of positions in said antibody of interest; and
- $S_N$ is a substitution at a position in the plurality of positions in said antibody of interest.

9. The method of claim 8, wherein said regressing comprises linear regression, non-linear regression, logistic regression, multivariate data analysis, or partial least squares projection to latent variables.

10. The method of claim 1, wherein the modeling of the sequence-activity relationship in said plurality of sequence activity relationships in said modeling (c) comprises computation of a neural network, computation of a Bayesian model, computation of a generalized additive model, computation of a support vector machine, or classification using a regression tree.

11. The method of claim 1, wherein said modeling (c) comprises boosting or adaptive boosting.

12. The method of claim 1, the method further comprising redefining said variant set to comprise variants in said antibody sequence space that include substitutions in said plurality of positions that are selected based on a function of said respective first values and said respective second values by:
- computing a modified respective first value by modifying the respective first value based on a function of the corresponding respective second value; and
- computing a predicted score, for each respective variant in a population of variants of said antibody of interest, using the modified first value, wherein each variant in said population of variants includes a substitution at one or more positions in said plurality of positions in said antibody of interest; and
- redefining said variant set by selecting variants from among said population of variants as a function of the predicted score received by each variant in said set of variants.

13. The method of claim 12, the method further comprising:
  ranking said population of variants, wherein each variant in said population of variants is ranked based on the predicted score received by the variant based upon a sequence-activity relationship in the plurality of sequence-activity relationships or a combination of sequence-activity relationships in the plurality of sequence-activity relationships; and
  said selecting comprising accepting a predetermined percentage of the top ranked variants in said population of variants for said variant set.

14. The method of claim 12, wherein said redefining comprises redefining said variant set to comprise one or more variants of the antibody that are not in the antibody sequence space of said identifying (a).

15. The method of claim 12, wherein said redefining comprises redefining said variant set to comprise one or more variants each having a substitution in a position in said plurality of positions not present in any variant in the variant set selected by said selecting (b).

16. The method of claim 5, wherein the contribution of each respective rule in said plurality of rules to the defining of said antibody sequence space is independently weighted by a rule weight in a plurality of rule weights corresponding to the respective rule; the method further comprising:
  adjusting one or more rule weights in said plurality of rule weights based on a comparison, for each respective substitution at each position in the plurality of positions in the variant set, of (i) a value derived for the respective substitution from a sequence-activity relationship in the plurality of sequence-activity relationships or a combination of sequence activity relationships in the plurality of sequence activity relationships, and (ii) a score assigned by the plurality of rules to the respective substitution; and
  repeating said identifying step using said rule weights, thereby redefining said plurality of positions and, for each respective position in said plurality of positions, redefining the one or more substitutions for the respective position; and
  redefining said variant set to comprise one or more variants that are not in the subset of the antibody sequence space formed in said selecting (b).

17. The method of claim 1 wherein
said property of a variant in said variant set is a level of expression of said variant in a host cell, a susceptibility of said variant to a post-translational modification, a killing of a pathogenic organism or a virus resulting from an activity of said variant, a modulation of a signaling pathway by said variant, a modulation of surface density of a cell-surface receptor by said variant, a binding of a cellular growth factor receptor by said variant, a binding of a receptor or a mediator of tumor-driven angiogenesis by said variant, a binding of a B cell surface antigen by said variant, a binding of a protein synthesized by said variant, an induction of an antibody-mediated cell killing by said variant, an induction of an antibody-dependent macrophage activity by said variant, an induction of a histamine release by said variant, an induction of or cross-reaction with an anti-idiotype antibody by said variant, an immunogenicity of said variant, a reduction of viral titer by said variant or an immunomodulatory activity of said variant.

18. The method of claim 1, wherein a sequence-activity relationship in said plurality of sequence-activity relationships has the form:

$$Y=f(w_1x_1, w_2x_2, \ldots, w_ix_i)$$

wherein,
  Y is a quantitative measure of said property in said plurality of quantitative measures;
  $x_i$ is a descriptor, in the plurality of descriptors, of a substitution, a combination of substitutions, or a component of one or more substitutions, at one or more positions in said plurality of positions;
  $w_i$ is a weight applied to descriptor $x_i$; and
  f( ) is a mathematical function.

19. The method of claim 18, wherein said modeling of a sequence-activity relationship in a plurality of sequence-activity relationships comprises regressing:

$$Y=f(w_1x_1, w_2x_2, \ldots, w_ix_i).$$

20. The method of claim 19, wherein regressing comprises linear regression, non-linear regression, logistic regressing, or partial least squares projection to latent variables.

21. The method of claim 1 wherein said antibody of interest is from rat, mouse, chicken, cow, monkey, pig, dog, rabbit, or human.

22. The method of claim 1 wherein said antibody of interest is a monoclonal antibody, a bispecific antibody, a multispecific antibody, a humanized antibody, a chimeric antibody, a camelised antibody, a single domain antibody, a single-chain Fvs (ScFv), a single chain antibody, a Fab fragment, a F(ab') fragment, a disulfide-linked Fvs (sdFv), or an anti-idiotypic (anti-Id) antibody.

23. The method of claim 1 wherein said antibody of interest is an epitope-binding fragment of a monoclonal antibody, an epitope-binding fragment of a bispecific antibody, an epitope-binding fragment of a multispecific antibody, an epitope-binding fragment of a humanized antibody, an epitope-binding fragment of a chimeric antibody, an epitope-binding fragment of a camelised antibody, an epitope-binding fragment of a single domain antibody, an epitope-binding fragment of a single-chain Fvs (ScFv), an epitope-binding fragment of a single chain antibody, an epitope-binding fragment of a Fab fragment, an epitope-binding fragment of a F(ab') fragment, an epitope-binding fragment of a disulfide-linke Fvs (sdFv), or an epitope-binding fragment of an anti-idiotypic (anti-Id) antibody.

24. The method of claim 1 wherein said antibody of interest is an antibody fragment.

25. The method of claim 1 wherein a variant in the variant set comprises a monoclonal antibody, a bispecific antibody, a multispecific antibody, a humanized antibody, a chimeric antibody, a camelised antibody, a single domain antibody, a single-chain Fvs (ScFv), a single chain antibody, a Fab fragment, a F(ab') fragment, a disulfide-linked Fvs (sdFv), or an anti-idiotypic (anti-Id) antibody.

26. The method of claim 1 wherein a variant in the variant set comprises an epitope-binding fragment of a monoclonal antibody, an epitope-binding fragment of a bispecific antibody, an epitope-binding fragment of a multispecific antibody, an epitope-binding fragment of a humanized antibody, an epitope-binding fragment of a chimeric antibody, an epitope-binding fragment of a camelised antibody, an epitope-binding fragment of a single domain antibody, an epitope-binding fragment of a single-chain Fvs (ScFv), an epitope-binding fragment of a single chain antibody, an epitope-binding fragment of a Fab fragment, an epitope-binding fragment of a F(ab') fragment, an epitope-binding fragment of a disulfide-linke Fvs (sdFv), or an epitope-binding fragment of an anti-idiotypic (anti-Id) antibody.

27. The method of claim 1 wherein a variant in said variant set comprises an antibody fragment.

28. The method of claim 1 wherein a quantitative measure in said plurality of quantitative measures is measured by:
expressing a variant in the variant set in a cell line; and
measuring a cell-surface receptor surface density of said cell line that includes said variant.

29. The method of claim 1 wherein a quantitative measure in said plurality of quantitative measures is measured by:
expressing a variant in the variant set in a cell line; and
measuring a cell surface receptor internalization rate of said cell line that includes said variant.

30. The method of claim 1 wherein a quantitative measure in said plurality of quantitative measures is measured by:
expressing a variant in the variant set in a cell line; and
measuring a cell surface receptor post-translational modification of said cell line that includes said variant.

31. The method of claim 30 wherein said cell surface receptor post-translational modification is phosphorylation.

32. The method of claim 1 wherein a quantitative measure in said plurality of quantitative measure is measured by:
expressing a variant in the variant set in a cell line; and
measuring a binding of an antigen to said cell line that includes said variant.

33. The method of claim 32 wherein said antigen is a cellular growth factor receptor, a receptor of tumor-driven angiogenesis, a mediator of tumor-driven angiogenesis, a B cell surface antigen, or a protein synthesized by or in response to a pathogen.

34. The method of claim 1 wherein a quantitative measure in said plurality of quantitative measures is measured by measuring the ability for a variant in said variant set to immunospecifically bind to an antigen.

35. The method of claim 34 wherein said measuring comprises placing said variant in solution, spotting said variant onto a microchip, placing a polynucleotide encoding said variant in bacteria, placing a polynucleotide that codes for said variant in a spore, placing a polynucleotide that codes for said variant in a plasmid, or placing a polynucleotide that codes for said variant in phage.

36. The method of claim 1 wherein a quantitative measure in said plurality of quantitative measures is measured by assaying for a reduction of a viral titer of a virus in infected tissue culture cells by a variant in all or said portion of the variant set.

37. The method of claim 36, wherein the virus is hepatitis A virus, hepatitis B virus, hepatitis C virus, human papilloma virus, human immunodeficiency virus, respiratory syncitial virus, human adenovirus, fowl adenovirus 1, African swine fever virus, lymphocytic choriomeningitis virus, ippy virus, lassa virus, equine arteritis virus, human astrovirus 1, autographa californica nucleopolyhedrovirus, plodia interpunctella granulovirus, commelina yellow mottle virus, rice tungro bacilliform virus, mushroom bacilliform virus, infectious pancreatic necrosis virus, infectious bursal disease virus, drosophila x virus, alfalfa mosaic virus, tobacco streak virus, brome mosaic virus, cucumber mosaic virus, apple stem grooving virus, carnation latent virus, cauliflower mosaic virus, chicken anemia virus, beet yellows virus, cowpea mosaic virus, tobacco ringspot virus, avian infectious bronchitis virus, alteromonas phage pm2, pseudomonas phage phi6, hepatitis delta virus, carnation ringspot virus, red clover necrotic mosaic virus, sweet clover necrotic mosaic virus, pea enation mosaic virus, ebola virus zair, soil-borne wheat mosaic virus, beet necrotic yellow vein virus, sulfobolus virus 1, maize streak virus, beet curly top virus, bean golden mosaic virus , duck hepatitis B virus, human herpesvirus, human herpesvirus, ateline herpesvirus 2, barley stripe mosaic virus, cryphonectria hypovirus 1-ep713, raspberry bushy dwarf virus, acholeplasma phage 151, chilo iridescent virus, goldfish virus 1, enterobacteria phage ms2, enterobacteria phage qbeta, thermoproteus virus 1, maize chlorotic mottle virus, maize rayado fino virus, coliphage phix174, spiromicrovirus, spiroplasma phage, bdellomicrovirus, bdellovibrio phage, chlamydiamicrovirus, chlamydia phage 1, coliphage t4, tobacco necrosis virus, nodamura virus, influenzavirus a, influenzavirus C, thogoto virus, rabbit (shope) papillomavirus, human parainfluenza virus, measles virus, rubulavirus, mumps virus, human respiratory syncytial virus, gaeumannomyces graminis virus, penicillium chrysogenum virus, white clover cryptic virus, white clover cryptic virus 2, minute mice virus, adeno-associated virus, junonia coenia densovirus, bombyx mori virus, aedes aegypti densovirus, 1-paramecium bursaria chlorella nc64a virus, paramecium bursaria chlorella virus, 2-paramecium bursaria chlorella pbi virus, 3-hydra viridis chlorella virus, human poliovirus 1, human rhinovirus 1A, hepatovirus, encephalomyocarditis virus, foot-and-mouth disease virus, acholeplasma phage 12, coliphage t7, campoletis sonorensis virus, cotesia melanoscela virus, potato virus X, potato virus Y, ryegrass mosaic virus, barley yellow mosaic virus, fowlpox virus, sheep pox virus, swinepox virus, molluscum contagiosum virus, yaba monkey tumor virus, entomopoxvirus A, melolontha melolontha entomopoxvirus, amsacta moorei entomopoxvirus, chironomus luridus entomopoxvirus, reovirus 3, epizootic hemarrhogic disease virus 1, or simian rotavirus Sa11.

38. The method of claim 1 wherein a quantitative measure in said plurality of quantitative measures is measured by assaying for a reduction of a viral titer of a virus in an animal model by a variant in all or said portion of the variant set.

39. The method of claim 38 wherein the virus is hepatitis A virus, hepatitis B virus, hepatitis C virus, human papilloma virus, human immunodeficiency virus, respiratory syncitial virus, human adenovirus, fowl adenovirus 1, African swine fever virus, lymphocytic choriomeningitis virus, ippy virus, lassa virus, equine arteritis virus, human astrovirus 1, autographa californica nucleopolyhedrovirus, plodia interpunctella granulovirus, commelina yellow mottle virus, rice tungro bacilliform virus, mushroom bacilliform virus, infectious pancreatic necrosis virus, infectious bursal disease virus, drosophila x virus, alfalfa mosaic virus, tobacco streak virus, brome mosaic virus, cucumber mosaic virus, apple stem grooving virus, carnation latent virus, cauliflower mosaic virus, chicken anemia virus, beet yellows virus, cowpea mosaic virus, tobacco ringspot virus, avian infectious bronchitis virus, alteromonas phage pm2, pseudomonas phage phi6, hepatitis delta virus, carnation ringspot virus, red clover necrotic mosaic virus, sweet clover necrotic mosaic virus, pea enation mosaic virus, ebola virus zair, soil-borne wheat mosaic virus, beet necrotic yellow vein virus, sulfobolus virus 1, maize streak virus, beet curly top virus, bean golden mosaic virus, duck hepatitis B virus, human herpesvirus, human herpesvirus, ateline herpesvirus 2, barley stripe mosaic virus, cryphonectria hypovirus 1-ep713, raspberry bushy dwarf virus, acholeplasma phage 151, chilo iridescent virus, goldfish virus 1, enterobacteria phage ms2, enterobacteria phage qbeta, thermoproteus virus 1, maize chlorotic mottle virus, maize rayado fino virus, coliphage phix174, spiromicrovirus, spiroplasma phage, bdellomicrovirus, bdellovibrio phage, chlamydiamicrovirus, chlamydia phage 1, coliphage t4, tobacco necrosis virus, nodamura virus, influenzavirus a, influenzavirus C, thogoto virus, rabbit (shope)

papillomavirus, human parainfluenza virus, measles virus, rubulavirus, mumps virus, human respiratory syncytial virus, gaeumannomyces graminis virus, penicillium chrysogenum virus, white clover cryptic virus, white clover cryptic virus 2, minute mice virus, adeno-associated virus, junonia coenia densovirus, bombyx mori virus, aedes aegypti densovirus, 1-paramecium bursaria chlorella nc64a virus, paramecium bursaria chlorella virus, 2-paramecium bursaria chlorella pbi virus, 3-hydra viridis chlorella virus, human poliovirus 1, human rhinovirus 1A, hepatovirus, encephalomyocarditis virus, foot-and-mouth disease virus, acholeplasma phage 12, coliphage t7, campoletis sonorensis virus, cotesia melanoscela virus, potato virus X, potato virus Y, ryegrass mosaic virus, barley yellow mosaic virus, fowlpox virus, sheep pox virus, swinepox virus, molluscum contagiosum virus, yaba monkey tumor virus, entomopoxvirus A, melolontha melolontha entomopoxvirus, amsacta moorei entomopoxvirus, chironomus luridus entomopoxvirus, reovirus 3, epizootic hemarrhogic disease virus 1, or simian rotavirus SA11.

40. The method of claim 1 wherein a quantitative measure in said plurality of quantitative measures is measured by assaying for a change in rate of proliferation of cells grown in a culture by a variant in all or said portion of the variant set.

41. The method of 40 wherein the cells grown in the culture are tumor cells, a cell line derived from tumor cells, a cell line derived from breast cancer cells, a cell line derived from ovarian cancer cells, a cell line derived from lung cancer cells, a cell line derived from bone cancer cells, a cell line derived from fibroblast cancer cells, a cell line derived from hematopoetic cancer cells, a cell line derived from testicular cancer cells, a cell line derived from colon cancer cells, a cell line derived from prostate cancer cells, or a cell line derived from leukemia cells.

42. The method of claim 1 wherein a quantitative measure in said plurality of quantitative measures is measured by assaying for a change in rate of proliferation of a specific cell type in an animal model by a variant in all or said portion of the redefined variant set.

43. The method of 42 wherein the specific cell type is a tumor cell type.

44. The method of claim 42 wherein the specific cell type is derived from a breast cancer tumor, an ovarian cancer tumor, a lung cancer tumor, a bone cancer tumor, a fibroblast cancer, a hematopoetic cancer, a testicular cancer, a colon cancer, a prostate cancer, or a leukemia.

45. The method of claim 12, wherein each variant in the redefined variant set differs by fewer than 5 substitutions from at least one variant for which the property has been measured.

46. The method of claim 5, wherein
the contribution of each respective rule in the plurality of rules to the defining of said antibody sequence space is independently weighted by a rule weight in a plurality of rule weights corresponding to the respective rule; and
the plurality of rule weights are calculated based on a comparison, for a plurality of substitutions in the variant set of (i) a value assigned to the respective substitution by a sequence-activity relationship in the plurality of sequence-activity relationships or a combination of sequence-activity relationships in the plurality of sequence-activity relationships, and (ii) a score assigned by the plurality of rules to the respective substitution.

47. The method of claim 1, wherein said modeling (c) comprises deriving a relationship between (i) a physicochemical property of one or more substitutions at one or more positions of the antibody of interest represented by the variant set and (ii) the property measured for all or the portion of the variants in the variant set.

48. The method of claim 1, wherein the respective first value is an average of the respective weight from each sequence-activity relationship in the plurality of sequence-activity relationships that includes the respective weight.

49. The method of claim 1, wherein the respective second value for a first weight in the plurality of weights is a standard deviation of the respective weight from each sequence-activity relationship in the plurality of sequence-activity relationships that includes the respective weight.

50. The method of claim 1, the method further comprising:
(d) selecting a second plurality of variants of the antibody of interest, wherein each variant in said second plurality of variants has one or more substitutions, wherein a substitution in the one or more substitutions is characterized by a descriptor in the plurality of descriptors having a weight for which the modeling (c) determined the respective first value and the respective second value, wherein
the respective first value is positive, and
the first value is an average or mean of the weight from each sequence-activity relationship in the plurality of sequence-activity relationships that includes the weight.

51. The method of claim 50, wherein the second value is a standard deviation and the first value exceeds the second value by at least the standard deviation.

52. The method of claim 50, wherein the second value is a standard deviation and the first value exceeds the second value by at least twice the standard deviation.

53. The method of claim 50, wherein the second value is a standard deviation and the first value exceeds the second value by at least three times the standard deviation.

54. The method of claim 1, wherein the respective second value for a first weight in the plurality of weights is a variance of the respective first value for the first weight.

55. The method of claim 1, implemented on a computer.

56. The method of claim 50, wherein a substitution in the one or more substitutions is found in at three variants in the variant set.

57. The method of claim 50, wherein a first value for a descriptor is positive.

58. The method of claim 1, wherein a respective first value is a mean of the corresponding weight from each sequence-activity relationship in the plurality of sequence-activity relationships that includes the respective weight.

59. The method of claim 1, wherein a first value of a weight in the plurality of weights is a regression coefficient for the corresponding descriptor.

60. The method of claim 1, wherein a first value of a weight in the plurality of weights for a sequence-activity relationship in the plurality of sequence-activity relationships is determined by a relative contribution of the corresponding descriptor in the plurality of descriptors to the property of the antibody in the sequence-activity relationship.

61. The method of claim 1, wherein a first value of a weight in the plurality of weights for a sequence-activity relationship in the plurality of sequence-activity relationships is determined by an absolute contribution of the corresponding descriptor in the plurality of descriptors to the property of the antibody in the sequence-activity relationship.

62. The method of claim 1, the method further comprising:
(d) using said modeling (c) to identify one or more candidate substitutions in the antibody of interest, wherein the one or more candidate substitutions have a high probability of conferring an improvement to the property relative to the antibody of interest.

63. The method of claim 62, wherein said using (d) comprises selecting the one or more candidate substitutions that are characterized by a descriptor in the plurality of descriptors having a weight for which the modeling (c) determined the respective first value and the respective second value, wherein
the respective first value is positive indicating that the weight has a positive relative or absolute contribution to the property, and
the respective first value is an average or mean of the weight from each sequence-activity relationship in the plurality of sequence-activity relationships that includes the weight.

64. The method of claim 63, wherein the second value is a standard deviation and the first value exceeds the second value by at least the standard deviation.

65. The method of claim 63, wherein the second value is a standard deviation and the first value exceeds the second value by at least twice the standard deviation.

66. The method of claim 63, wherein the second value is a standard deviation and the first value exceeds the second value by at least three times the standard deviation.

67. The method of claim 63, wherein the one or more candidate substitutions are represented in two or more variants in the first plurality of variants of the antibody of interest.

68. The method of claim 64, wherein the one or more candidate substitutions are represented in two or more variants in the first plurality of variants of the antibody of interest.

69. The method of claim 66, wherein the one or more candidate substitutions are represented in two or more variants in the first plurality of variants of the antibody of interest.

70. The method of claim 63, wherein a candidate substitution in the one or more candidate substitutions is the most favorable substitution represented by the first plurality of variants of the antibody of interest.

71. The method of claim 70, wherein the second value is a standard deviation and the first value exceeds the second value by at least the standard deviation.

72. The method of claim 70, wherein the second value is a standard deviation and the first value exceeds the second value by at least twice the standard deviation.

73. The method of claim 1, wherein the variant set is synthesized as a library of variants.

74. The method of claim 73, wherein the library of variants is synthesized by one or more methods selected from the group consisting of DNA shuffling, preparing a plurality of oligonucleotides representing a plurality of desired variants in the variant set, using degenerate oligonucleotides from trinucleotides, using degenerate oligonucleotides from resin-splitting, and PCR with a mixture of mutagenic oligonucleotides.

75. The method of claim 1, wherein the measure of confidence comprises a standard deviation or variance.

* * * * *